US008217037B2

(12) United States Patent
Giordano et al.

(10) Patent No.: US 8,217,037 B2
(45) Date of Patent: Jul. 10, 2012

(54) THIAZOLE AND THIOPHENE ANALOGUES, AND THEIR USE IN TREATING AUTOIMMUNE DISEASES AND CANCERS

(75) Inventors: Anthony Giordano, Shreveport, LA (US); Kamala K. Vasu, Ahmedabad (IN); Hardik M. Thakar, Ahmedabad (IN); Rajan S. Giri, Ahmedabad (IN); Swapnil G. Yerande, Ahmedabad (IN); Gajanan S. Inamdar, Ahmedabad (IN); Vasudevan Sudarsanam, Ahmedabad (IN)

(73) Assignees: Board of Supervisors of Louisiana State University and Agricultural and Mechanical College, Baton Rouge, LA (US); B.V. Patel Pharmaceutical Education & Research Development (PERD), Ahmedadab (IN)

( * ) Notice: Subject to any disclaimer, the term of this patent is extended or adjusted under 35 U.S.C. 154(b) by 434 days.

(21) Appl. No.: 12/296,173
(22) PCT Filed: Apr. 5, 2007
(86) PCT No.: PCT/US2007/066068
§ 371 (c)(1),
(2), (4) Date: Mar. 23, 2009
(87) PCT Pub. No.: WO2007/118149
PCT Pub. Date: Oct. 18, 2007

(65) Prior Publication Data
US 2009/0306073 A1 Dec. 10, 2009

Related U.S. Application Data

(60) Provisional application No. 60/790,105, filed on Apr. 7, 2006, provisional application No. 60/795,430, filed on Apr. 26, 2006.

(51) Int. Cl.
*A61K 31/5377* (2006.01)
*C07D 413/14* (2006.01)
(52) U.S. Cl. .............. 514/234.5; 544/106; 544/111; 544/116; 514/231.2; 514/231.5
(58) Field of Classification Search ............... 544/106, 544/111, 114, 116; 514/231.2, 231.5, 234.5
See application file for complete search history.

(56) References Cited

U.S. PATENT DOCUMENTS
6,630,589 B1 10/2003 Giordano et al. ............ 546/139
6,872,850 B2 3/2005 Giordano et al. ............ 564/147

FOREIGN PATENT DOCUMENTS
WO WO 03/104218 12/2003
WO WO 2004/053087 6/2004
WO WO/2005/038436 3/2005

OTHER PUBLICATIONS

Piljai et al (2004): STN International HCAPLUS database, (Columbus, Ohio), Accession No. 2004:627180.*
Eckert et al (2000): STN International HCAPLUS database, (Columbus, Ohio), Accession No. 2000:243723.*
Sah, J.F. et al., Epigallocatechin-3-gallate inhibits epidermal growth factor receptor signaling pathway. Evidence for direct inhibition of ERK1/2 and AKT kinases. J Biol Chem, vol. 279, pp. 12755-12762 (20.
Sancho, R. et al., Immunosuppressive activity of endovanilloids: N-arachidonoyl-dopamine inhibits activation of the NF-?B, NFAT, and Activator Protein 1 signaling pathways. J. Immunology, vol. 172, pp. 2341-2351 (2004).
Shaulian, E. et al., AP-1 as a regulator of cell life and death. Nature Cell Biology, vol. 4, pp. e131-e135 (2002).
Shaw, K. et al., Immunosuppressive Drugs Prevent a Rapid Dephosphorylation of Transcription Factor NFAT1 in Stimulated Immune Cells PNAS, vol. 92, pp. 11205-11209 (1995).
Shi, Q. et al., Cooperation between transcription factor AP-1 and NF-?B in the induction of interleukin-8 in human pancreatic adenocarcinoma cells by hypoxia. J. Interferon Cytokine Res., vol. 19, pp. 1363-1371 (1999).
Sliva, D., Signaling pathways responsible for cancer cell invasion as targets for cancer therapy. Curr Cancer Drug Targets, vol. 4, pp. 327-336 (2004).
Sliva, D. et al., Protein kinase C induces motility of breast cancers by upregulating secretion of urokinase-type plasminogen activator through activation of AP-1 and NF-?B. Biochem. Biophys. Res. Comm., vol. 290, pp. 552-557 (2002).
Sliva, D. et al., Ganoderma lucidum suppresses motility of highly invasive breast and prostate cancer cells. Biochem. Biophys. Res. Comm., vol. 298, pp. 603-612 (2002).
Sreenivasan, Y. et al., Oleandrin suppresses activation of nuclear transcription factor-?B and activator protein-1 and potentiates apoptosis induced by ceramide. Biochem. Pharm., vol. 66, pp. 2223-2239 (2003).
Surh, Y.-J., Cancer chemoprevention with dietary phytochemicals. Nature Reviews, vol. 3, pp. 768-780 (2003).
Tachibana, H. et al., A receptor for green tea polyphenol EGCG Nature Struct. & Mol. Biol., vol. 11, pp. 380-381 (2004).
Whitmarsh, A. et al., Integration of MAP kinase signal transduction pathways at the serum response element. Science, vol. 269, pp. 403-407 (1995). Zhu, X. et al., Thiothalidomides: Novel Isosteric Analogues of Thalidomide with Enhanced TNF-alpha Inhibitory Activity. Journal of Medicinal Chemistry, vol. 46, pp. 5222-5229 (2003).
Eckert, K. et al., "Preparation and Characterization of Cyanovinyl-Substituted 2-Aminotheophenes and 2-Aminothiazoles and Some of Their Heterooligomers," Eur. J. Org. Chem., vol. 2000, No. 7, pp. 1327-1334 (2000).
Heyde, C. et al., "A Simple Route to N,N-Dialkyl Derivatives of 2-Amino-5-thiophenecarboxylates," Eur. J. Org. Chem., vol. 2000, No. 19, pp. 3273-3278 (2000).
Liebscher, J. et al., "Formylation Products of Thioamides; Part 11¹. A Novel Route to Substituted 2-Aminotheophenes by the Reaction of S-Alkylated Thioamides with Carboxylic Acid Derivatives," Synthesis, vol. 4, pp. 412-414 (1985).
Noack, A. et al., "Synthesis and characterisation of N,N-disubstituted 2-amino-5-acylthiophenes and 2-amino-5-acylthiazoles," Tetrahedron, vol. 58, No. 11, pp. 2137-2146 (2002).
Liebscher, J. et al., "Reactions of e-Amino and 3-Hydroxythioacrylamides with Alkylating Reagents-Synthesis of N,N-Disubstituted 2-Aminothiophenes," Journal Fuer Praktische Chemie, vol. 325, No. 1, pp. 168-172 (1983).
Abid, R. et al., "Translational Regulation of Ribonucleotide Reductase by Eukaryotic Initiation Factor 4E Links Protein Synthesis to the Control of DNA Replication," The Journal of Biological Chemistry, vol. 274, No. 50, pp. 35991-35998 (1999).

(Continued)

*Primary Examiner* — Golam M M Shameem
(74) *Attorney, Agent, or Firm* — John H. Runnels; Bonnie J. Davis

(57) ABSTRACT

Thiazole and thiophene compounds are disclosed having utility in treating inflammatory conditions, immunoinflammatory conditions, autoimmune diseases, and cancers. Methods for the synthesis of these compounds are also disclosed.

12 Claims, 15 Drawing Sheets

OTHER PUBLICATIONS

Aggarwal, B.B. et al., "Anticancer potential of curcumin: preclinical and clinical studies," Anticancer Res., vol. 23, pp. 363-398 (2003).

Ahmed, S. et al., "Green tea polyphenol epigallocatechin-3-gallate (EGCG) differentially inhibits interleukin-1b-induced expression of matrix metalloproteinase-1 and-13 in human chondrocytes," J. Pharm. Exp. Therap., 3, 767-773 (2004).

Ahn, W.S. et al., "Protective effects of green tea extracts (polyphenol E and EGCG) on human cervical lesions," Eur J Cancer Prev., vol. 12, pp. 383-390 (2003).

Angel, P.K., "The role of Jun, Fos and the AP-1 complex in cell-proliferation and transformation," Biochim. Biophys. Acta, vol. 1072, pp. 129-157 (1991).

Bancroft CC et al., "Coexpression of proangiogenic factors IL-8 and VEGF by human head and neck squamous cell carcinoma involves coactivation by MEK-MAPK and IKK-NF-kappaB signal pathways," Clin. Cancer Res., vol. 7, pp. 435-442 (2001).

Brandhuber, B.J.B.T. et al., "Three-dimensional structure of interleukin-2," Science, vol. 238, pp. 1707-1709 (1987).

Carter, P.S. et al., "Differential Expression of Myc1 and Myc2 Isoforms in Cells Transformed by eIF4E: Evidence for Internal Ribosome Repositioning in the Human c-myc 5'UTR," Oncogene, vol. 18, pp. 4326-4335 (1999).

Child, S.J. et al., "Cell type-dependent and -independent control of HER-2/neu translation," Int J Biochem. Cell Biology, vol. 31, pp. 201-213 (1999).

Child, S.J. et al., "Translational control by an upstream open reading frame in the HER-2/neu transcript," J Biol Chem, vol. 274, pp. 24335-24341 (1999).

Chow, H.H. et al., "Pharmacokinetics and safety of green tea polyphenols after multiple-dose administration of epigallocatechin gallate and polyphenol E in healthy individuals," Clin. Cancer Res., vol. 9, pp. 3312-3319 (2003.

Clemens, M.J., "Targets and mechanisms for the regulation of translation in malignant transformation," Oncogene, vol. 23, pp. 3180-3188 (2004).

Collins, T.S. et al., "Paclitaxel up-regulates interleukin-8 synthesis in human lung carcinoma through an NF-kappaB- and AP-1-dependent mechanism," Cancer Immunol Immunother, vol. 49, pp. 78-84 (2000).

Crew, J. et al., "Eukaryotic Initiation Factor-4E in Superficial and Muscle Invasive Bladder Cancer and its Correlation with Vascular Endothelial Growth Factor Expression and Tumour Progression," British Journal of Cancer, vol. 82, No. 1, pp. 161-166 (2000).

De Benedetti, A. et al., "eIF-4E expression and its role in malignancies and metastases," Oncogene, vol. 23, pp. 3189-3199 (2004).

DeBenedetti, A. et al., "Overexpression of Eukaryotic Protein Synthesis Initiation Factor 4E in HeLa Cells Results in Aberrant Growth and Morphology," Proc. Natl. Acad. Sci., vol. 87, pp. 8212-8216 (1990).

DeFatta, R.J. et al., "Elevated expression of eIF4E in confined early breast cancer lesions: possible role of hypoxia," Int. J. Cancer, vol. 80, pp. 516-522 (1999.

Duvoix, A. et al., "Effect of chemopreventive agents on glutathione S-transferase p1-1 gene expression mechanisms via activating protein 1 and nuclear factor kappaB inhibition," Biochemical Pharmacology, vol. 68, pp. 1101-1111 (2004).

Eferl, R. et al., "AP-1: A double-edged sword in tumorigenesis," Nature Reviews, vol. 3, pp. 859-868 (2003).

Hahn, W., "Rules for making human tumor cells," New Engl J Med, vol. 347, pp. 1593-1603 (2002).

Huang, S. et al., "Targeting mTOR signaling for cancer therapy," Curr Opin Pharmacol., vol. 3, pp. 371-377 (2003).

Karin, M., "How NF-kappaB is activated: the role of the IkappaB kinase (IKK) complex," Oncogene, vol. 18, pp. 6867-6874 (1999).

Karin, M. et al., "The I[kappa]B kinase (IKK) and NF-[kappa]B: key elements of proinflammatory signalling," Seminars in Immunology, vol. 12, pp. 85-98 (2000).

Karin, M. et al., "The IKK NF-kB system: A treasure trove for drug development," Nature Reviews, vol. 3, pp. 17-26 (2004).

Keum, Y.S. et al., "Inhibitory effects of the ginsenoside Rg3 on phorbal ester-induced cyclooxygenase-2 expression, NF-kappaB activation and tumor promotion," Mutation Res., vol. 523-524, pp. 75-85 (2003).

Kikuchi, T.et al., "Clarithromycin suppresses lipopolysaccharide-induce interleukin-8 production by human monocytes through AP-1 and NF-18 transcription factors," J. Antimicrobial Chemotherapy, vol. 49, pp. 645-755 (2002).

Leaf, C., "Why we're losing the war on cancer (and how to win it)," Fortune, vol. 149, pp. 77-96 (2004).

Leone, M. et al., "Cancer prevention by tea polyphenols is linked to their direct inhibition of antiapoptotic Bcl-2-family proteins," Cancer Res., 63, 8118-8121 (2003).

Li, B. et al., "Clinical outcome in stage 1 to 3 breast carcinomas and eIF4E overexpression," Ann. Surg. Soc., vol. 227, pp. 756-762 (1998).

Li, J.J. et al., "Inhibitors of both nuclear factor-kappaB and activator protein-1 activation block the neoplastic transformation response," Cancer Res., vol. 57, pp. 3569-3576 (1997).

Mamane, E. et al., "eIF4E—from translation to transformation," Oncogene, vol. 23, pp. 3172-3179 (2004).

Manning, A.M., "Transcription factors: a new frontier for drug discovery," Drug Discovery Today, vol. 1, No. 4, pp. 151-160 (1996).

Mori, N., et al., "Apoptosis induced by the histone deacetylase inhibitor FR901228 in human T-cell leukemia virus type 1-infected T-cell lines and primary adult T-cell leukemia cells," J. Virol., vol. 78, pp. 4582-4590 (2004).

Nathan, C.A. et al., Elevated expression of eIF4E and FGF-2 isoforms during vascularization of breast carcinomas Oncogene, vol. 15, pp. 1087-1095 (1997).

Nathan, C.A. et al., Expression of eIF4E during head and neck tumorigenesis: possible role in angiogenesis The Laryngoscope, vol. 109, pp. 1253-1258 (1999).

Pahl, H., "Activators and target genes of Rel/NF-kappaB transcription factors," Oncogene, vol. 18, pp. 6853-6866 (1999).

Palanki, M.S., "Inhibitors of AP-1 and NF-κB Mediated Transcriptional Activation: Therapeutic Potential in Autoimmune Diseases and Structural Diversity," CURR> Med. Chem, vol. 9, pp. 219-227 (2002).

Palanki, M.S. et al., Structure-activity relationship studies of ethyl 2-[(3-methyl-2,5-dioxo(3-pyrrolinyl))amino]-4-(trifluoromethyl)pyrimidine-5-carboxylate: an inhibitor of AP-1 and NF-kappaB mediated gene expression Bioorg Med Chem Lett, vol. 12, pp. 2573-2577 (2002).

Palanki, M.S., "Interleukin-2 Inhibitors in Autoimmune Disease," Exp. Opin. Ther. Patents, vol. 9, No. 1, pp. 27-39 (1999).

Pillai, A.D. et al., "Design, synthesis, and pharmacological evaluation of some 2-[4-morpholino]-3-aryl-5-substituted thiophenes as novel anti-inflammatory agents: generation of a novel anti-inflammatory pharmacophore," Bioorganic & Medicinal Chemistry, vol. 12, pp. 4667-4671 (2004).

Pilorget, A. et al., Medulloblastoma cell invasion is inhibited by green tea (-) epigallocatechin-3-gallate. J Cell Biochem., vol. 90, pp. 745-755 (2003).

Porter, C.M. et al., Identification of Amino Acid Residues and Protein Kinases Involved in the Regulation of NFATc Subcellular Localization J. Biol. Chem., vol. 275, pp. 3543-3551 (2000).

Rajappa, S. et al., "A General Synthesis of Thiazoles. Part 3. Comparative Evaluation of Different Functionalised Thioureas as Precursors," J. Chem. Soc Perkins Trans, vol. I, pp. 1762-1764 (1979).

Rajasekharan, K.N., "Studies on the Synthesis of 5-Acyl-2,4-diaminothiazoles from Amidinothioureas," Synthesis, pp. 353-355 (1986).

Rao, A. et al., Transcription factors of the NFAT family: regulation and function. Annu Rev Immunol., vol. 15, pp. 707-747 (1997).

Ryseck, R. et al., c-JUN, JUN B, and JUN D differ in their binding affinities to AP-1 and CRE consensus sequences: effect of FOS proteins. Oncogene, vol. 6, pp. 533-542 (1991).

* cited by examiner

THIAZOLE AND THIOPHENE ANALOGUES, AND THEIR USE IN TREATING AUTOIMMUNE DISEASES AND CANCERS

This is the United States national stage of international application PCT/US2007/066068, international filing date Apr. 5, 2007, which claims the benefit of the 7 Apr. 2006 filing date of United States provisional patent application 60/790, 105 and of the 26 Apr. 2006 filing date of United States provisional patent application 60/795,430.

TECHNICAL FIELD

This invention pertains to compounds and methods that are useful in blocking intracellular signal transduction factors, and in preventing or treating inflammation, autoimmune diseases, and cancer.

BACKGROUND ART

Thiazole and thiophene derivatives have been used as therapeutic agents for such things as to treat neurological disorders, migraine, pain, cancer, inflammation, and autoimmune disease. Aminothiazole compounds substituted at 5th position with substituents such as acyl, aroyl, nitro etc. have also been used for these purposes.

There is abundant evidence that T-lymphocytes orchestrate both the initiation and the propagation of the immune response through the secretion of protein mediators known as cytokines and chemokines. Cytokines and chemokines have been implicated in a number of inflammatory diseases. Inappropriate responses of T-lymphocytes have been associated with a range of immune-related diseases, including allergies, autoimmune diseases, asthma, psoriasis, rheumatoid arthritis, and transplant rejections.

Major functions of T lymphocytes include assisting B cells in the production of antibodies, cooperating with macrophages and related cell types to enhance their capacity to destroy microorganisms, acting as antigen-specific cytotoxic cells, and producing a family of cytokines and chemokines that have profound effects on the function of other cell types. The T cell has a highly-evolved specific antigen recognition system. T cells are activated following engagement of the T cell receptor (TCR), and the receipt of additional co-stimulatory signals. There are specific cytokines and growth factors that stimulate T cells to proliferate and differentiate.

Transcription factors regulate inducible gene expression. In activated T cells, transcription factors such as activator protein-1 (IL-1) regulate interleukin-2 (IL-2), IL-3, GM-CSF, and matrix metalloproteinases, while nuclear factor-κB (NF-κB) regulates transcription of the proinflammatory cytokines IL-1, IL-6, IL-8 and tumor necrosis factor α (TNFα). The ability of transcription factors to bind DNA and modulate gene transcription is tightly regulated in normal cells. Signal transduction pathways regulate cellular responses to stress and play a critical role in inflammation.

The AP-1 transcription factor comprises homo- or heterodimer proteins of the leucine zipper family. The leucine zipper family includes Fos (Fra-1, Fra-2, Fos-B, Fos-B2 and c-Fos), and Jun (c-Jun, JunB and JunD). The Jun family of proteins is widely known, and forms both homo-(Jun-Jun) and hetero-(Jun-Fos) dimers. Three mitogen activated kinase pathways (MAP) (ERKs, JNKs and p38) directly up regulate Fos family genes by phosphorylation. It appears that JNK pathways indirectly up regulate c-Jun expression.

The activated AP-1 complex translocates into the nucleus, where it initiates cytokine production. A variety of extracellular signals stimulate AP-1 activity, including tumor promoters, UV irradiation, growth factors, cytokines, neurotransmitters, and Ras oncoprotein.

The NF-κB transcription factor belongs to Rel family of proteins, which primarily comprises homo- and heterodimeric proteins. The most commonly found combinations are p50/p65 heterodimers and p50/p50 homodimers. NF-κB is normally present in the cytoplasm in an inactive form, bound to inhibitory kappa B (IκB) protein. Several extracellular stimuli such as TNFα, IL-1, certain mitogens and stress factors activate the signaling pathway leading to IκB kinase (IKK), which phosphorylates IκB. Phosphorylated IκB undergoes degradation by 26S proteosome, releasing NF-κB, which translocates to the nucleus and initiates transcription.

Nuclear factor of activated T cells (NFAT) transcription factors playa critical role in transcriptional regulation of IL-2, IL-3, IL-4, IL-5, IL-8, IL-13, TNFα, and GM-CSF. NFAT proteins are expressed in T cells, B cells, NK cells, mast cells, macrophages, and endothelial cells. NFAT's nuclear functions are regulated by cooperative interactions with AP-1. When certain ligands bind to receptors such as Fcg receptors on macrophages and NK cells, the histamine and thrombin G protein coupled receptors on endothelial cells, and Fce receptors on mast cells and basophils, phospholipase C is activated and inositol triphosphate (IP3) is generated. Calcium is then mobilized, and calcium- and calmodulin-dependent phosphatase calcineurin are activated. Calcineurin regulates the localization and transcriptional function of NFAT via dephosphorylation. Several kinases, including JNK, ERK, and p38, inhibit NFAT activation via phosphorylation at the NFAT regulatory domain where calcineurin binds.

Since many diseases are caused by the inappropriate production of proteins, many prior therapies have focused on inhibiting the function or activity of individual effector proteins. These treatments have not always proved effective, and have sometimes been associated with undesirable side effects.

There is an unfilled need for new compounds to treat inflammation, autoimmune diseases, and cancers. There is an unfilled need for compounds that will inhibit the transcription of one or more of AP-1, NF-κB, and NFAT transcriptional activation in T cells. Each of these transcription factors is regulated by a distinct signaling pathway involving several proteins including different kinases. There is an unfilled need for compounds that also inhibit the kinase(S) that regulates the activation of the transcription factors AP-1, NF-κB, and NFAT.

Transcriptional Inhibitors, Post-transcriptional Inhibitors, and Multi-Pathway Inhibitors for Cancer Treatment Most current anticancer treatments and drug discovery programs focus on targeting a single gene (for example, her2/neu or VEGF) or a single pathway (for example, kinase activation). However, cancer is a multifactor process involving the expression of many different proteins. This is reflected in the observation that many current clinical trials involve combinations of different drugs. A significant drawback to combined therapies is that each drug typically has its own associated side effects, and the combination of multiple drugs can lead to an increase in the number or intensity of side effects. There is an unfilled need for single compounds that can act upon multiple pathways and targets involved in cancers, for example, single compounds that can act against angiogenesis, growth, and metastasis, processes which involve diverse proteins (for example, VEGF, her2/neu receptor, and matrix metalloproteases, respectively). Classical drug discovery approaches, targeting each protein separately, are unlikely to find single compounds that serendipitously act upon other targets and pathways. There is an unfilled need for single compounds to inhibit the production of different proteins involved in different pathways.

U.S. Pat. No. 6,630,589 discloses screens for identifying small molecules capable of preventing the production of proteins at the post-transcriptional level, and discloses a small molecule that blocked her2/neu protein synthesis. Although the precise mechanism of action of this molecule was not elucidated, it may involve translational regulation. The regulation of other poorly translated proteins in cancer may be due to increased levels of the cap binding protein, eIF4E, which is often found in cancer cells, and the levels of which have been correlated with clinical recurrence. There is an unfilled need for compounds to target highly cap-dependent translation pathways, as such compounds could affect many genes involved in cancer growth and progression with reduced effects on normal cells.

Transcriptional regulation also plays an important role in the production of proteins involved in cancers; for example, NF-κB- and AP-1-inducible genes are targets for the development of anticancer agents. There is an unfilled need for single compounds that selectively inhibit the expression of multiple genes involved in cancers. There is an unfilled need for small molecules for treating cancers. Many current clinical trials involve relatively large molecules, such as monoclonal antibodies, recombinant proteins, peptide vaccines, siRNAs, and antisense RNA. While many of these approaches have shown promise, particularly monoclonal antibodies and recombinant proteins, they typically require injection and are usually expensive. Peptide vaccines and siRNAs are still in early stages of development, but would presumably also require injections and be expensive. Gene therapy and antisense strategies have had more failures than successes.

The usual approach in mechanism-based drug discovery is first, to optimize molecular properties against a single target, and then, to modify the molecule to have better "drug-like" properties. However, cancer is a complex disease that results from perturbations in as many as six different intracellular regulatory systems. A drug that affects a single target or pathway may therefore not be very effective against the heterogeneous distribution of cellular phenotypes that is typical of most cancers. The individual compounds of this invention affect multiple targets and pathways. Given the diversity of the proteins involved in different pathways, the conventional drug discovery approach, targeting a particular protein, is unlikely to develop single compounds to affect multiple pathways. The novel compounds instead prevent the production of critical proteins in multiple pathways by targeting transcriptional or post-transcriptional regulatory processes.

General transcriptional inhibitors, those affecting transcription of all mRNA, would be too toxic. Inhibition of specific transcriptional factors is desirable. NF-κB and AP-1 are the targets for the novel anti-cancer therapeutics. NF-κB and AP-1 pathways play an important role in promoting metastases, tumor progression, angiogenesis, and chemoresistance. Many genes involved in cancer (e.g., IL-6, IL-8, MMP-9, COX-2, and MCP-1) are regulated by the combined action of NF-κB and AP-1. Activated AP-1 and NF-κB are found in transformed keratinocytes, pancreatic cancers, and head and neck squamous cell carcinoma cell lines.

Inhibition of NF-κB and AP-1 by various natural products, including macrolides, endovanilloids, and EGCG has been demonstrated to have anti-inflammatory effects. EGCG has been studied for anticancer activities. Curcumin, derived from the plant *Curcuma longa*, has been demonstrated to down-regulate NF-κB and AP-1, and is also being studied as an anticancer agent. While existing work with these compounds demonstrates that inhibitors of NF-κB and AP-1 can be useful as anti-cancer agents, natural products can be costly to purify and usually are not very potent, requiring high dosages to elicit substantial anti-cancer activity. Structural modification and formulation of these natural products is a possibility in principle, but has proven to be challenging in practice. Other genes that are involved in angiogenesis and tumor growth are constitutively transcribed and regulated at the translational level in cancer cells. Thus targeting NF-κB and AP-1 alone may not inhibit many of the critical targets in cancer growth and metastasis.

The translation initiation factors eIF4E, eIF4F, and eIF4G, and mTOR have been shown to play a significant role in tumor progression. The factor eIF4E is elevated in most human breast and head and neck cancers, and its overexpression has been correlated with elevated angiogenic growth factors and by hypoxia. In head and neck tumors, elevated eIF4E levels have been associated with increased levels of VEGF, FGF-2, microvessel density, and poor outcome. In breast cancer, high eIF4E levels have also been associated with poor clinical outcome.

DISCLOSURE OF THE INVENTION

We have discovered new compounds that block the activation of one or more transcription factors (TFs), particularly NF-κB, AP-1, and NFAT. Without wishing to be bound by this hypothesis, we believe that the compounds act by inhibiting a family of specific kinases. Administering the novel compounds causes a decrease in one or more specific proinflammatory proteins, including Il-1, IL-2, Il-8, and TNF-α, which have been associated with tissue and organ damage in diseases such as rheumatoid arthritis, osteoarthritis, other autoimmune disorders, transplant rejection, and cancers. The compounds of the present invention are useful in treating these conditions, and more generally are useful as anti-inflammatory agents. The novel compounds may be administered by injection, and in many cases may be administered orally, a distinct advantage over most existing treatments, which usually require injection.

While it would seem extremely unlikely that a single agent could inhibit all three of these important, yet diverse, pathways leading to protein production, we have, in two different cell lines, identified at least four compounds (designated PMCR112 (example 225), PMCR 147 (example 244), PMCH24 (example 116), and PMCH16 (example 134)) that are capable of inhibiting both NF-κB and also highly cap-dependent translation. These four compounds and their analogs offer the potential for potent, safe, small molecule inhibitors of several proteins that are critical to the progression, growth and metastasis of breast cancer, other cancers, and inflammation.

The novel small molecule, multipathway inhibitors target many of the same genes that are targeted by other therapies that are currently in clinical trials, while having better bioavailability and being less expensive to produce.

The novel compounds are thiazole or thiophene derivatives. Methods for the synthesis of these compounds are also considered to be within the scope of this invention. The compounds have the following general structure I, as described more specifically below.

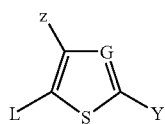

We have developed a NF-κB/AP-1 translation screen in HEK293 cells. We have also developed a highly cap-dependent translation screen in FaDu cells. Both screening systems can, for example, use a luciferin-luciferase system as an indicator. In addition, we have used a previously-developed screen involving the post-transcriptional regulatory element ARE of TNF-α to screen for anti-inflammatory and anti-cancer activity.

MODES FOR CARRYING OUT THE INVENTION

Figure 1:
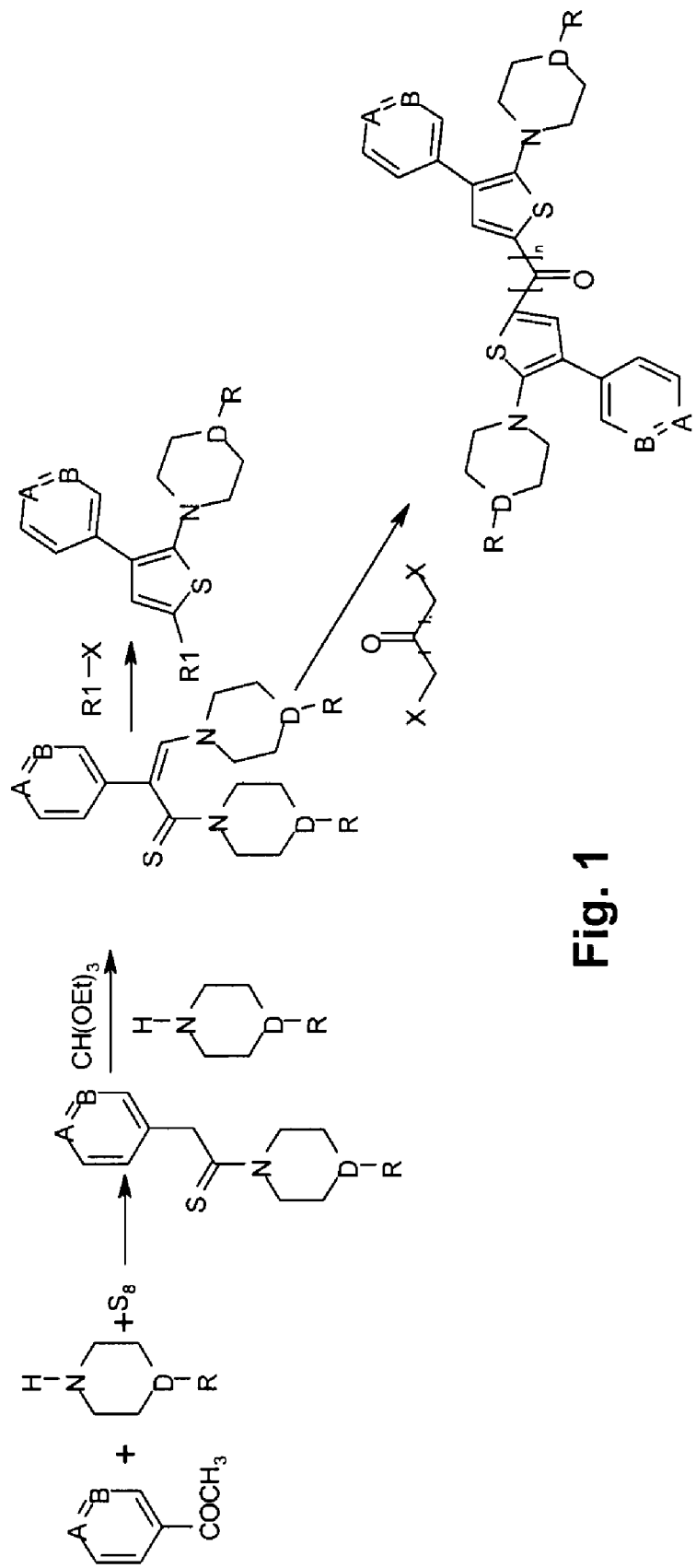
FIG. 1 depicts a generic scheme for the synthesis of a group of compounds within the scope of this invention.
Figure 2:
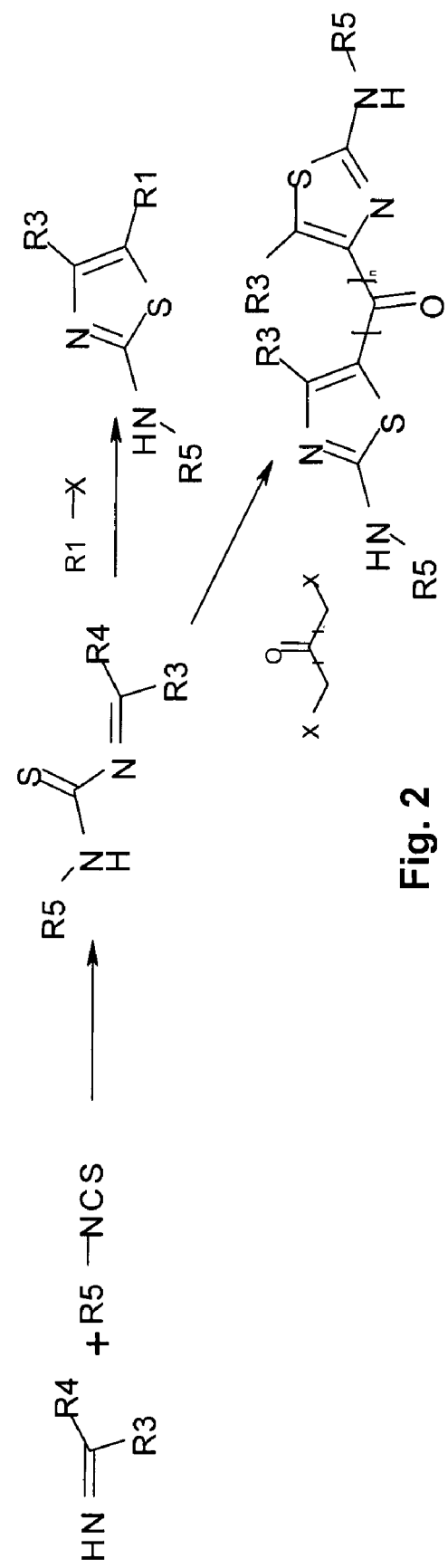
FIG. 2 depicts a generic scheme for the synthesis of a group of compounds within the scope of this invention.
Figure 3:
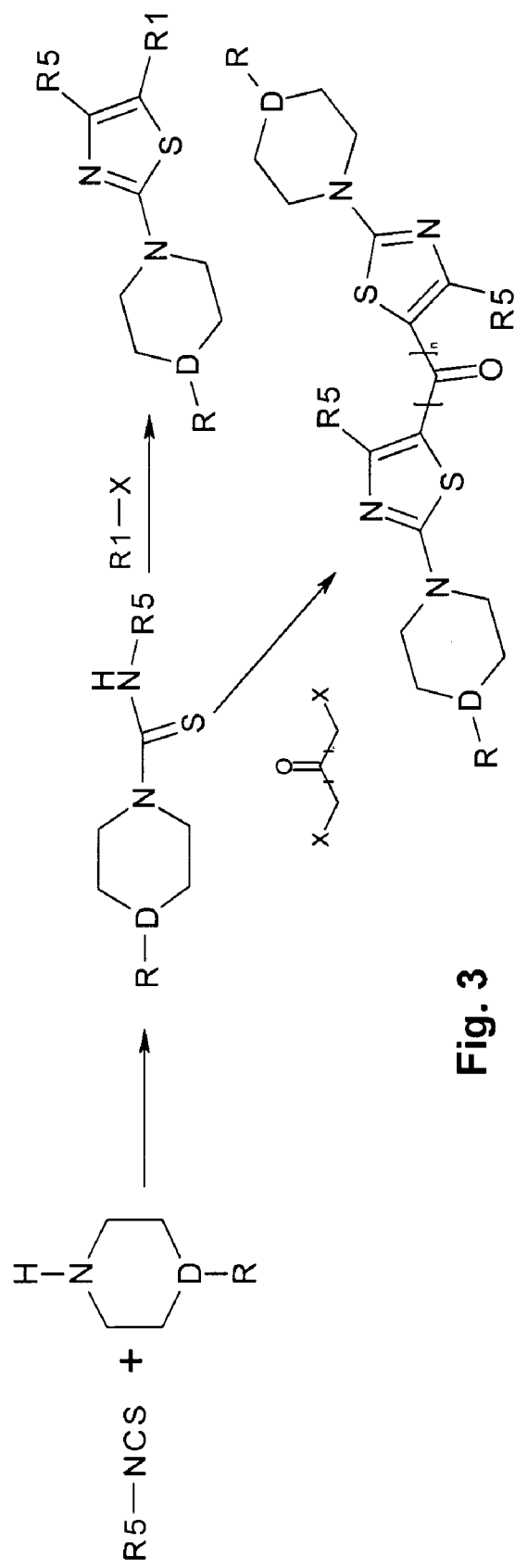
FIG. 3 depicts a generic scheme for the synthesis of a group of compounds within the scope of this invention.
Figure 4:
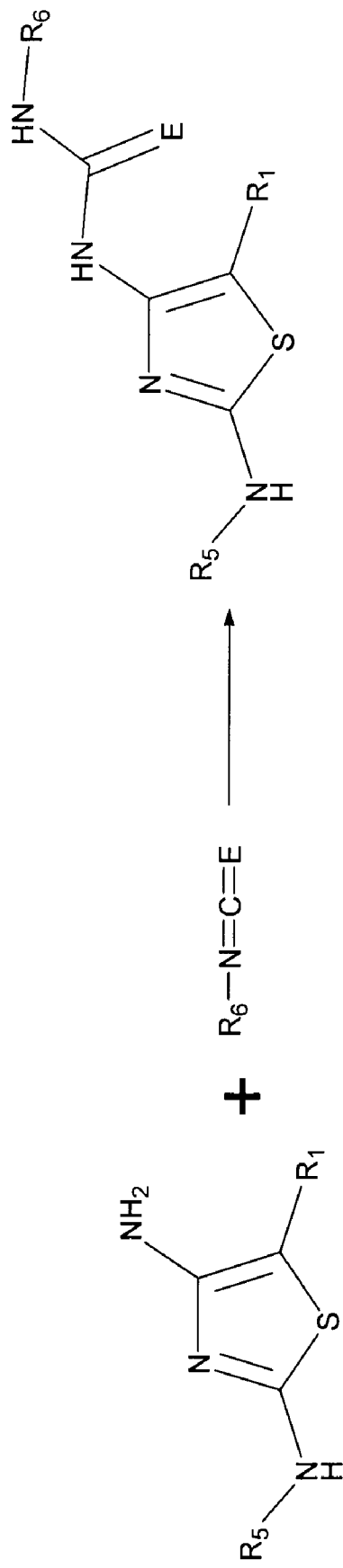
FIG. 4 depicts a generic scheme for the synthesis of a group of compounds within the scope of this invention.
Figure 5:
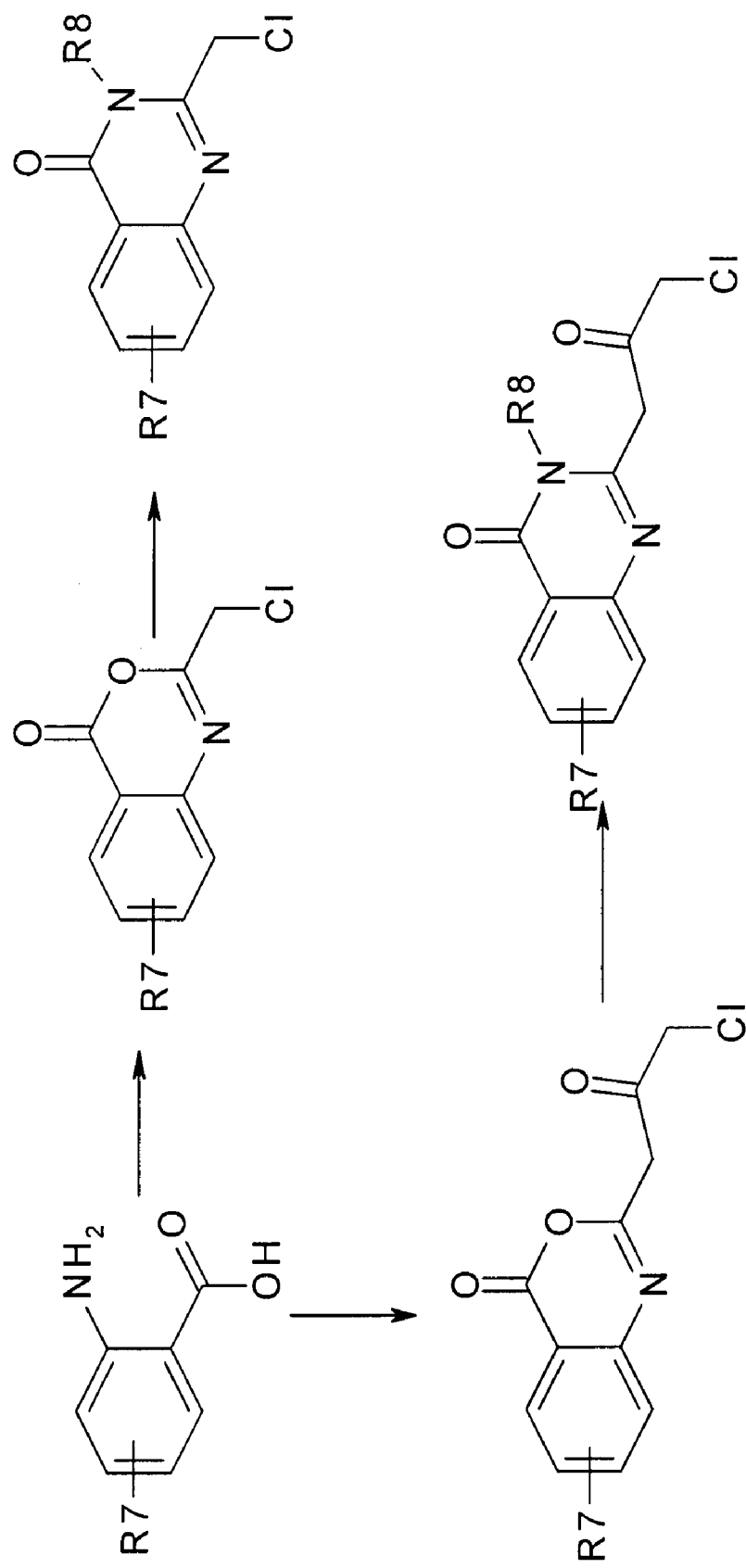
FIG. 5 depicts a generic scheme for the synthesis of a group of compounds within the scope of this invention.

Without wishing to be bound by this hypothesis, it is believed that the novel compounds function by inhibiting the kinase(s) that regulate the activation of TFs, such as NF-κB or AP-1. By disrupting the production of the activated TFs, the synthesis of pathological proteins is blocked at the transcription level, including proinflammatory cytokines associated with inflammation, autoimmune diseases and cancers. The compounds of this invention have activity in both preventing and treating inflammatory diseases such as rheumatoid arthritis, osteoarthritis and transplant rejection (tissue and organ), autoimmune diseases (e.g., multiple sclerosis and asthma), and cancers.

Compounds that may be used in this invention include those having one of the following general structures:

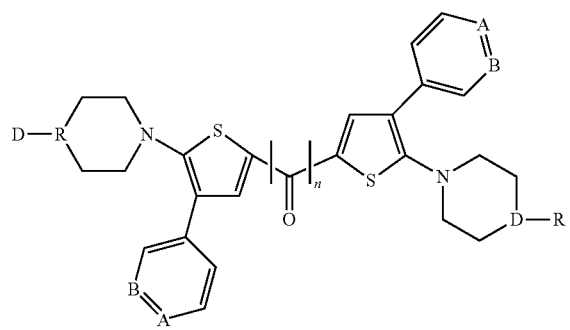

wherein:
A=C(R$_2$) or N
B=CH or N
D(R)=CH$_2$ or O or N(R)
R=H, or substituted or unsubstituted C$_{1-4}$ alkyl, aryl, aroyl, heteroaryl, or heteroaroyl
R$_1$=substituted or unsubstituted aryl, aroyl, heteroaryl, heteroaroyl, C$_{1-4}$ alkoximino, or C$_{1-8}$ esters
X=chloro or bromo
R$_2$=—H, or -chloro, -fluoro, -bromo, —CH$_3$, —OCH$_3$, —NHCOCH$_3$, —SCH$_3$, SO$_2$CH$_3$, —SOCH$_3$, CF$_3$, or NH$_2$
n=1 or 2
R$_3$=—CH$_3$, —C$_2$H$_5$, —NH$_2$, or substituted or unsubstituted aryl or heteroaryl, or —NMe$_2$
R$_4$=—NEt$_2$, —NMe$_2$, or —NH$_2$
R$_5$=substituted or unsubstituted aryl, heteroaryl, aroyl, heteroaroyl, —COOCH$_3$, —COOC$_2$H$_5$, —COOaryl, or —COOheteroaryl
R$_6$=substituted or unsubstituted aryl or heteroaryl
E=O or S These expressions should be given their common meaning as understood by those in the art. For example, "C$_{1-4}$ alkyl" should be interpreted to include methyl, ethyl, propyl, isopropyl, butyl, s-butyl, and isobutyl.

As another example, "heteroaryl" means an aryl group with one or more heteroatom substitutions, such as mono or disubstitutions with halogen atoms such as chlorine, fluorine, and bromine; or methoxy; or methyl, or trifluoromethyl; or amino.

As another example, "aroyl" refers to the radical of an aromatic acid, e.g., benzoyl.

As another example, "substituted" refers to common substituents including mono- or di- or tri-substitutions with moieties such as trifluoromethoxy, methoxy, chlorine, bromine, fluorine, methyl, methoxy, pyridyl, furyl, triazyl, piperazinyl, pyrazoyl, imidazoyl, and the like. There may be further substitutions, such as piperazines having alkyl or aryl substitution, or thiazole and thiophene derivatives with heteroaryl, wherein R$_1$ has one of the structures as those shown below:

wherein:
R$_7$=—H or —Br
R$_8$=Aryl or heteroaryl

Thiophene derivatives were prepared by the following procedure: The first step was the Willgerodt-Kindller reaction. In the second step, the reaction mixture was treated with triethylorthoformate and morpholine to produce an enamine, which on further treatment with an activated chloromethanone or activated chloromethane compound gave the desired thiophene derivative.

Thiazole derivatives were prepared by the following procedure: Nitriles were converted into amidines or guanidine and then treated with isothiocynates to obtain thiourea derivatives, followed by treatment with an activated chloromethanone or activated chloromethane to obtain the desired thiazole derivative.

EXAMPLES

The initial examples below describe the syntheses of representative compounds of this invention, and their intermediates. Those examples are followed by examples of in vivo assays, and experimental data showing the activity of various compounds.

Abbreviations: "M.P."=melting point. "LC MS"=liquid chromatography/mass spectrometry. "Rf"=retention factor

Example 1

1-Morpholin-4-yl-2-phenyl-ethanethione

A solution of acetophenone (10.0 gm; 0.083 mol); sulphur (2.65 gm; 0.083 mol); and Morpholine (7.22 gm; 0.083 mol) with a catalytic amount of p-toluenesulphonic acid monohydrate refluxed 6 hour at 120° C. Then the mixture was poured into methanol (75 ml) and cooled at −20° C. for 6 hr. Precipitates were filtered out and washed with cold methanol (50 ml). Yield 7.5 gm (40.7%) M.P. 115-116° C. LC MS: 221 (M+1), Rf: 0.49, Mobile phase: acetonitrile:toluene 3:7.

Example 2

2-(4-Methanesulfonyl-phenyl)-1-morpholin-4-yl-ethanethione

The title compound was prepared from 1-(4-methanesulfonyl-phenyl)-ethanone (10.0 gm; 0.051 mol) as otherwise described in Example 1. Yield 9.0 gm (60%) M.P. 198-199° C., Rf: 0.56, LC MS: 300 (M+1).

Example 3

N-[4-(2-morpholin-4-yl-2-thioxo-ethyl)-phenyl]-acetamide

The title compound was prepared from N-(4-acetyl-phenyl)-acetamide (10.0 gm; 0.056 mol) as otherwise described in example 1. Yield 8.0 gm (50.72%) M.P. 210-212° C., Rf: 0.46, LC MS: 279 (M+1).

Example 4

2-(4-Chloro-phenyl)-1-morpholin-4-yl-ethanethione

The title compound was prepared from 1-(4-chloro-phenyl)-ethanone (10.0 gm; 0.065 mol) as otherwise described in Example 1. Yield 10.0 gm (60.15%) M.P. 175-177° C., Rf: 0.68, LC MS: 254.5 and 256.5 (M+2).

Example 5

1-Morpholin-4-yl-2-pyridine-3-yl-ethanethione

The title compound was prepared from 1-pyridine-3yl-ethanone (10.0 gm; 0.082 mol) as otherwise described in Example 1. Yield 8.0 gm (48.39%) M.P. 158-160° C., Rf: 0.58 LC MS: 223 (M+1).

Example 6

1-Morpholin-4-yl-2-pyridine-4-yl-ethanethione

The title compound was prepared from 1-pyridine-4-yl-ethanone (10.0 gm; 0.082 mol) as otherwise described in Example 1. Yield 7.68 gm (47.39%) M.P. 162-163° C., Rf: 0.41, LC MS: 223 (M+1).

Example 7

2-(4-Methanesulfanyl-phenyl)-1-morpholin-4-yl-ethanethione

The title compound was prepared from 1-(4-methylsulfanyl-phenyl)-ethanone (10.0 gm; 0.082 mol) as otherwise described in Example 1. Yield 9.0 gm (60%) M.P. 225-227° C., Rf: 0.48, LC MS: 268 (M+1).

Example 8

2-(4-Methanesulfonyl-phenyl)-1-(4-methyl-piperazine-1-yl)-ethanethione

The title compound was prepared from 1-(4-methylsulfonyl-phenyl)-ethanone (10.0 gm; 0.051 mol) and 1-Methyl-piperazine (5.0 gm; 0.051 mol) as otherwise described in Example 1. Yield 9.0 gm (56.70%) M.P. 172-177° C., Rf: 0.59, LC MS: 313 (M+1).

Example 9

1-Morpholin-4-yl-2-p-tolyl-ethanethione

The title compound was prepared from 1-p-tolyl-ethanone (10.0 gm; 0.075 mol) as otherwise described in Example 1. Yield 10.0 gm (56.91%) M.P. 182-185° C., Rf: 0.64, LC MS: 236 (M+1).

Example 10

2-(4-Methoxy-phenyl)-1-morpholin-4-yl-ethanethione

The title compound was prepared from 1-(4-methoxy-phenyl)-ethanone (10.0 gm; 0.067 mol) as otherwise described in Example 1. Yield 10.0 gm (56.91%) M.P. 145-147° C., Rf: 0.65, LC MS: 252 (M+1).

Example 11

(Z)-1,3-Di-morpholin-4-yl-2-phenyl-propenethione

A mixture of 1-morpholin-4-yl-2-phenyl-ethanethione (5.0 gm; 0.023 mol) and morpholine (1.92 gm; 0.023 mol) and triethyl orthoformate (25 ml) was refluxed for 18 hr. The reaction mixture was then evaporated under reduced pressure and poured into methanol (25 ml) and cooled at −20° C. for 6 hr. The precipitate was filtered out and dried. Yield 3.6 gm (50%). M.P. 152-154° C., Rf: 0.62, LC MS: 319 (M+1).

Example 12

(Z)-2-(4-Methanesulfonyl-phenyl)-1,3-dimorpholine-4-yl-propenethione

The title compound was prepared from 2-(4-methanesulfonyl-phenyl)-1-morpholin-4-yl-ethanethione (5.0 gm; 0.013 mol) as otherwise described in Example 11. Yield 5.0 gm (75.51%) M.P. 167-169° C. Rf: 0.25, LC MS: 397 (M+1).

Example 13

N-{4-[(Z)-1-(Morpholine-4-carbothioyl)-2-morpholin-4-yl-vinyl]-phenyl}-acetamide The title compound was prepared from N-[4-(2-morpholin-4-yl-2-thioxo-ethyl)-phenyl]-acetamide (5.0 gm; 0.018 mol) as otherwise described in Example 11. Yield 4.0 gm (59.26%) M.P. 145-147° C. Rf: 0.36, LC MS: 376 (M+1).

Example 14

(Z)-2-(4-Chloro-phenyl)-1,3-dimorpholin-4-yl-propenethione

The title compound was prepared from 2-(4-chloro-phenyl)-1-morpholin-4-yl-ethanethione (5.0 gm; 0.020 mol) as otherwise described in Example 11. Yield 5.40 gm (72.00%) M.P. 134-135° C. Rf: 0.54, LC MS: 352.5 (M+2).

Example 15

(Z)-1,3-Dimorpholin-4-yl-2-pyridin-3-yl-propenthione

The title compound was prepared from 1-morpholin-4-yl-2-pyridine-3-yl-ethanethione (5.0 gm; 0.023 mol) as otherwise described in Example 11. Yield 3.6 gm (46.23%) M.P. 133-135° C., Rf: 0.65, LC MS: 320 (M+1).

Example 16

(Z)-1,3-Dimorpholin-4-yl-2-pyridin-4-yl-propenthione

The title compound was prepared from 1-morpholin-4-yl-2-pyridine-4-yl-ethanethione (5.0 gm; 0.023 mol) as otherwise described in Example 11. Yield 3.0 gm (39.68%) M.P. 122-125° C., Rf: 0.49, LC MS: 320 (M+1).

Example 17

(Z)-2-(4-Methanesulfanyl-phenyl)-1,3-dimorpholine-4-yl-propenethione

The title compound was prepared from 2-(4-methanesulfanyl-phenyl)-1-morpholin-4-yl-ethanethione (5.0 gm; 0.013 mol) as otherwise described in Example 11. Yield 5.0 gm (75.51%) M.P. 189-190° C., Rf: 0.38, LC MS: 366 (M+1).

Example 18

(E)-2-(4-Methanesulfonyl-phenyl)-1,3-bis-(4-methyl-piperazin-1-yl)-propenethione The title compound was prepared from 2-(4-methanesulfonyl-phenyl)-1-(4-methyl-piperazine-1-yl)-ethanethione (5.0 gm; 0.016 mol) as otherwise described in Example 11. Yield 3.4 gm (59.51%) M.P. 202-203° C., Rf: 0.58, LC MS: 423 (M+1).

Example 19

(Z)-1,3-Dimorpholin-4-yl-2-p-tolyl-propenethione

The title compound was prepared from 1-morpholin-4-yl-2-p-tolyl-ethanethione (5.0 gm; 0.015 mol) as otherwise described in Example 11. Yield 3.6 gm (53.82%) M.P. 212-213° C., Rf: 0.72, LC MS: 334 (M+1).

Example 20

(Z)-2-(4-Methoxy-phenyl)-1,3-dimorpholin-4-yl-propenethione

The title compound was prepared from 2-(4-methoxy-phenyl)-1-morpholin-4-yl-ethanethione (5.0 gm; 0.020 mol) as otherwise described in Example 11. Yield 3.8 gm (54.83%) M.P. 112-113° C., Rf: 0.32, LC MS: 350 (M+1).

The above intermediates may be used in the preparation of thiophene analogs. Intermediates for preparing thiazole analogs may be made as described below, as in Example 21.

Example 21

(General Procedure)

To a solution of isothiocyanate (0.0368 moles) in toluene was added N,N-diethyl acetamidine (0.0368 moles) in toluene at 0° C. in 10 min. The reaction mixture was stirred for 2 hours at 25°. The precipitate was filtered and washed with hexane to give the desired adduct.

Example 22

({[(1E)-1-(Diethylamino)methylidene]amino}carbonothioyl)carbamate

The title compound was made as otherwise described in Example 21 as a white solid. (91% yield) M.P. 119° C. Rf: 0.58 (Dichloromethane:Ethyl acetate: 1:0.3), IR (KBr, cm$^{-1}$): 3170, 3080, 2970, 2930, 1736, 1656, 1568, 1544, 1476, 1464, 1448, 1348, 1296, 1276, 1192, 1140, 1096, 1072, 1028, 952, 780, 744, 712, 616, Mass (LC-MS, M+1): 246

Example 23

({[(1E)-1-(Diethylamino)ethylidene]amino}carbonothioyl)carbamate

The title compound was made as otherwise described in Example 21 as a white solid. (85% yield) M.P. 109° C., Rf: 0.55 (Dichloromethane:Ethyl acetate: 1:0.3) IR (KBr, cm$^{-1}$): 3120, 3095, 2980, 2920, 1741, 1654, 1558, 1540, 1480, 1448, 1333, 1290, 1276, 1096, 1072, 952, 786, 750. Mass (LC-MS, M+1): 232.

Example 24

1-[1-Diethylamino-eth-(E)-ylidene]-3-methyl-thiourea

The title compound was made as otherwise described in Example 21 as white crystals (56% yield) M.P. 133-134° C., Rf: 0.58 (Dichloromethane:Ethyl acetate 1:0.3), IR (KBr, cm$^{-1}$): 3180, 3110, 3000, 2950, 1590, 1520, 1500, 1476, 1428, 1372, 1352, 1316, 1280, 1244, 1220, 1175, 1148, 1100, 1084, 1048, 1024, 1004, 960, 896, 848, 832, 795, 756, 716, 700, 608, Mass (LC-MS, M+1): 250

Example 25

1-Benzoyl-3-[1-diethylamino-eth-(E)-ylidene]-thiourea

The title compound was made as otherwise described in Example 21 as yellow crystals, (58% Yield) M.P. 111-112° C. Rf: 0.75 Dichloromethane:Ethyl acetate (1:0.3) IR (KBr, cm$^{-1}$): 3190 (br), 2970, 2940, 1688, 1576, 1548, 1492, 1480, 1452, 1376, 13604, 1336, 1284, 1264, 1208, 1144, 1076, 1016, 880, 800, 712, 688, 660, Mass (LC-MS, M+1): 278.

Example 26

1-(4-Chloro-phenyl)-3-[1-diethylamino-eth-(E)-ylidene]-thiourea

The title compound was made as otherwise described in Example 21 as white crystals (86.8% yield). M.P. 149-150° C. Rf: 0.63 (Dichloromethane:Ethyl acetate: 1:0.3), IR (KBr, cm$^{-1}$): 3170 (br), 3090, 3000, 2940, 1596, 1584, 1524, 1492, 1424, 1372, 1352, 1312, 1280, 1240, 1176, 1148, 1088, 1008, 844, 816, 788, 724. Mass (LC-MS, M+, M+2): 284, 286.

Example 27

({[(1E)-(Diethylamino) (phenyl)ethylene]amino}carbonothioyl)carbamate

The title compound was made as otherwise described in Example 21 as a light yellow solid Yield: 80%, Melting point: 114-116° C., Rf: 0.32 (Toluene: acetonitrile 0.8:0.2), IR (KBr, cm$^{-1}$): 3178, 2978, 1745, 1577, 1515, 1335, 1287, 1207, 1153, 1095, 1032, 787, 769, 689, $^1$H NMR (400 MHz, CDCl$_3$) δ [ppm]=1.2 (t, 3H, OCH$_2$—CH$_3$); 1.3 (t, 3H, —N—CH$_2$—CH$_3$); 1.5 (t, 3H, —N—CH$_2$—CH$_3$); 3.2-3.4 (q, 2H, —N—CH$_2$—CH$_3$); 3.6-3.7 (q, 2H, —N—CH$_2$—CH$_3$); 4.1-4.3 (q, 2H, OCH$_2$—CH$_3$); 7.2-7.4 (m, 5H, C$_6$H$_5$); 8.1 (S, 1H, NH), LCMS (M+1): 308.

Example 28

({[(E)-(Diethylamino)(phenyl)methylenze]amino}carbonothioyl)carbamate

The title compound was made as otherwise described in Example 21. as light yellow solid % Yield: 85, Melting point: 118-119° C., Rf: 0.32 (Toluene:Acetonitrile 0.7:0.3) IR (KBr, cm$^{-1}$): 3178, 2983, 1745, 1571, 1529, 1339, 1288, 1208, 1096, 1153, 1042, 1041, 770, 716, 682, $^1$H NMR (400 MHz, CDCl$_3$) δ [ppm]=1.3-1.4 (t, 3H, —N—CH$_2$—CH$_3$; 1.5-1.6 (t, 3H, —N—CH$_2$—CH$_3$); 3.2-3.4 (q, 2H, —N—CH$_2$—CH$_3$); 3.6-3.7 (q, 2H, —N—CH$_2$—CH$_3$); 3.8 (S, 3H, OCH$_3$); 7.2-7.4 (m, 5H, C$_6$H$_5$); 8.1 (S, 1H, NH), LCMS (M+1): 294

Example 29

1-[1-Diethylamino-1-phenyl-meth-(E)-ylidene]-3-methyl-thiourea

The title compound was made as otherwise described in Example 21, as a white solid Yield: 45%, Melting point: 54-56° C., Rf: 0.37 (Toluene:Acetonitrile 0.7:0.3), LCMS (M+1): 242

Example 30

1-Benzoyl-3-[1-diethylamino-1-phenyl-meth-(E)-ylidene]-thiourea

The title compound was made as otherwise described in Example 21 as a white solid Yield: 59%, M.P. 135-137° C., Melting point: 138-140° C., Rf: 0.31 (Dichloromethane), IR (KBr, cm$^{-1}$): 3180, 2990, 2930, 1584, 1536, 1508, 1428, 1336, 1308, 1276, 1236, 1208, 1188, 1144, 1088, 1064, 1020, 996, 948, 912, 884, 836, 780, 764, 744, 688, 640, $^1$H NMR (400 MHz, CDCl$_3$) δ [ppm]=1.1-1.3 (t, 3H, —N—CH$_2$—CH$_3$); 1.4-1.6 (t, 3H, —N—CH$_2$—CH$_3$); 3.2-3.4 (q, 2H, —N—CH$_2$—CH$_3$); 3.6-3.8 (q, 2H, —N—CH$_2$—CH$_3$); 7.2-7.4 (m, 10H, C$_6$H$_5$, C$_6$H$_5$)); 8.2 (S, 1H, NH, LC-MS, M+1: 312.

Example 31

1-[1-Diethylamino-1-phenyl-meth-(E)-ylidene]-3-phenyl-thiourea

The title compound was made as otherwise described in Example 21. Yield: 56%, M.P. 110-112° C. Rf: 0.35 (Dichloromethane), $^1$H-NMR (400 MHz, CDCl$_3$) δ [ppm]=1.1-1.3 (t, 3H, —N—CH$_2$—CH$_3$); 1.4-1.6 (t, 3H, —N—CH$_2$—CH$_3$; 3.2-3.4 (q, 2H, —N—CH$_2$—CH$_3$); 3.6-3.8 (q, 2H, —N—CH$_2$—CH$_3$); 7.2-7.4 (m, 10H, C$_6$H$_5$, CO—C$_6$H$_5$)); 9 (S, 1H, NH), LCMS (M+1): 340.

Example 32

1-(4-Chloro-phenyl)-3-[1-diethylamino-1-phenyl-meth-(E)-ylidene]-thiourea

The title compound was made as otherwise described in Example 21. Yield: 74%, Melting point: 138-140° C., Rf: 0.41 (Toluene: Acetonitrile 0.7:0.3), IR (KBr, cm$^{-1}$: 3222, 2983, 1564, 1518, 1489, 1343, 1314, 1301, 1286, 1236, 1147, 1090, 1072, 823, 697, $^1$H-NMR (400 MHz, CDCl$_3$) δ [ppm] =1.1-1.3 (t, 3H, —N—CH$_2$—CH$_3$); 1.4-1.6 (t, 3H, —N—CH$_2$—CH$_3$); 3.2-3.4 (q, 2H, —N—CH$_2$—CH$_3$); 3.6-3.8 (q, 2H, —N—CH$_2$—CH$_3$); 7.2-7.8 (m, 10H, C$_6$H$_5$, C$_6$H$_5$); 8.2 (S, 1H, NH), LCMS (M+1): 346, 348

Example 33

1-[1-Diethylamino-1-phenyl-eth-(E)-ylidene]-3-methyl-thiourea

The title compound was made as otherwise described in Example 21. M.P: 141-143° C., Rf: 0.76, IR (KBr cm$^{-1}$): 3207, 1596, 1559, 1375, 1360, 1314, 1284, 1233, 1145, 1080, 1020, 760, 715, 666. LCMS (M+1): 264

Example 34

1-[1-Diethylamino-1-phenyl-eth-(E)-ylidene]-3-phenyl-thiourea

The title compound was made as otherwise described in Example 21. M.P: 133-135° C., Rf: 0.54 IR (KBr cm$^{-1}$): 3226, 2973, 1589, 1569, 1582, 1469, 1454, 1432, 1340, 1280, 1240, 1193, 1145, 1119, 1074, 1016, 699. LCMS (M+1): 326

Example 35

1-(4-Chloro-phenyl)-3-[1-diethylamino-1-phenyl-eth-(E)-ylidene]-thiourea

The title compound was made as otherwise described in Example 21. M.P: 142-145° C., Rf: 0.42 IR (KBr cm$^{-1}$): 3207, 2934, 1592, 1559, 1489, 1361, 1308, 1279, 1234, 1144, 1088, 1012, 844, 813, 770, 710. LCMS (M+1): 298

Example 36

({[(1E)-(Diethylamino)(benzyl)methylene]amino}carbonothioyl)carbamate

The title compound was made as otherwise described in Example 21. M.P: 165-167° C., Rf: 0.39 IR (KBr cm$^{-1}$): 2994, 1757, 1589, 1562, 1359, 1260, 1226, 1129, 1032, 905, 763, 717. LCMS (M+1): 308

Example 37

({[(1E)-(Diethylamino)(benzoyl)ethylene]amino}carbonothioyl)carbamate

The title compound was made as otherwise described in Example 21. M.P: 120-122° C., Rf: 0.62 IR (KBr cm$^{-1}$): 3192, 2983, 1757, 1591, 1574, 1351, 1275, 1206, 1162, 1135, 1032, 908, 768, 727. LCMS (M+1): 322

Example 38

1-Benzoyl-3-[1-diethylamino-1-phenyl-eth-(E)-ylidene]-thiourea

The title compound was made as otherwise described in Example 21. M.P: 160-163° C., Rf: 0.68, IR (KBr cm$^{-1}$): 3241, 2983, 1689 1504, 1306, 1281, 1246, 1169, 1142, 1126, 787, 686. LCMS (M+1): 354

Example 39

4-[3-Phenyl-5-(4,5,6-trimethoxy-pyridine-2-yl)-thiophen-2-yl]-morpholine (Z)-1,3-Di-Morpholin-4-yl-2-phenyl-propenethione (0.500 gm, 0.0016 moles) and 2-chloroethyl-3,4,5-trimethoxy-pyridine (0.604 gm, 0.0016 moles) were added to acetonitrile (10 ml). The reaction mixture was stirred at room temperature for 24 hour, and then cooled to −20° C. for 6 hr.

The precipitate was separated and washed with cold acetonitrile (5 ml). Yield 57%. LC MS (M+1) 441. Rf: 0.65, M.P: 124° C.

Example 40

4-[5-(Methoxy-4,6-dimethyl-pyridine-2-yl)-3-phenyl-thiophene-2-yl]-morpholine

The title compound was made from (Z)-1,3-di-morpholin-4-yl-2-phenyl-propenethione (0.500 gm, 0.0016 moles) and 2-Chloromethyl-4-methoxy-3,5-dimethyl-pyridine (0.293 gm, 0.0016 moles) as otherwise described in Example 39. Yield 47%. LC MS (M+1) 381, Rf; 0.36 M.P: 136-8° C.

Example 41

4-{5-[5-Methyl-4-(2,2,2-trifluoro-ethoxy)-pyridine-2-yl]-3-phenyl-thiophene-2-yl}-morpholine The title compound was made from (Z)-1,3-di-morpholin-4-yl-2-phenyl-propenethione (0.500 gm, 0.0016 moles) and 2-chloromethyl-5-methyl-4-(2,2,2-trifluoro-ethoxy)-pyridine (0.0016 moles) as otherwise described in Example 39. Yield 32%. LC MS (M+1) 435, Rf; 0.45 M.P: 145-7° C.

Example 42

(5-Morpholin-4-yl-4-phenyl-thiophen-2-yl)-phenyl-methanone

The title compound was made from (Z)-1,3-dimorpholin-4-yl-2-phenyl-propenethione (0.500 gm, 0.0016 moles) and phenacyl bromide (0.0016 moles) as otherwise described in Example 39. Yield 68%. LC MS (M+1) 350, Rf: 0.54 M.P: 184-6° C.

Example 43

(5-Morpholin-4-yl-4-phenyl-thiophen-2-yl)-p-tolyl-methanone

The title compound was made from (Z)-1,3-dimorpholin-4-yl-2-phenyl-propenethione (0.500 gm, 0.016 moles) and p-methylphenacyl bromide (0.0016 moles) as otherwise described in Example 39. Yield 70%. LC MS (M+1) 364. Rf: 0.67, M.P: 198° C.

Example 44

(4-Methoxy-phenyl)-(5-morpholin-4-yl-4-phenyl-thiophene-2-yl)-methanone

The title compound was made from (Z)-1,3-dimorpholin-4-yl-2-phenyl-propenethione (0.500 gm, 0.016 moles) and p-methoxyphenacyl bromide (0.0016 moles) as otherwise described in Example 39. Yield 48%. LC MS (M+1) 380, Rf: 0.61 M.P: 158-9° C.

Example 45

(4-Chloro-phenyl)-(5-morpholin-4-yl-4-phenyl-thiophene-2-yl)-methanone

The title compound was made from (Z)-1,3-di-morpholin-4-yl-2-phenyl-propenethione (0.500 gm, 0.0016 moles) and p-chlorophenacyl bromide (0.0016 moles) as otherwise described in Example 39. Yield 58%. LC MS (M+2) 385, Rf; 0.58, M.P: 187-8° C.

Example 46

(2,4-Dichloro-phenyl)-(5-morpholin-4-yl-4-phenyl-thiophene-2-yl)-methanone

The title compound was made from (Z)-1,3-dimorpholin-4-yl-2-phenyl-propenethione (0.500 gm, 0.0016 moles) and 2,4-dichlorophenacyl bromide (0.0016 moles) as otherwise described in Example 39. Yield 39%. LC MS (M+2) 419, Rf: 0.54, M.P: 198-9° C.

Example 47

(4-Methylsulfanyl-phenyl)-(5-morpholin-4-yl-4-phenyl-thiophene-2-yl)-methanone

The title compound was made from (Z)-1,3-di-morpholin-4-yl-2-phenyl-propenethione (0.500 gm, 0.0016 moles) and 4-methanesulfanylphenacyl bromide (0.0016 moles) as otherwise described in Example 39. Yield 48%. LC MS (M+1) 396. Rf: 0.62, M.P: 165° C.

Example 48

(4-Methylsulfonyl-phenyl)-(5-morpholin-4-yl-4-phenyl-thiophene-2-yl)-methanone

The title compound was made from (Z)-1,3-dimorpholin-4-yl-2-phenyl-propenethione (0.500 gm, 0.0016 moles) and 4-methanesulfonylphenacyl bromide (0.0016 moles) as otherwise described in Example 39. Yield 42%. LC MS (M+1) 426. Rf: 0.63, M.P: 175° C.

Example 49

N-[4-(5-Morpholin-4-yl-4-thiophene-2-carbonyl)-phenyl]-acetamide

The title compound was made from (Z)-1,3-dimorpholin-4-yl-2-phenyl-propenethione (0.500 gm, 0.0016 moles) and 1-[4-(2-Bromo-acetyl)-phenyl]-propan-2-one (0.0016 moles) as otherwise described in Example 39. Yield 36%. LC MS (M+1) 394, Rf; 0.52, M.P: 202-3° C.

Example 50

(5-Morpholin-4-yl-4-phenyl-thiophene-2-yl)-pyridine-3-yl-methanone

The title compound was made from (Z)-1,3-di-morpholin-4-yl-2-phenyl-propenethione (0.500 gm, 0.0016 moles) and 2-bromo-1-pyridin-3yl-ethanone (0.0016 moles) as otherwise described in Example 39. Yield 39%. LC MS (M+1) 351. Rf: 0.69, M.P: 180° C.

Example 51

(5-Morpholin-4-yl-4-phenyl-thiophene-2-yl)-pyridine-4-yl-methanone

The title compound was made from (Z)-1,3-dimorpholin-4-yl-2-phenyl-propenethione (0.500 gm, 0.0016 moles) and 2-bromo-1-pyridin-4-yl-ethanone (0.0016 moles) as otherwise described in Example 39. Yield 38%. LC MS (M+1) 351. Rf: 0.60, M.P: 149° C.

Example 52

4-[3-(4-Methanesulfonyl-phenyl)-5-(5-methoxy-4,6-dimethyl-pyridine-2-yl)-thiophene-2-yl]-morpholine The title compound was made from (Z)-2-(4-methanesulfonyl-phenyl)-1,3-dimorpholine (0.500 gm, 0.0013 moles) and 2-chloromethyl-4-methoxy-3,5-dimethyl-pyridine (0.0013 moles) as otherwise described in Example 39. Yield 48%. LC MS (M+1) 459. Rf: 0.61, M.P: 152° C.

Example 53

4-{3-(4-Methanesulfonyl-phenyl)-5-[5-methyl-5-(2,2,2-trifluoro-ethoxy)-pyridine-2-yl]-thiophene-2-yl}-morpholine The title compound was made from (Z)-2-(4-methanesulfonyl-phenyl)-1,3-dimorpholine (0.500 gm, 0.0013 moles) and 2-chloromethyl-5-methyl-4-(2,2,2-trifluoroethoxy)-pyridine (0.0013 moles) as otherwise described in Example 39. Yield 48%. LCMS (M+1) 513. Rf: 0.59, M.P: 156° C.

Example 54

[4-(4-Methanesulfonyl-phenyl)-5-morpholin-4-yl-thiophene-2-yl]-phenyl-methanone

The title compound was made from (Z)-2-(4-methanesulfonyl-phenyl)-1,3-dimorpholine (0.500 gm, 0.0013 moles) and phenacyl bromide (0.0013 moles) as otherwise described in Example 39. Yield 68%. LC MS (M+1) 428. Rf: 0.67, M.P: 173° C.

Example 55

[4-(4-Methanesulfonyl-phenyl)-5-morpholin-4-yl-thiophene-2-yl]-p-tolyl-methanone The title compound was made from (Z)-2-(4-methanesulfonyl-phenyl)-1,3-dimorpholine (0.500 gm, 0.0013 moles) and p-methylphenacyl bromide (0.0013 moles) as otherwise described in Example 39. Yield 70%. LC MS (M+1) 364. Rf: 0.70, M.P: 189° C.

Example 56

[4-(4-Methanesulfonyl-phenyl)-5-morpholin-4-yl-thiophene-2-yl]-(4-methoxy-phenyl)-methanone The title compound was made from (Z)-2-(4-methanesulfonyl-phenyl)-1,3- dimorpholine (0.500 gm, 0.0013 moles) and p-methoxyphenacyl bromide (0.0013 moles) as otherwise described in Example 39. Yield 48%. LC MS (M+1) 442. Rf: 0.72, M.P: 154° C.

Example 57

(4-Chloro-phenyl)-[4-(4-methanesulfonyl-phenyl)-5-morpholin-4-yl-thiophen-2-yl]-methanone The title compound was made from (Z)-2-(4-methanesulfonyl-phenyl)-1,3-dimorpholine (0.500 gm, 0.0013 moles) and p-chlorophenacyl bromide (0.0013 moles) as otherwise described in Example 39. Yield 58%. LC MS (M+2) 462. Rf: 0.73, M.P: 169° C.

Example 58

(2,4-Dichloro-phenyl)-[4-(4-methanesulfonyl-phenyl)-5-morpholin-4-yl-thiophen-2-yl]-methanone The title compound was made from (Z)-2-(4-methanesulfonyl-phenyl)-1,3-dimorpholine (0.500 gm, 0.0013 moles) and 2,4-dichlorophenacyl bromide (0.0013 moles) as otherwise described in Example 39. Yield 39%. LC MS (M+2) 497. Rf: 0.62, M.P: 170° C.

Example 59

[4-(4-Methanesulfonyl-phenyl)-5-morpholin-4-yl-thiophene-2-yl]-(4-methylsulfanyl-phenyl)-methanone The title compound was made from (Z)-2-(4-methanesulfonyl-phenyl)-1,3-dimorpholine (0.500 gm, 0.0013 moles) and 4-methanesulfanylphenacyl bromide (0.0013 moles) as otherwise described in Example 39. Yield 48%. LC MS (M+1) 474. Rf: 0.42, M.P: 160° C.

Example 60

(4-Methanesulfonyl-phenyl)-[4-(4-methanesulfonyl-phenyl) 5-morpholin-4-yl-thiophene-2-yl]-methanone The title compound was made from (Z)-2-(4-methanesulfonyl-phenyl)-1,3-dimorpholine (0.500 gm, 0.0013 moles) and 4-methanesulfonylphenacyl bromide (0.0013 moles) as otherwise described in Example 39. Yield 42%. LC MS (M+1) 506. Rf: 0.47, M.P: 190° C.

Example 61

N-{4-[4-(4-Methanesulfonyl-phenyl)-5-morpholin-4-yl-thiophene-2carbonyl]-phenyl}-acetamide The title compound was made from (Z)-2-(4-methanesulfonyl-phenyl)-1,3-dimorpholine (0.500 gm, 0.0013 moles) and 1-[4-(2-bromo-acetyl)-phenyl]-propan-2-one (0.0013 moles) as otherwise described in Example 39. Yield 36%. LC MS (M+1) 485. Rf: 0.49, M.P: 129° C.

Example 62

[4-(4-Methanesulfonyl-phenyl)-5-morpholin-4-yl-thiophene-2-yl]-pyridin-3-yl-methanone The title compound was made from (Z)-2-(4-methanesulfonyl-phenyl)-1,3-dimorpholine (0.500 gm, 0.0013 moles) and 2-bromo-1-pyridin-3yl-ethanone (0.0013 moles) as otherwise described in Example 39. Yield 39%. LC MS (M+1) 429. Rf: 0.24, M.P: 122° C.

Example 63

[4-(4-Methanesulfonyl-phenyl)-5-morpholin-4-yl-thiophene-2-yl]-pyridin-4-yl-methanone The title compound was made from (Z)-2-(4-methanesulfonyl-phenyl)-1,3-dimorpholine (0.500 gm, 0.0013 moles) and 2-bromo-1-pyridin-4yl-ethanone (0.0013 moles) as otherwise described in Example 39. Yield 38%. LC MS (M+1) 429. Rf: 0.39, M.P: 128° C.

Example 64

N-{4-[5-(5-Methoxy-4,6-dimethyl-pyridine-2-carbonyl)-2-morpholin-4-yl-thiophene-3-yl]-phenyl}-acetamide The title compound was made from N-{4-[(Z)-1-(morpholine-4-carbothioyl)-2-morpholin-4-yl-vinyl]-phenyl}-acetamide (0.500 gm, 0.0014 moles) and 2-chloromethyl-4-methoxy-3,5-dimethyl-pyridine (0.0014 moles) as otherwise described in Example 39. Yield 48%. LC MS (M+1) 466. Rf: 0.65, M.P: 145° C.

Example 65

N(4-{5-[5-Methyl-4-(2,2,2-trifluoro-ethoxy)-pyridine-2-carbonyl]-2-morpholin-4-yl-thiophen-3-yl}-phenyl)-acetamide The title compound was made from (N-{4-[(Z)-1-(morpholine-4-carbothioyl)-2-morpholin-4-yl-vinyl]-phenyl}-acetamide (0.500 gm, 0.0014 moles) and 2-chloromethyl-5-methyl-4-(2,2,2-trifluoro-ethoxy)-pyridine (0.0014 moles) as otherwise described in Example 39. Yield 48%. LC MS (M+1) 454. Rf: 0.75, M.P: 155° C.

Example 66

N-[4-(5-Benzoyl-2-morpholin-4yl-thiophene-3-yl)-phenyl]-acetamide

The title compound was made from (N-{4-[(Z)-1-(morpholine-4-carbothioyl)-2-morpholin-4-yl-vinyl]-phenyl}-acetamide (0.500 gm, 0.0014 moles) and phenacyl bromide (0.0014 moles) as otherwise described in Example 39. Yield 68%. LC MS (M+1) 437. Rf: 0.89, M.P: 165° C.

Example 67

N-{4-[5-(4-Methyl-benzoyl)-2-morpholin-4-yl-thiophene-3-yl]-phenyl}-acetamide

The title compound was made from (N-{4-[(Z)-1-(morpholine-4-carbothioyl)-2-morpholin-4-yl-vinyl]-phenyl}-acetamide (0.500 gm, 0.0014 moles) and p-methylphenacyl bromide (0.0014 moles) as otherwise described in Example 39. Yield 70%. LC MS (M+1) 421. Rf: 0.69, M.P: 168° C.

Example 68

N-{4-[5-(4-Methoxy-benzoyl)-2-morpholin-4-yl-thiophene-3-yl]-phenyl}-acetamide

The title compound was made from N-{4-[(Z)-1-(morpholine-4-carbothioyl)-2-morpholin-4-yl-vinyl]-phenyl}-acetamide (0.500 gm, 0.0014 moles) and p-methoxyphenacyl bromide (0.0014 moles) as otherwise described in Example 39. Yield 48%. LC MS (M+1) 437. Rf: 0.62, M.P: 198° C.

Example 69

N-{4-[5-(4-Chloro-benzoyl)-2-morpholin-4-yl-thiophene-3-yl]-phenyl}-acetamide

The title compound was made from N-{4-[(Z)-1-(morpholine-4-carbothioyl)-2-morpholin-4-yl-vinyl]-phenyl}-acetamide (0.500 gm, 0.0014 moles) and p-chlorophenacyl bromide (0.0014 moles) as otherwise described in Example 39. Yield 58%. LC MS (M+2) 442. Rf: 0.54, M.P: 120° C.

Example 70

N-{4-[5-(2,4-Dichloro-benzoyl)-2-morpholin-4-yl-thiophene-3-yl]-phenyl}-acetamide The title compound was made from N-{4-[(Z)-1-(morpholine-4-carbothioyl)-2-morpholin-4-yl-vinyl]-phenyl}-acetamide (0.500 gm, 0.0014 moles) and 2,4-dichlorophenacyl bromide (0.0014 moles) as otherwise described in Example 39. Yield 39%. LC MS (M+2) 476. Rf: 0.56, M.P: 145° C.

Example 71

N-{4-[5-(4-Methanesulfanyl-benzoyl)-2-morpholin-4-yl-thiophene-3-yl]-phenyl}-acetamide The title compound was made from N-{4-[(Z)-1-(morpholine-4-carbothioyl)-2-morpholin-4-yl-vinyl]-phenyl}-acetamide (0.500 gm, 0.0014 moles) and 4-methanesulfanylphenacyl bromide (0.0014 moles) as otherwise described in Example 39. Yield 48%. LC MS (M+1) 453. Rf: 0.67, M.P: 167° C.

Example 72

N-{4-[5-(4-Methanesulfonyl-benzoyl)-2-morpholin-4-yl-thiophene-3-yl]-phenyl}-acetamide The title compound was made from N-{4-[(Z)-1-(morpholine-4-carbothioyl)-2-morpholin-4-yl-vinyl]-phenyl}-acetamide (0.500 gm, 0.0014 moles) and 4-methanesulfonylphenacyl bromide (0.0014 moles) as otherwise described in Example 39. Yield 42%. LC MS (M+1) 485. Rf: 0.52, M.P: 177° C.

Example 73

N-{4-[5-(4-acetylamino-benzoyl)-2-morpholin-4-yl-thiophene-3-yl]-phenyl}-acetamide The title compound was made from N-{4-[(Z)-1-(morpholine-4-carbothioyl)-2-morpholin-4-yl-vinyl]-phenyl}-acetamide (0.500 gm, 0.0014 moles) and 1-[4-(2-Bromo-acetyl)-phenyl]-propan-2-one (0.0014 moles) as otherwise described in Example 39. Yield 36%. LC MS (M+1) 464. Rf: 0.54, M.P: 152° C.

Example 74

N-{4-[2-Morpholin-4-yl-5-(pyridine-3-carbonyl)-thiophene-3-yl]-phenyl}-acetamide The title compound was made from N-{4-[(Z)-1-(morpholine-4-carbothioyl)-2-morpholin-4-yl-vinyl]-phenyl}-acetamide (0.500 gm, 0.0014 moles) and 2-bromo-1-pyridin-3-yl-ethanone (0.0014 moles) as otherwise described in Example 39. Yield 39%. LC MS (M+1) 408. Rf: 0.69, M.P: 144° C.

Example 75

N-{4-[2-Morpholin-4-yl-5-(pyridine-4-carbonyl)-thiophene-3-yl]-phenyl}-acetamide The title compound was made from N-{4-[(Z)-1-(morpholine-4-carbothioyl)-2-morpholin-4-yl-vinyl]-phenyl}-acetamide (0.500 gm, 0.0014 moles) and 2-bromo-1-pyridin-4-yl-ethanone (0.0014 moles) as otherwise described in Example 39. Yield 38%. LC MS (M+1) 408. Rf: 0.82, M.P: 149° C.

Example 76

[4-(4-Chloro-phenyl)-5-morpholin-4-yl-thiophen-2-yl]-(5-methoxy-4,6-dimethyl-pyridin-2-yl)-methanone The title compound was made from (Z)-2-(4-chloro-phenyl)-1,3-dimorpholin-4-yl-propenethione (0.500 gm, 0.0014 moles) and 2-chloromethyl-4-methoxy-3,5-dimethyl-pyridine (0.0014 moles) as otherwise described in Example 39. Yield 48%. LC MS (M+1) 466. Rf: 0.28, M.P: 160° C.

Example 77

4-[3-(4-Chloro-phenyl)-5-[5-methyl-4-(2,2,2-trifluoro-ethoxy)-pyridin-2-yl]-thiophen-2-yl]-morpholine The title compound was made from (Z)-2-(4-chloro-phenyl)-1,3-dimorpholin-4-yl-propenethione (0.500 gm, 0.0014 moles) and 2-chloromethyl-5-methyl-4-(2,2,2-trifluoro-ethoxy)-pyridine (0.0014 moles) as otherwise described in Example 39. Yield 48%. LC MS (M+1) 454, Rf; 0.39, M.P: 177-8° C.

Example 78

[4-(4-Chloro-phenyl)-5-morpholin-4-yl-thiophen-2-yl]-phenyl-methanone

The title compound was made from (Z)-2-(4-chloro-phenyl)-1,3-dimorpholin-4-yl-propenethione (0.500 gm, 0.0014 moles) and phenacyl bromide (0.0014 moles) as otherwise described in Example 39. Yield 68%. LC MS (M+1) 437. Rf: 0.49, M.P: 180° C.

Example 79

[4-(4-Chloro-phenyl)-5-morpholin-4-yl-thiophen-2-yl]-p-tolyl-methanone

The title compound was made from (Z)-2-(4-chloro-phenyl)-1,3-dimorpholin-4-yl-propenethione (0.500 gm, 0.0014 moles) and p-methylphenacyl bromide (0.0014 moles) as otherwise described in Example 39. Yield 70%. LC MS (M+1) 421. Rf: 0.52, M.P: 190° C.

Example 80

[4-(4-Chloro-phenyl)-5-morpholin-4-yl-thiophen-2-yl]-(4-methoxy-phenyl)-methanone The title compound was made from (Z)-2-(4-chloro-phenyl)-1,3-dimorpholin-4-yl-propenethione (0.500 gm, 0.0014 moles) and p-methoxyphenacyl bromide (0.0014 moles) as otherwise described in Example 39. Yield 48%. LC MS (M+1) 437. Rf: 0.56, M.P: 120° C.

Example 81

(4-Chloro-phenyl)-[4-(4-chloro-phenyl)-5-morpholin-4-yl-thiophen-2-yl]-methanone The title compound was made from (Z)-2-(4-chloro-phenyl)-1,3-dimorpholin-4-yl-propenethione (0.500 gm, 0.0014 moles) and p-chlorophenacyl bromide (0.0014 moles) as otherwise described in Example 39. Yield 58%. LC MS (M+2) 442, Rf; 0.52, M.P. 145-149° C.

Example 82

[4-(4-Chloro-phenyl)-5-morpholin-4-yl-thiophen-2-yl]-(2,4-dichloro-phenyl)-methanone The title compound was made from (Z)-2-(4-chloro-phenyl)-1,3-dimorpholin-4-yl-propenethione (0.500 gm, 0.0014 moles) and 2,4-dichlorophenacylbromide (0.0014 moles) as otherwise described in Example 39. Yield 39%. LC MS (M+2) 476. Rf: 0.60, M.P: 110° C.

Example 83

[4-(4-Chloro-phenyl)-5-morpholin-4-yl-thiophen-2-yl]-(4-methanesulfanyl-phenyl)-methanone The title compound was made from (Z)-2-(4-chloro-phenyl)-1,3-dimorpholin-4-yl-propenethione (0.500 gm, 0.0014 moles) and 4-methanesulfanylphenacyl bromide (0.0014 moles) as otherwise described in Example 39. Yield 48%. LC MS (M+1) 453, Rf; 0.39, M.P: 198-9° C.

Example 84

[4-(4-Chloro-phenyl)-5-morpholin-4-yl-thiophen-2-yl]-(4-methanesulfonyl-phenyl)-methanone The title compound was made from (Z)-2-(4-chloro-phenyl)-1,3-dimorpholin-4-yl-propenethione (0.500 gm, 0.0014 moles) and 4-methanesulfonylphenacyl bromide (0.0014 moles) as otherwise described in Example 39. Yield 42%. LC MS (M+1) 485, Rf; 0.58, M.P: 242-3° C.

Example 85

N-{4-[4-(4-Chloro-phenyl)-5-morpholin-4-yl-thiophen-2-carbonyl]-phenyl}acetamide The title compound was made from (Z)-2-(4-chloro-phenyl)-1,3-dimorpholin-4-yl-propenethione (0.500 gm, 0.0014 moles) and 1-[4-(2-bromo-acetyl)-phenyl]-propan-2-one (0.0014 moles) as otherwise described in Example 39. Yield 36%. LC MS (M+1) 464, Rf; 0.66, M.P: 125-7° C.

Example 86

[4-(4-Chloro-phenyl)-5-morpholin-4-yl-thiophen-2-yl]-pyridin-3-yl-methanone

The title compound was made from (Z)-2-(4-chloro-phenyl)-1,3-dimorpholin-4-yl-propenethione (0.500 gm, 0.0014 moles) and 2-bromo-1-pyridin-3yl-ethanone (0.0014 moles) as otherwise described in Example 39. Yield 39%. LC MS (M+1) 408. Rf: 0.63, M.P: 114° C.

Example 87

[4-(4-Chloro-phenyl)-5-morpholin-4-yl-thiophen-2-yl]-pyridin-4-yl-methanone

The title compound was made from (Z)-2-(4-chloro-phenyl)-1,3-dimorpholin-4-yl-propenethione (0.500 gm, 0.0014 moles) and 2-bromo-1-pyridin-4-yl-ethanone (0.0014 moles) as otherwise described in Example 39. Yield 38%. LC MS (M+1) 408. Rf: 0.57, M.P: 117° C.

Example 88

4-[5-(5-Methoxy-4,6-dimethyl-pyridin-2-yl)-3-pyridin-3-yl-thiophen-2-yl]-morpholine The title compound was made from (Z)-1,3-di-morpholin-4-yl-2-pyridin-3-yl-propenthione (0.500 gm, 0.0015 moles) and 2-chloromethyl-4-methoxy-3,5-dimethyl-pyridine (0.0015 moles) as otherwise described in Example 39. Yield 48%. LC MS (M+1) 382, Rf; 0.42, M.P: 139-40° C.

Example 89

4-{5-[5-Methyl-5-(2,2,2-trifluoro-ethoxy)-pyridin-2-yl]-3-pyridin-3-yl-thiphen-2-yl}-morpholine The title compound was made from (Z)-1,3-dimorpholin-4-yl-2-pyridin-3-yl-propenethione (0.500 gm, 0.0015 moles) and 2-chloromethyl-5-methyl-4-(2,2,2-trifluoro-ethoxy)-pyridine (0.0015 moles) as otherwise described in Example 39. Yield 48%. LC MS (M+1) 398. Rf: 0.58, M.P: 129° C.

Example 90

(5-Morpholin-4-yl-4-pyridin-3-yl-thiophene-2-yl)-phenyl-methanone

The title compound was made from (Z)-1,3-dimorpholin-4-yl-2-pyridin-3-yl-propenthione (0.500 gm, 0.0015 moles) and phenacyl bromide (0.0015 moles) as otherwise described in Example 39. Yield 68%. LC MS (M+1) 437, Rf; 0.53 M.P: 168-9° C.

Example 91

(5-Morpholin-4-yl-4-pyridin-3-yl-thiophene-2-yl)-p-tolyl-methanone

The title compound was made from (Z)-1,3-dimorpholin-4-yl-2-pyridin-3-yl-propenthione (0.500 gm, 0.0015 moles) and p-methylphenacyl bromide (0.0015 moles) as otherwise described in Example 39. Yield 70%. LC MS (M+1) 351. Rf: 0.51, M.P: 134° C.

Example 92

(4-Methoxy-phenyl)-(5-morpholin-4-yl-4-pyridin-3-yl-thiophen-2-yl)methanone

The title compound was made from (Z)-1,3-dimorpholin-4-yl-2-pyridin-3-yl-propenthione (0.500 gm, 0.0015 moles) and p-methoxyphenacyl bromide (0.0015 moles) as otherwise described in Example 39. Yield 48%. LC MS (M+1) 365. Rf: 0.54, M.P: 149° C.

Example 93

(4-Chloro-phenyl)-(5-morpholin-4-yl-4-pyridin-3-yl-thiophen-2-yl)-methanone

The title compound was made from ((Z)-1,3-dimorpholin-4-yl-2-pyridin-3-yl-propenthione (0.500 gm, 0.0015 moles) and p-chlorophenacyl bromide (0.0015 moles) as otherwise described in Example 39. Yield 58%. LC MS (M+2) 386. Rf: 0.58, M.P: 196° C.

Example 94

(2,4-Dichloro-phenyl)-(5-morpholin-4-yl-4-pyridin-3-yl-thiophen-2-yl)-methanone

The title compound was made from (Z)-1,3-dimorpholin-4-yl-2-pyridin-3-yl-propenthione (0.500 gm, 0.0015 moles) and 2,4-dichlorophenacyl bromide (0.0015 moles) as otherwise described in Example 39. Yield 39%. LC MS (M+2) 420. Rf: 0.69, M.P: 176° C.

Example 95

(4-Methylsulfanyl-phenyl)-(5-morpholin-4-yl-4-pyridin-3-yl-thiophen-2-yl)-methanone Article I. The title compound was made from (Z)-1,3-dimorpholin-4-yl-2-pyridin-3-yl-propenthione (0.500 gm, 0.0015 moles) and 4-methanesulfanylphenacyl bromide (0.0015 moles) as otherwise described in Example 39. Yield 48%. LC MS (M+1) 397.Rf: 0.29, M.P: 182° C.

Example 96

(4-Methylsulfonyl-phenyl)-(5-morpholin-4-yl-4-pyridin-3-yl-thiophen-2-yl)-methanone The title compound was made from (Z)-1,3-dimorpholin-4-yl-2-pyridin-3-yl-propenthione (0.500 gm, 0.0015 moles) and 4-methanesulfonylphenacyl bromide (0.0015 moles) as otherwise described in Example 39. Yield 42%. LC MS (M+1) 429. Rf: 0.49, M.P: 147° C.

Example 97

N-[4-(5-Morpholin-4-yl-4-pyridin-3-yl-thiophen-2-carbonyl)-phenyl]-acetamide

The title compound was made from (Z)-1,3-dimorpholin-4-yl-2-pyridin-3-yl-propenthione (0.500 gm, 0.0015 moles) and 1-[4-(2-bromo-acetyl)-phenyl]-propan-2-one (0.0015 moles) as otherwise described in Example 39. Yield 36%. LC MS (M+1) 408. Rf: 0.62, M.P: 120° C.

Example 98

(5-Morpholin-4-yl-4-pyridin-3-yl-thiophen-2-yl)-pyridin-3-yl-methanone

The title compound was made from (Z)-1,3-dimorpholin-4-yl-2-pyridin-3-yl-propenthione (0.500 gm, 0.0015 moles) and 2-bromo-1-pyridin-3yl-ethanone (0.0015 moles) as otherwise described in Example 39. Yield 39%. LC MS (M+1) 352. Rf: 0.63, M.P: 145° C.

Example 99

(5-Morpholin-4-yl-4-pyridin-3-yl-thiophen-2-yl)-pyridin-4-yl-methanone

The title compound was made (Z)-1,3-dimorpholin-4-yl-2-pyridin-3-yl-propenthione (0.500 gm, 0.0015 moles) and 2-bromo-1-pyridin-4yl-ethanone (0.0015 moles) as otherwise described in Example 39. Yield 38%. LC MS (M+1) 352. Rf: 0.64, M.P: 128° C.

Example 100

4-[5-(5-Methoxy-4,6-dimethyl-pyridin-2-yl)-3-pyridin-4-yl-thiophen-2-yl]-morpholine The title compound was made from (Z)-1,3-dimorpholin-4-yl-2-pyridin-4-yl-propenthione (0.500 gm, 0.0015 moles) and 2-chloromethyl-4-methoxy-3,5-dimethyl-pyridine (0.0015 moles) as otherwise described in Example 39. Yield 48%. LC MS (M+1) 382. Rf: 0.58, M.P: 129° C.

Example 101

4-{5-[5-Methyl5-(2,2,2-trifluoro-ethoxy)-pyridin-2-yl]-3-pyridin-4-yl-thiphen-2-yl}-morpholine The title compound was made from (Z)-1,3-dimorpholin-4-yl-2-pyridin-4-yl-propenthione (0.500 gm, 0.0015 moles) and 2-chloromethyl-5-methyl-4-(2,2,2-trifluoro-ethoxy)-pyridine (0.0015 moles) as otherwise described in Example 39. Yield 48%. LC MS (M+1) 398. Rf: 0.59, M.P: 149° C.

Example 102

(5-Morpholin-4-yl-4-pyridin-4-yl-thiophene-2-yl)-phenyl-methanone

The title compound was made from (Z)-1,3-dimorpholin-4-yl-2-pyridin-4-yl-propenthione (0.500 gm, 0.0015 moles) and phenacyl bromide (0.0015 moles) as otherwise described in Example 39. Yield 68%. LC MS (M+1) 351. Rf: 0.63, M.P: 122° C.

Example 103

(5-Morpholin-4-yl-4-pyridin-4-yl-thiophene-2-yl)-p-tolyl-methanone

The title compound was made from (Z)-1,3-dimorpholin-4-yl-2-pyridin-4-yl-propenthione (0.500 gm, 0.0015 moles) and p-methylphenacyl bromide (0.0015 moles) as otherwise described in Example 39. Yield 70%. LC MS (M+1) 365, M.P: 144-5° C., Rf; 0.56.

Example 104

(4-Methoxy-phenyl)-(5-morpholin-4-yl-4-pyridin-4-yl-thiophen-2-yl)-methanone

The title compound was made from (Z)-1,3-dimorpholin-4-yl-2-pyridin-4-yl-propenthione (0.500 gm, 0.0015 moles) and p-methoxyphenacyl bromide (0.0015 moles) as otherwise described in Example 39. Yield 48%. LC MS (M+1) 381. Rf: 0.60, M.P: 193° C.

Example 105

(4-Chloro-phenyl)-(5-morpholin-4-yl-4-pyridin-4-yl-thiophen-2-yl)-methanone

The title compound was made from ((Z)-1,3-dimorpholin-4-yl-2-pyridin-4-yl-propenthione (0.500 gm, 0.0015 moles) and p-chlorophenacyl bromide (0.0015 moles) as otherwise described in Example 39. Yield 58%. LC MS (M+2) 386. Rf: 0.67, M.P: 176° C.

Example 106

(2,4-Dichloro-phenyl)-(5-morpholin-4-yl-4-pyridin-4-yl-thiophen-2-yl)-methanone

The title compound was made from (Z)-1,3-dimorpholin-4-yl-2-pyridin-4-yl-propenthione (0.500 gm, 0.0015 moles) and 2,4-dichlorophenacyl bromide (0.0015 moles) as otherwise described in Example 39. Yield 39%. LC MS (M+2) 420. Rf: 0.70, M.P: 180° C.

Example 107

(4-Methylsulfanyl-phenyl)-(5-morpholin-4-yl-4-pyridin-3-yl-thiophen-2-yl)-methanone The title compound was made from (Z)-1,3-dimorpholin-4-yl-2-pyridin-4-yl-propenthione (0.500 gm, 0.0015 moles) and 4-methanesulfanylphenacyl bromide (0.0015 moles) as otherwise described in Example 39. Yield 48%. LC MS (M+1) 397. Rf: 0.59, M.P: 127° C.

Example 108

(4-Methylsulfonyl-phenyl)-(5-morpholin-4-yl-4-pyridin-4-yl-thiophen-2-yl)-methanone The title compound was made from (Z)-1,3-dimorpholin-4-yl-2-pyridin-4-yl-propenthione (0.500 gm, 0.0015 moles) and 4-methanesulfonylphenacyl bromide (0.0015 moles) as otherwise described in Example 39. Yield 42%. LC MS (M+1) 429. Rf: 0.54, M.P: 128° C.

Example 109

N-[4-(5-Morpholin-4-yl-4-pyridin-4-yl-thiophen-2-carbonyl)-phenyl]-acetamide

The title compound was made from (Z)-1,3-dimorpholin-4-yl-2-pyridin-4-yl-propenthione (0.500 gm, 0.0015 moles) and 1-[4-(2-Bromo-acetyl)-phenyl]-propan-2-one (0.0015 moles) as otherwise described in Example 39. Yield 36%. LC MS (M+1) 408. Rf: 0.64, M.P: 139° C.

Example 110

(5-Morpholin-4-yl-4-pyridin-4-yl-thiophen-2-yl)-pyridin-3-yl-methanone

The title compound was made from (Z)-1,3-dimorpholin-4-yl-2-pyridin-4-yl-propenthione (0.500 gm, 0.0015 moles) and 2-bromo-1-pyridin-3yl-ethanone (0.0015 moles) as otherwise described in Example 39. Yield 39%. LC MS (M+1) 352. Rf: 0.74, M.P: 124° C.

Example 111

(5-Morpholin-4-yl-4-pyridin-4-yl-thiophen-2-yl)-pyridin-4-yl-methanone

The title compound was made (Z)-1,3-dimorpholin-4-yl-2-pyridin-3-yl-propenthione (0.500 gm, 0.0015 moles) and 2-bromo-1-pyridin-4yl-ethanone (0.0015 moles) as otherwise described in Example 39. Yield 38%. LC MS (M+1) 352. Rf: 0.74, M.P: 124° C.

Example 112

Bis-[4-(4-methanesulfonyl-phenyl)-5-morpholin-4-yl-thiophen-2-yl]-methanone

The title compound was made from (Z)-2-(4-methanesulfonyl-phenyl)-1,3-dimorpholine (1.0 gm, 0.0026 moles) and 1,3-dichloroacetone (0.0013 moles) as otherwise described in Example 39. Yield 69%. LC MS (M+1) 672. Rf: 0.62, M.P: 235-236° C.

Example 113

N-{4-{5-[4-(4-acetylamino-phenyl)-5-morpholin-4-yl-thiophene-2-carbonyl]-2-morpholin-4-yl-thiophene-3-yl}-phenyl)-acetamide The title compound was made from N-{4-[(Z)-1-(morpholine-4-carbothioyl)-2-morpholin-4-yl-vinyl]-phenyl}-acetamide (1.0 gm, 0.0028 moles) and 1,3-Dichloroacetone (0.0014 moles) as otherwise described in Example 39. Yield 69%. LC MS (M+1) 630. Rf: 0.52, M.P: 140-142° C.

Example 114

Bis-[4-(4-chloro-phenyl)-5-morpholin-4-yl-thiophen-2-yl]-methanone

The title compound was made from (Z)-2-(4-chloro-phenyl)-1,3-dimorpholine (1.0 gm, 0.0026 moles) and 1,3-dichloroacetone (0.0013 moles) as otherwise described in Example 39. Yield 69%. LC MS (M+1) 584. Rf: 0.58, M.P: 135-136° C.

Example 115

(4-Amino-2-phenylamino-thiazole-5-yl)-4-(methoxy-phenyl)-methanone

The title compound was made from 1-diaminomethyline-3-phenyl-thiourea (0.0026 moles) and p-methoxyphenacyl bromide (0.0026 moles) as otherwise described in Example 39. Yield 39%. LC MS (M+1) 325. Rf: 0.52, M.P: 222-225° C.

Example 116

[2-(4-Chloro-phenylamino)-4-pyridin-4-yl-thiazole-5-yl]-4-methoxy-phenyl)-methanone The title compound was made from 1-[1-Amino-1-pyridin-4-yl-meth-(Z)-ylidene]3-(4-chloro-phenyl)-thiourea (0.0026 moles) and p-methoxyphenacyl bromide (0.0026 moles) as otherwise described in Example 39. Yield 50%. LC MS (M+1) 422. Rf: 0.52, M.P: 201-202° C.

Example 117

1-(4-Fluoro-phenyl)-3-[5-(4-methoxy-benzoyl)-2-phenylamino-thiazol-4-yl]-urea (4-Amino-2-phenylamino-thiazole-5-yl)-4-(methoxyphenyl)-methanone (0.0003 mole) in dry THF (10 ml) and p-fluorophenyl isocyanate (0.0003) were added to 5 ml THF. The reaction mixture was stirred for 2 hours. The title compound separated as a white precipitate. Yield 80%. LC MS (M+1) 463, M.P: 177-8° C., Rf; 0.39.

Example 118

Bis-(4-methyl-2-methylamino-thiazole-5-yl)-methanone

The title compound was made from 1-[1-diethylamino-eth-(z)-ylidene]-3-methyl-thiourea (0.0026 moles) and 1,3-dichloroacetone (0.0013 moles) as otherwise described in Example 112. Yield 70%. LC MS (M+1) 283, M.P: 184-5° C., Rf; 0.32.

Example 119

Bis-(4-methyl-2-phenylamino-thiazole-5-yl)-methanone

The title compound was made from 1-[1-diethylamino-eth-(z)-ylidene]-3-phenyl-thiourea (0.0026 moles) and 1,3-dichloroacetone (0.0013 moles) as otherwise described in Example 112. Yield 50%. LC MS (M+1) 407, M.P: 194-6° C., Rf; 0.82.

Example 120

Bis-[2-(4-Chloro-phenylamino)-4-methyl-thiazole-5-yl]-methanone

The title compound was made from 1-(4-chloro-phenyl)-3-[1-diethylamino-eth-(Z)-ylidene]-thiourea (0.0026 moles) and 1,3-dichloroacetone (0.0013 moles) as otherwise described in Example 112. Yield 60%. LC MS (M+ and M+2) 474 & 476, M.P: 184-6° C., Rf; 0.49.

Example 121

Bis-[2-(2-Benzoyl-amino)-4-methyl-thiazole-5-yl]-methanone

The title compound was made from 1-benzoyl-3-[1-diethylamino-eth-(Z)-ylidene]-thiourea (0.0026 moles) and 1,3-dichloroacetone (0.0013 moles) as otherwise described in Example 112. Yield 60%. LC MS (M+1) 463, M.P: 232-3° C., Rf; 0.58.

Example 122

Bis-[2-(2-Furoyl-amino)-4-methyl-thiazole-5-yl]-methanone

The title compound was made from 1-furoyl-3-[1-diethylamino-eth-(Z)-ylidene]-thiourea (0.0026 moles) and 1,3-dichloroacetone (0.0013 moles) as otherwise described in Example 112. Yield 60%. LC MS (M+1) 443, M.P: 198-9° C., Rf; 0.55.

Example 123

Dimethyl [carbonyl-bis(4-methyl-1,3-thiazole-5,2-diyl)]bis-carbamate

The title compound was made from methyl ({[(1E-1-(diethylamino) methylidene]amino}carbonothioyl)carbamate (0.0026 moles) and 1,3-dichloroacetone (0.0013 moles) as otherwise described in Example 112. Yield 60%. LC MS (M+1) 371, M.P: 188-9° C., Rf; 0.63.

Example 124

Diethyl [carbonyl-bis(4-methyl-1,3-thiazole-5,2-diyl)]bis-carbamate

The title compound was made from ethyl ({[(1E)-1-(diethylamino) ethylidene]amino}carbonothioyl)carbamate (0.0026 moles) and 1,3-dichloroacetone (0.0013 moles) as otherwise described in Example 112. Yield 60%. LC MS (M+1) 399, M.P: Char at 284° C., Rf; 0.29.

Example 125

Bis-(2-methylamino-4-Phenyl-thiazole-5-yl)-methanone

The title compound was made from [1-diethylamino-1-phenyl-meth-(Z)-ylidene]-thiourea (0.0026 moles) and 1,3-Dichloroacetone (0.0013 moles) as otherwise described in Example 112. Yield 70%. LC MS (M+1) 407, M.P: Char at 280° C., Rf; 0.43.

Example 126

Bis-(2-phenylamino-4-phenyl-thiazole-5-yl)-methanone

The title compound was made from 1-[1-diethylamino-1-phenyl-meth-(Z)-ylidene]-3-phenyl-thiourea (0.0026 moles) and 1,3-dichloroacetone (0.0013 moles) as otherwise described in Example 112. Yield 50%. LC MS (M+1) 531, M.P: Char at 290° C., Rf; 0.78.

Example 127

Bis-[2-(4-Chloro-phenylamino)-4-phenyl-thiazole-5-yl]-methanone

The title compound was made from 1-(4-chloro-phenyl)-3-[1-diethylamino-1-phenyl-meth-(Z)-ylidene]-thiourea (0.0026 moles) and 1,3-dichloroacetone (0.0013 moles) as otherwise described in Example 112. Yield 60%. LC MS (M+2) 602, M.P: Char at 290° C., Rf; 0.56.

Example 128

Bis-[2-(2-Benzoyl-amino)-4-methyl-thiazole-5-yl]-methanone

The title compound was made from 1-benzoyl-3-[1-diethylamino-1-phenyl-meth-(Z)-ylidene]-thiourea (0.0026 moles) and 1,3-dichloroacetone (0.0013 moles) as otherwise described in Example 112. Yield 60%. LC MS (M+1) 587, M.P: Char at 290° C., Rf; 0.36.

Example 129

Bis-[2-(2-Furoyl-amino)-4-phenyl-thiazole-5-yl]-methanone

The title compound was made from 1-furoyl-3-[1-diethylamino-1-phenyl-meth-(Z)-ylidene]-thiourea (0.0026 moles) and 1,3-dichloroacetone (0.0013 moles) as otherwise described in Example 112. Yield 60%. LC MS (M+1) 566, M.P: Char at 260° C., Rf; 0.58.

Example 130

Dimethyl [carbonyl-bis(4-phenyl-1,3-thiazole-5,2-diyl)]bis-carbamate

The title compound was made from methyl ({[(1E)-(diethylamino) (phenyl)methylene]amino}carbonothioyl)carbamate (0.0026 moles) and 1,3-dichloroacetone (0.0013 moles) as otherwise described in Example 112. Yield 60%. LC MS (M+1) 522, M.P: Char at 250° C., Rf; 0.63.

Example 131

Diethyl [carbonyl-bis(4-phenyl-1,3-thiazole-5,2-diyl)]bis-carbamate

The title compound was made from ethyl ({[(1]-(diethylamino) (phenyl)amino}carbonothioyl)carbamate (0.0026 moles) and 1,3-dichloroacetone (0.0013 moles) as otherwise described in Example 112. Yield 60%. LC MS (M+1) 523, M.P: Char at 245° C., Rf; 0.46.

Example 132

Bis-(2-methylamino-4-benzayl-thiazole-5-yl)-methanone

The title compound was made from [1-diethylamino-1-benzyl-(Z)-ylidene]-thiourea (0.0026 moles) and 1,3-dichloroacetone (0.0013 moles) as otherwise described in Example 112. Yield 70%. LC MS (M+1) 407, M.P: Char at 268° C., Rf; 0.67.

Example 133

Bis-(2-phenylamino-4-benzayl-thiazole-5-yl)-methanone

The title compound was made from 1-[1-diethylamino-1-benzyl-(Z)-ylidene]-3-phenyl-thiourea (0.0026 moles) and 1,3-dichloroacetone (0.0013 moles) as otherwise described in Example 112. Yield 50%. LC MS (M+1) 531, M.P: Char at 285° C., Rf; 0.53.

Example 134

Bis-[2-(4-Chloro-phenylamino)-4-benzayl-thiazole-5-yl]-methanone

The title compound was made from 1-(4-chloro-phenyl)-3-[1-diethylamino-1-benzyl-(Z)-ylidene]-thiourea (0.0026 moles) and 1,3-Dichloroacetone (0.0013 moles) as otherwise described in Example 112. Yield 60%. LC MS (M+2) 602, M.P: 265-6° C., Rf; 0.28.

Example 135

Bis-[2-(2-benzoyl-amino)-4-benzayl-thiazole-5-yl]-methanone

The title compound was made from 1-benzoyl-3-[1-diethylamino-1-benzyl-(Z)-ylidene]-thiourea (0.0026 moles) and 1,3-dichloroacetone (0.0013 moles) as otherwise described in Example 112. Yield 60%. LC MS (M+1) 587, M.P: 294° C., Rf; 0.47.

Example 136

Bis-[2-(2-furoyl-amino)-4-benzayl-thiazole-5-yl]-methanone

The title compound was made from 1-furoyl-3-[1-diethylamino-1-benzyl-(Z)-ylidene]-thiourea (0.0026 moles) and 1,3-dichloroacetone (0.0013 moles) as otherwise described in Example 112. Yield 60%. LC MS (M+1) 566, M.P: Char at 265° C., Rf; 0.58.

Example 137

Dimethyl [carbonyl-bis(4-benzyl-1,3-thiazole-5,2-diyl)]bis-carbamate

The title compound was made from methyl ({[(1E)-(diethylamino) (benzyl)methylene]amino}carbonothioyl)carbamate (0.0026 moles) and 1,3-dichloroacetone (0.0013 moles) as otherwise described in Example 112. Yield 60%. LC MS (M+1) 522, M.P: 189-90° C., Rf; 0.69.

Example 138

Diethyl [carbonyl-bis(4-benzyl-1,3-thiazole-5,2-diyl)]bis-carbamate

The title compound was made from ethyl ({[(1E)-(diethylamino) (benzyl)methylene]amino}carbonothioyl)carbamate (0.0026 moles) and 1,3-dichloroacetone (0.0013 moles) as otherwise described in Example 112. Yield 60%. LC MS (M+1) 523, M.P: 145-6° C., Rf; 0.67.

Example 139

2-(2-Chloroacetyl amino)benzoic acid

Anthranilic acid (50 g, 0.365 mole) was dissolved in dichloromethane. An equimolar amount of triethylamine (TEA) was added, and the reaction mass was cooled to 0° C. Chloroacetyl chloride (41.12 g, 0.365 mol) was added over a period of 15 minutes, while maintaining the temperature at 0° C. The reaction mass was then stirred at room temperature (rt) for 4 hr. A white solid precipitated, which was filtered and washed with ample water, and then dried and recrystallized to obtain 55 g of the title compound. Yield: 64.5%, M.P. 183-5° C., LC-MS: 214(M+1), Rf: 0.47

Example 140

2-Chloromethyl-3-(4-chlorophenyl)-3H-quinazolin-4-one 2-(2-Chloroacetyl amino) benzoic acid 20 g (0.094 mole) and an equimolar amount of p-chloro aniline were dissolved in toluene and stirred at rt for 30 minutes. An equimolar amount of phosphorus trichloride was then added with continued stirring. The temperature was raised, and the reaction mixture was refluxed until thin-layer chromatography (TLC) indicated completion of the reaction. The reaction mixture was then cooled to rt, and the solvent was evaporated under vacuum. To the residue was added water, and the mixture was neutralized with sodium bicarbonate and extracted with chloroform. The organic layer was washed with water and dried over anhydrous sodium sulphate. The solvent was removed under vacuum, and the residue was recrystallized from methanol to produce 2-chloromethyl-3-(4-chloro-phenyl)-3H-quinazoline-4-one. Yield: 26.5%, M.P. 234-5° C., LC-MS: 305(M+1), Rf: 0.62

Example 141

2-Chloromethyl-3-(2-chloro-phenyl)-3H-quinazolin-4-one

The title compound was prepared from 2-(2-chloroacetyl amino) benzoic acid and o-chloroaniline as otherwise described in Example 140. Yield 25.6%, M.P. 195-6° C., LC-MS: 305(M+1), Rf: 0.61.

Example 142

2-Chloromethyl-3-(3-chloro-phenyl)-3H-quinazolin-4-one

The title compound was prepared from 2-(2-chloroacetyl amino) benzoic acid and m-chloroaniline as otherwise described in Example 140. Yield: 27.5%, M.P. 202-5° C., LC-MS: 305(M+1), Rf: 0.59.

Example 143

2-Chloromethyl-3-(4-methyl-phenyl)-3H-quinazolin-4-one 2-(2-Chloroacetyl amino) benzoic acid 20 g (0.094 mole) and an equimolar amount of p-methylaniline were dissolved in toluene and stirred at rt for 30 minutes. An equimolar amount of phosphorus trichloride was added with continued stirring. The temperature was raised, and the reaction mixture was refluxed until thin-layer chromatography (TLC) indicated completion of the reaction. To the residue was added water, and the mixture was neutralized with sodium bicarbonate and extracted with chloroform. The organic layer was washed with water and dried over anhydrous sodium sulphate. The solvent was removed under vacuum, and the residue was recrystallized from methanol to produce 2-chloromethyl-3-(4-chloro-phenyl)-3H-quinazoline-4-one. Yield: 36%, M.P. 265-6° C., LC-MS: 285(M+1), Rf: 0.64

Example 144

2-Chloromethyl-3-(2-methyl-phenyl)-3H-quinazolin-4-one

The title compound was prepared from 2-(2-chloroacetyl amino) benzoic acid and o-methylaniline as otherwise described in Example 143. Yield: 29%, M.P. 205-6° C., LC-MS: 285(M+1), Rf: 0.54.

Example 145

2-Chloromethyl-3-(3-methyl-phenyl)-3H-quinazolin-4-one

The title compound was prepared from 2-(2-chloroacetyl amino) benzoic acid and m-methylaniline as otherwise described in Example 143. Yield: 32.5%, M.P. 183-5° C., LC-MS: 285(M+1), Rf: 0.58.

Example 146

2-Chloromethyl-3-(4-methoxy-phenyl)-3H-quinazolin-4-one 2-(2-Chloroacetyl amino) benzoic acid 20 g (0.094 mole) and an equimolar amount of p-methoxyaniline were mixed in toluene and stirred at rt for 30 minutes. An equimolar amount of phosphorus trichloride was added with continued stirring, and the temperature was raised and the reaction mixture was refluxed until TLC indicated completion of reaction. The reaction mixture was then cooled to rt, and the solvent was evaporated under vacuum. To the residue was added water, and the reaction mixture was neutralized with sodium bicarbonate and extracted with chloroform. The solvent was removed under vacuum, and the residue was recrystallized from methanol to produce 2-chloromethyl-3-(4-chloro-phenyl)-3H-quinazoline-4-one. Yield: 34%, M.P. 154-5° C., LC-MS: 301(M+1), Rf: 0.57.

Example 147

2-Chloromethyl-3-(2-methoxy-phenyl)-3H-quinazolin-4-one

The title compound was prepared from 2-(2-chloroacetyl amino) benzoic acid and o-methoxyaniline as otherwise described in Example 146. Yield: 31.4%, M.P. 193-4° C., LC-MS: 301(M+1), Rf: 0.62.

Example 148

2-Chloromethyl-3-(3-methoxy-phenyl)-3H-quinazolin-4-one

The title compound was prepared from 2-(2-chloroacetyl amino) benzoic acid and m-methoxy aniline as otherwise described in Example 146. Yield: 32.2%, M.P. 180-2° C., LC-MS: 301(M+1), Rf: 0.62.

Example 149

2-Chloromethyl-3-(phenyl)-3H-quinazolin-4-one 2-(2-Chloroacetyl amino) benzoic acid 20 g (0.094 mole) and an equimolar amount of aniline were dissolved in toluene and stirred at rt for 30 minutes. An equimolar amount of phosphorus trichloride was added with continued stirring, and the temperature was raised and the reaction mixture was refluxed until TLC indicated completion of reaction. The reaction mixture was then cooled to rt, and the solvent was evaporated under vacuum. To the residue was added water, and the reaction mixture was neutralized with sodium bicarbonate and extracted with chloroform. The organic layer was washed with water and dried over anhydrous sodium sulphate. The solvent was removed under vacuum, and the residue was recrystallized from methanol to produce 2-Chloromethyl-3-(phenyl)-3H-quinazoline-4-one. Yield: 28.3%, M.P. 152-3° C. LC-MS: 271(M+1), Rf: 0.48.

Example 150

2-Chloromethyl-3-(p-acetylphenyl)-3H-quinazolin-4-one

The title compound was prepared from 2-(2-chloroacetyl amino) benzoic acid and acetophenone as otherwise described in Example 146. Yield: 36%, M.P. 180-1° C. LC-MS: 313(M+1), Rf: 0.54.

Example 151

2-Acetylamino-benzoic acid

The title compound was prepared from anthranilic acid and acetyl chloride as otherwise described in Example 139. Yield: 65.3%, M.P. 157-8° C., LC-MS: 170(M+1), Rf: 0.51.

Example 152

3-(4-Chlorophenyl)-2-methyl-3H-quinazolin-4-one

The title compound was prepared from 2-acetylamino-benzoic acid and p-chloroaniline as otherwise described in Example 140. Yield: 37.5%, M.P. 141-2° C., LC-MS: 271 (M+1), Rf: 0.61.

Example 153

2-(3-Chloro-2-oxo-propyl)-3-(4-chlorophenyl)-3H-quinazolin-4-one 3-(4-Chloro-phenyl)-2-methyl-3H-quinazolin-4-one 40 g (0.15 moles) was dissolved in dry tetrahydrofuran (THF), cooled to 0° C., and then maintained between 0° C. to 5° C. An equimolar amount of chloroacetyl chloride in dry THF was added. The reaction mixture was stirred between 0° C. to 5° C. for 2 hrs, and then at rt for 3 hrs. The reaction mixture was then poured over crushed ice, stirred well, filtered, and recrystallized from methanol to produce 2-(3-chloro-2-oxo-propyl)-3-(4-chloro-phenyl)-3H-quinazolin-4-one. Yield: 26.4%, M.P. >275° C. LC-MS: 347(M+1), Rf: 0.52.

Example 154

(4-Methyl-5-(4-oxo-3-phenyl-3,4-dihydro-quinazolin-2-yl)-thiazol-2-yl)-carbamic acid ethyl ester A solution of carbamic acid, [{(1-(diethyl amino)ethylidene) amino}thiaoxomethyl]-ethyl ester (1 gm, 0.001 mole) and an equimolar amount of 2-chloromethyl-3-(phenyl)-3H-quinazoline-4-one in acetonitrile was heated to 80° C. for 4 hrs and then cooled to rt. The title compound precipitated was filtered and recrystallized in methanol. Yield: 48%, M.P. 248-251° C., LC-MS: 407(M+1), Rf: 0.52.

Example 155

(4-Methyl-5-(4-oxo-3-phenyl-3,4-dihydro-quinazolin-2-yl)-thiazol-2-yl)-carbamic acid methyl ester The title compound was prepared from carbamic acid, [{(1-(diethyl amino)ethylidene) amino}thiaoxomethyl]-methyl ester and 2-chloromethyl-3-(phenyl)-3H-quinazoline-4-one as otherwise described in Example 154. Yield: 41.4%, M.P. >275° C., LC-MS: 393(M+1).

Example 156

2-(4-Methyl-2-methylamino-thiazol-5-yl)-3-phenyl-3H-quinazolin-4-one

The title compound was prepared from 1-(1-diethylamino-eth-(E)-ylidene)-3-methyl-thiourea and 2-chloromethyl-3-(phenyl)-3H-quinazoline-4-one as otherwise described in Example 154. Yield: 32.6%, M.P. 209-10° C., LC-MS: 348 (M+1), Rf: 0.5.

Example 157

2-(4-Methyl-2-phenylamino-thiazol-5-yl)-3-phenyl-3H-quinazolin-4-one

The title compound was prepared from 1-(1-diethylamino-eth-(E)-ylidene)-3-phenyl-thiourea and 2-chloromethyl-3-(phenyl)-3H-quinazoline-4-one as otherwise described in Example 154. Yield: 72.36%, M.P. 260-2° C., LC-MS: 411 (M+1), Rf: 0.51.

Example 158

2-[2-(4-Chlorophenylamino)-4-methyl-thiazol-5-yl]-3-phenyl-3H-quinazolin-4-one

The title compound was prepared from 1-(4-chloro-phenyl)-3-[1-diethylamino-eth-(E)-ylidene]-thiourea and 2-chloromethyl-3-(phenyl)-3H-quinazoline-4-one as otherwise described in Example 154. Yield: 38.46%, M.P. 230-232° C., LC-MS: 445(M+1), Rf: 0.32.

Example 159

[5-(4-Oxo-3-phenyl-3,4-dihydro-quinazolin-2-yl)-4-phenyl-thiazol-2-yl]-carbamic acid ethyl ester The title compound was prepared from benzenecarboximidamide, N,N-diethyl-N'-[(ethoxycarbonylamino)thioxomethyl] and 2-chloromethyl-3-(phenyl)-3H-quinazoline-4-one as otherwise described in Example 154. Yield: 78.94%, M.P. 245-7° C., LC-MS: 469(M+1), Rf: 0.41.

Example 160

[5-(4-Oxo-3-phenyl-3,4-dihydro-quinazolin-2-yl)-4-phenyl-thiazol-2-yl]-carbamic acid methyl ester The title compound was prepared from benzenecarboximidamide, N,N-diethyl-N'-[(methoxycarbonylamino)thioxomethyl] and 2-chloromethyl-3-(phenyl)-3H-quinazoline-4-one as otherwise described in Example 154. Yield: 48.96%, M.P. >275° C., LC-MS: 454(M+1), Rf: 0.48.

Example 161

3-Phenyl-2-(4-phenyl-2-phenylamino-thiazol-5-yl)-3H-quinazolin-4-one

The title compound was prepared from 1-[1-diethylamino-1-phenyl-meth-(E)-ylidene]-3-[(E)-((Z)-1-propenyl)-buta-1,3-dienyl]-thiourea and 2-chloromethyl-3-(phenyl)-3H-quinazoline-4-one as otherwise described in Example 154. Yield: 78.8%, M.P. 181-2° C., LC-MS: 473(M+1), Rf: 0.67.

Example 162

N-[5-(4-Oxo-3-phenyl-3,4-dihydro-quinazoline-2-yl)-4-phenyl-thiazole-2-yl]benzamide The title compound was prepared from 1-Benzoyl-3-[1-diethylamino-1-phenyl-meth-(E)-ylidene]-thiourea and 2-chloromethyl-3-(phenyl)-3H-quinazoline-4-one as otherwise described in Example 154. Yield: 74.6%, M.P. >275, LC-MS: 491(M+1), Rf: 0.70.

Example 163

4-Methyl-N-[5-(4-oxo-3-phenyl-3,4-dihydroquinazolin-2-yl)-4-phenyl-thiazol-2-yl]-benzamide The title compound was prepared from 1-[1-diethylamino-1-phenyl-meth-(E)-ylidene]-3-(4-methyl-benzoyl)-thiourea and 2-chloromethyl-3-(phenyl)-3H-quinazoline-4-one as otherwise described in Example 154. Yield: 69%, M.P. >275° C., LC-MS: 515(M+1), Rf: 0.73

Example 164

2-[2-(1-Furan-2-yl-vinylamino)-4-phenyl-thiazol-5-yl]-3-phenyl-3H-quinazolin-4-one The title compound was prepared from 1-[1-diethylamino-1-phenyl-meth-(E)-ylidene]-3-(furan-2-carbonyl)-thiourea and 2-chloromethyl-3-(phenyl)-3H-quinazoline-4-one as otherwise described in Example 154. Yield: 52.77%, M.P. 271-2° C., LC-MS: 491(M+1), Rf: 0.67.

Example 165

2-[2-(4-Chloro-phenylamino)-4-phenyl-thiazol-5-yl]-3-phenyl-3H-quinazolin-4-one

The title compound was prepared from 1-(4-chloro-phenyl)-3-[1-diethylamino-1-phenyl-meth-(E)-ylidene]-thiourea and 2-chloromethyl-3-(phenyl)-3H-quinazoline-4-one as otherwise described in Example 154. Yield: 60.9%, M.P. >275° C., LC-MS: 507(M+1), Rf: 0.68.

Example 166

[4-Methyl-5-(4-oxo-3-o-tolyl-3,4-dihidro-quinazolin-2-yl)-thiazol-2-yl]-carbamic acid ethyl ester The title compound was prepared from carbamic acid, [{(1-(Diethyl amino)ethylidene) amino}thiaoxomethyl]-ethyl ester and 2-Chloromethyl-3-o-tolyl-3H-quinazoline-4-one as otherwise described in Example 154. Yield: 42.35%, M.P. >275° C., LC-MS: 421(M+1), Rf: 0.61.

Example 167

[4-Methyl-5-(4-oxo-3-o-tolyl-3,4-dihidro-quinazolin-2-yl)-thiazol-2-yl]-carbamic acid methyl ester The title compound was prepared from carbamic acid, [{(1-(Diethyl amino)ethylidene) amino}thiaoxomethyl]-methyl ester and 2-Chloromethyl-3-o-tolyl-3H-quinazoline-4-one as otherwise described in Example 154. Yield: 38.8%, M.P. >275° C., LC-MS: 407(M+1), Rf: 0.70.

Example 168

2-(4-Methyl-2-methylamino-thiazol-5-yl)-3-o-tolyl-3H-quinazolin-4-one

The title compound was prepared from 1-(1-diethylamino-eth-(E)-ylidene)-3-methyl-thiourea and 2-chloromethyl-3-o-tolyl-3H-quinazoline-4-one as otherwise described in Example 154. Yield: 30%, M.P. 218-220° C., LC-MS: 363 (M+1), Rf: 0.63.

Example 169

2-(4-Methyl-2-phenylamino-thiazol-5-yl)-3-o-tolyl-3H-quinazolin-4-one

The title compound was prepared from 1-(1-diethylamino-eth-(E)-ylidene)-3-phenyl-thiourea and 2-chloromethyl-3-o-tolyl-3H-quinazoline-4-one as otherwise described in Example 154. Yield: 48.7%, M.P. 227-228° C., LC-MS: 425 (M+1), Rf: 0.64.

Example 170

2-[2-(4-Chlorophenylamino)-4-methyl-thiazol-5-yl]-3-o-tolyl-3H-quinazolin-4-one

The title compound was prepared from 1-(4-chloro-phenyl)-3-[1-diethylamino-eth-(E)-ylidene]-thiourea and 2-chloromethyl-3-o-tolyl-3H-quinazoline-4-one as otherwise described in Example 154. Yield: 53.9%, M.P. >275° C., LC-MS: 459(M+1), Rf: 0.63.

Example 171

[5-(4-Oxo-3-o-tolyl-3,4-dihydro-quinazol id-2-yl)-4-phenyl-thiazol-2-yl]-carbamic acid ethyl ester The title compound was prepared from benzencarboximidamide, N,N-diethyl-N'-[(ethoxycarbonylamino)thioxomethyl] and 2-Chloromethyl-3-o-tolyl-3H-quinazoline-4-one as otherwise described in Example 154. Yield: 70.5%, M.P. >275, LC-MS: 483(M+1), Rf: 0.68.

Example 172

[5-(4-Oxo-3-o-tolyl-3,4-dihydro-quinazol id-2-yl)-4-phenyl-thiazol-2-yl]-carbamic acid methyl ester The title compound was prepared from benzencarboximidamide, N,N-diethyl-N'-[(methoxycarbonylamino)thioxomethyl] and 2-chloromethyl-3-o-tolyl-3H-quinazoline-4-one as otherwise described in Example 154. Yield: 60%, M.P. >275° C., LC-MS: 469(M+1), Rf: 0.70.

Example 173

2-(2-methylamino-4-phenyl-thiazol-5-yl)-3-o-tolyl-3H-quinazolin-4-one

The title compound was prepared from 1-[1-diethylamino-1-phenyl-meth-(E)-ylidene]-3-methyl-thiourea and 2-chloromethyl-3-o-tolyl-3H-quinazoline-4-one as otherwise described in Example 154. Yield: 24.7%, M.P. 220-5° C., LC-MS: 425(M+1), Rf: 0.62.

Example 174

3-o-Tolyl-2-(4-phenyl-2-phenylamino-thiazol-5-yl)-3H-quinazolin-4-one

The title compound was prepared from 1-[1-diethylamino-1-phenyl-meth-(E)-ylidene]-3-[(E)-((Z)-1-propenyl)-buta-1,3-dienyl]-thiourea and 2-chloromethyl-3-o-tolyl-3H-quinazoline-4-one as otherwise described in Example 154. Yield: 65.7%, M.P. 141-3° C., LC-MS: 487(M+1), Rf: 0.48.

Example 175

N-[5-(4-Oxo-3-o-tolyl-3,4-dihydro-quinazolin-2-yl)-4-phenyl-thiazole-2-yl]benzamide The title compound was prepared from 1-benzoyl-3-[1-diethylamino-1-phenyl-meth-(E)-ylidene]-thiourea and 2-chloromethyl-3-o-tolyl-3H-quinazoline-4-one as otherwise described in Example 154. Yield: 45.14%, M.P. >275° C., LC-MS: 515(M+1), Rf: 0.70.

Example 176

4-Methyl-N-[5-(4-oxo-3-o-tolyl-3,4-dihydroquinazolin-2-yl)-4-phenyl-thiazol-2-yl]-benzamide The title compound was prepared from 1-[1-diethylamino-1-phenyl-meth-(E)-ylidene]-3-(4-methyl-benzoyl)-thiourea and 2-chloromethyl-3-o-tolyl-3H-quinazoline-4-one as otherwise described in Example 154. Yield: 59.3%, M.P. >275° C., LC-MS: 528(M+1), Rf: 0.73.

Example 177

2-[2-(1-Furan-2-yl-vinylamino)-4-phenyl-thiazol-5-yl]-3-o-tolyl-3H-quinazolin-4-one The title compound was prepared from 1-[1-diethylamino-1-phenyl-meth-(E)-ylidene]-3-(furan-2-carbonyl)-thiourea and 2-chloromethyl-3-o-tolyl-3H-quinazoline-4-one as otherwise described in Example 154. Yield: 55.7%, M.P. 262-3° C., LC-MS: 477(M+1), Rf: 0.52.

Example 178

2-[2-(4-Chloro-phenylamino)-4-phenyl-thiazol-5-yl]-3-o-tolyl-3H-quinazolin-4-one The title compound was prepared from 1-(4-chloro-phenyl)-3-[1-diethylamino-1-phenyl-meth-(E)-ylidene]-thiourea and 2-chloromethyl-3-o-tolyl)-3H-quinazoline-4-one as otherwise described in Example 154. Yield: 57.33%, M.P. >275° C., LC-MS: 521(M+1), Rf: 0.70.

Example 179

(4-Methyl-5-(4-oxo-3-m-tolyl-3,4-dihydro-quinazolin-2-yl)-thiazol-2-yl)-carbamic acid ethyl ester The title compound was prepared from carbamic acid, [{(1-(diethyl amino)ethylidene) amino}thiaoxomethyl]-ethyl ester and 2-Chloromethyl-3-m-tolyl-3H-quinazoline-4-one as otherwise described in Example 154. Yield: 38.24%, M.P. 210-1° C., LC-MS: 421(M+1), Rf: 0.57.

Example 180

[4-Methyl-5-(4-oxo-3-m-tolyl-3,4-dihydro-quinazolin-2-yl)-thiazol-2-yl]-carbamic acid methyl ester The title compound was prepared from carbamic acid, [{(1-(Diethyl amino)ethylidene) amino}thiaoxomethyl]-methyl ester and 2-chloromethyl-3-m-tolyl-3H-quinazoline-4-one as otherwise described in Example 154. M.P. 232-3° C., LC-MS: 407(M+1), Rf: 0.48.

Example 181

2-(4-methyl-2-methylamino-thiazol-5-yl)-3-m-tolyl-3H-quinazolin-4-one

The title compound was prepared from 1-(1-diethylamino-eth-(E)-ylidene)-3-methyl-thiourea and 2-chloromethyl-3-m-tolyl-3H-quinazoline-4-one as otherwise described in Example 154. Yield: 30.20%, M.P. >275° C., LC-MS: 363 (M+1), Rf: 0.49.

Example 182

2-(4-Methyl-2-phenylamino-thiazol-5-yl)-3-m-tolyl-3H-quinazolin-4-one

The title compound was prepared from 1-(1-diethylamino-eth-(E)-ylidene)-3-phenyl-thiourea and 2-chloromethyl-3-m-tolyl-3H-quinazoline-4-one as otherwise described in Example 154. Yield: 45.85, M.P. 198-201° C., LC-MS: 425 (M+1), Rf: 0.62

Example 183

2-[2-(4-Chlorophenylamino)-4-methyl-thiazol-5-yl]-3-m-tolyl-3H-quinazolin-4-one

The title compound was prepared from 1-(4-chloro-phenyl)-3-[1-diethylamino-eth-(E)-ylidene]-thiourea and 2-chloromethyl-3-m-tolyl-3H-quinazoline-4-one as otherwise described in Example 154. Yield: 51%, M.P. 236-8° C., LC-MS: 459(M+1), Rf: 0.65.

Example 184

[5-(4-Oxo-3-m-tolyl-3,4-dihydro-quinazolin-2-yl)-4-phenyl-thiazol-2-yl]-carbamic acid ethyl ester The title compound was prepared from benzencarboximi-damide, N,N-diethyl-N'-[(ethoxycarbonylamino)thioxomethyl] and 2-Chloromethyl-3-m-tolyl-3H-quinazoline-4-one as otherwise described in Example 154. Yield: 53.2%, M.P. 261-3° C., LC-MS: 483(M+1), Rf: 0.68.

Example 185

[5-(4-Oxo-3-m-tolyl-3,4-dihydro-quinazolin-2-yl)-4-phenyl-thiazol-2-yl]-carbamic acid methyl ester The title compound was prepared from benzencarboximi-damide, N,N-diethyl-N'-[(methoxycarbonylamino)thioxomethyl] and 2-Chloromethyl-3-m-tolyl-3H-quinazoline-4-one as otherwise described in Example 154. Yield: 51%, M.P. 268-9° C. LC-MS: 469(M+1), Rf: 0.39.

Example 186

2-(2-methylamino-4-phenyl-thiazol-5-yl)-3-m-tolyl-3H-quinazolin-4-one

The title compound was prepared from 1-[1-diethylamino-1-phenyl-meth-(E)-ylidene]-3-methyl-thiourea and 2-chloromethyl-3-m-tolyl-3H-quinazoline-4-one as otherwise described in Example 154. Yield: 46.5%, M.P. 186-7° C. LC-MS: 425(M+1), Rf: 0.40.

Example 187

3-m-Tolyl-2-(4-phenyl-2-phenylamino-thiazol-5-yl)-3H-quinazolin-4-one

The title compound was prepared from 1-[1-Diethylamino-1-phenyl-meth-(E)-ylidene]-3-[(E)-((Z)-1-propenyl)-buta-1,3-dienyl]-thiourea and 2-Chloromethyl-3-m-tolyl-3H-quinazoline-4-one as otherwise described in Example 154. Yield: 59.6%, M.P. 105-7° C. LC-MS: 487(M+1), Rf: 0.42.

Example 188

N-[5-(4-Oxo-3-m-tolyl-3,4-dihydro-quinazolin-2-yl)-4-phenyl-thiazole-2-yl]benzamide The title compound was prepared from 1-benzoyl-3-[1-diethylamino-1-phenyl-meth-(E)-ylidene]-thiourea and 2-chloromethyl-3-m-tolyl-3H-quinazoline-4-one as otherwise described in Example 154. M.P. >275° C., LC-MS: 515(M+1), Rf: 0.53.

Example 189

2-[2-(4-Chloro-phenylamino)-4-phenyl-thiazol-5-yl]-3-m-tolyl-3H-quinazolin-4-one The title compound was prepared from 1-(4-chloro-phenyl)-3-[1-diethylamino-1-phenyl-meth-(E)-ylidene]-thiourea and 2-chloromethyl-3-m-tolyl)-3H-quinazoline-4-one as otherwise described in Example 154. Yield: 42.7%, M.P. 233-5° C. LC-MS: 521(M+1), Rf: 0.61.

Example 190

(4-Methyl-5-(4-oxo-3-p-tolyl-3,4-dihydro-quinazolin-2-yl)-thiazol-2-yl)-carbamic acid ethyl ester The title compound was prepared from carbamic acid, [{(1-(Diethyl amino)ethylidene) amino}thiaoxomethyl]-ethyl ester and 2-Chloromethyl-3-p-tolyl-3H-quinazoline-4-one as otherwise described in Example 154. Yield: 54.11%, M.P. 220-2° C. LC-MS: 421(M+1), Rf: 0.61.

Example 191

2-(4-Methyl-2-phenylamino-thiazol-5-yl)-3-p-tolyl-3H-quinazolin-4-one

The title compound was prepared from 1-(1-diethylamino-eth-(E)-ylidene)-3-phenyl-thiourea and 2-chloromethyl-3-p- tolyl-3H-quinazoline-4-one as otherwise described in Example 154. Yield: 58.6%, M.P. 256-7° C. LC-MS: 425(M+1), Rf: 0.53

Example 192

2-[2-(4-Chlorophenylamino)-4-methyl-thiazol-5-yl]-3-p-tolyl-3H-quinazolin-4-one

The title compound was prepared from 1-(4-chloro-phenyl)-3-[1-diethylamino-eth-(E)-ylidene]-thiourea and 2-chloromethyl-3-p-tolyl-3H-quinazoline-4-one as otherwise described in Example 154. Yield: 40%, M.P. >275° C. LC-MS: 459(M+1), Rf: 0.61.

Example 193

[5-(4-Oxo-3-p-tolyl-3,4-dihydro-quinazolin-2-yl)-4-phenyl-thiazol-2-yl]-carbamic acid ethyl ester The title compound was prepared from benzencarboximidamide, N,N-diethyl-N'-[(ethoxycarbonylamino)thioxomethyl] and 2-chloromethyl-3-p-tolyl-3H-quinazoline-4-one as otherwise described in Example 154. Yield: 55.12%, M.P. >275° C., LC-MS: 483(M+1), Rf: 0.46.

Example 194

[5-(4-Oxo-3-p-tolyl-3,4-dihydro-quinazolin-2-yl)-4-phenyl-thiazol-2-yl]-carbamic acid methyl ester The title compound was prepared from benzencarboximidamide, N,N-diethyl-N'-[(methoxycarbonylamino)thioxomethyl] and 2-chloromethyl-3-p-tolyl-3H-quinazoline-4-one as otherwise described in Example 154. Yield: 55.35%, M.P. >275° C., LC-MS: 469(M+1), Rf: 0.61.

Example 195

2-(2-Methylamino-4-phenyl-thiazol-5-yl)-3-p-tolyl-3H-quinazolin-4-one

The title compound was prepared from 1-[1-diethylamino-1-phenyl-meth-(E)-ylidene]-3-methyl-thiourea and 2-chloromethyl-3-p-tolyl-3H-quinazoline-4-one as otherwise described in Example 154. Yield: 40.6%, M.P: 192-3° C., LC-MS: 425(M+1), Rf: 0.49.

Example 196

3-p-Tolyl-2-(4-phenyl-2-phenylamino-thiazol-5-yl)-3H-quinazolin-4-one

The title compound was prepared from 1-[1-diethylamino-1-phenyl-meth-(E)-ylidene]-3-[(E)-((Z)-1-propenyl)-buta-1,3-dienyl]-thiourea and 2-chloromethyl-3-p-tolyl-3H-quinazoline-4-one as otherwise described in Example 154. Yield: 53.72%, M.P. 225-8° C., LC-MS: 487(M+1), Rf: 0.51.

Example 197

N-[5-(4-Oxo-3-p-tolyl-3,4-dihydro-quinazolin-2-yl)-4-phenyl-thiazole-2-yl]benzamide The title compound was prepared from 1-benzoyl-3-[1-diethylamino-1-phenyl-meth-(E)-ylidene]-thiourea and 2-chloromethyl-3-p-tolyl-3H-quinazoline-4-one as otherwise described in Example 154. M.P. >275° C., LC-MS: 515(M+1), Rf: 0.42.

Example 198

4-Methyl-N-[5-(4-oxo-3-p-tolyl-3,4-dihydroquinazolin-2-yl)-4-phenyl-thiazol-2-yl]-benzamide The title compound was prepared from 1-[1-Diethylamino-1-phenyl-meth-(E)-ylidene]-3-(4-methyl-benzoyl)-thiourea and 2-Chloromethyl-3-p-tolyl-3H-quinazoline-4-one as otherwise described in Example 154. M.P. 217-8° C., LC-MS: 528(M+1), Rf: 0.49.

Example 199

2-[2-(1-Furan-2-yl-vinylamino)-4-phenyl-thiazol-5-yl]-3-p-tolyl-3H-quinazolin-4-one The title compound was prepared from 1-[1-diethylamino-1-phenyl-meth-(E)-ylidene]-3-(furan-2-carbonyl)-thiourea and 2-chloromethyl-3-p-tolyl-3H-quinazoline-4-one as otherwise described in Example 154. Yield: 41.43%, M.P. 231-2° C., LC-MS: 477(M+1), Rf: 0.53

Example 200

2-[2-(4-Chloro-phenylamino)-4-phenyl-thiazol-5-yl]-3-p-tolyl-3H-quinazolin-4-one The title compound was prepared from 1-(4-chloro-phenyl)-3-[1-diethylamino-1-phenyl-meth-(E)-ylidene]-thiourea and 2-chloromethyl-3-p-tolyl)-3H-quinazoline-4-one as otherwise described in Example 154. Yield: 45.33%, M.P. >275° C., LC-MS: 521(M+1), Rf: 0.58

Example 201

{5-[3-(2-Methoxy-phenyl)-4-oxo-3,4-dihydro-quinazolin-yl]-thiazol-2-yl}-carbamic acid ethyl ester The title compound was prepared from carbamic acid, [{(1-(diethyl amino)ethylidene) amino}thiaoxomethyl]-ethyl ester and 2-chloromethyl-3-(2-methoxyphenyl)-3H-quinazoline-4-one as otherwise described in Example 154. Yield: 37.29%, M.P. 263-4° C., LC-MS: 437(M+1), Rf: 0.35

Example 202

2-(4-Methyl-2-phenylamino-thiazol-5-yl)-3-(2-methoxyphenyl)-3H-quinazolin-4-one

The title compound was prepared from 1-(1-diethylamino-eth-(E)-ylidene)-3-phenyl-thiourea and 2-chloromethyl-3-(2-methoxyphenyl)-3H-quinazoline-4-one as otherwise described in Example 154. Yield: 36.58%, M.P. 169-70° C., LC-MS: 441(M+1), Rf: 0.56

Example 203

2-[2-(4-Chlorophenylamino)-4-methyl-thiazol-5-yl]-3-(2-methoxyphenyl)-3H-quinazoline-4-one The title compound was prepared from 1-(4-chloro-phenyl)-3-[1-diethylamino-eth-(E)-ylidene]-thiourea and 2-chloromethyl-3-(2-methoxyphenyl)-3H-quinazoline-4-one as otherwise described in Example 54. Yield: 40.72%, M.P. 225-6° C., LC-MS: 475(M+1), Rf: 0.61

Example 204

[5-(4-Oxo-3-(2-methoxyphenyl)-3,4-dihydro-quinazolin-2-yl)-4-phenyl-thiazol-2-yl]-carbamic acid methyl ester The title compound was prepared from benzencarboximidamide, N,N-diethyl-N'-[(methoxycarbonylamino)thioxom ethyl] and 2-chloromethyl-3-(2-methoxyphenyl)-3H-quinazoline-4-one as otherwise described in Example 154. M.P. 228-30° C., LC-MS: 485(M+1), Rf: 0.50

Example 205

2-(2-Methylamino-4-phenyl-thiazol-5-yl)-3-(2-methoxyphenyl)-3H-quinazolin-4-one

The title compound was prepared from 1-[1-diethylamino-1-phenyl-meth-(E)-ylidene]-3-methyl-thiourea and 2-chloromethyl-3-(2-methoxyphenyl)l-3H-quinazoline-4-one as otherwise described in Example 154. Yield: 35.6%, M.P. 241-3° C., LC-MS: 441(M+1), Rf: 0.70

Example 206

3-(2-Methoxyphenyl)-2-(4-phenyl-2-phenylamino-thiazol-5-yl)-3H-quinazolin-4-one

The title compound was prepared from 1-[1-diethylamino-1-phenyl-meth-(E)-ylidene]-3-[(E)-((Z)-1-propenyl)-buta-1,3-dienyl]-thiourea and 2-chloromethyl-3-(2-methoxyphenyl)-3H-quinazoline-4-one as otherwise described in Example 154. Yield: 52.66%, M.P. 224-5° C., LC-MS: 563 (M+1), Rf: 0.62

Example 207

{5-[3-(4-Methoxy-phenyl)-4-oxo-3,4-dihydro-quinazolin-yl]-thiazol-2-yl}-carbamic acid ethyl ester The title compound was prepared from carbamic acid, [{(1-(diethyl amino)ethylidene) amino}thiaoxomethyl]-ethyl ester and 2-chloromethyl-3-(4-methoxyphenyl)-3H-quinazoline-4-one as otherwise described in Example 201. Yield: 44.1%, M.P. 222-4° C., LC-MS: 437(M+1), Rf: 0.66

Example 208

2-[2-(4-Chloro-phenylamino)-4-phenyl-thiazol-5-yl]-3-(2-methoxyphenyl)-3H-quinazolin-4-one The title compound was prepared from 1-(4-chloro-phenyl)-3-[1-diethylamino-1-phenyl-meth-(E)-ylidene]-thiourea and 2-chloromethyl-3-(2-methoxyphenyl)-3H-quinazoline-4-one as otherwise described in Example 154. Yield: 50.32%, M.P. 230-2° C., LC-MS: 537(M+1), Rf: 0.62

Example 209

{5-[3-(3-Methoxy-phenyl)-4-oxo-3,4-dihydro-quinazolin-yl]-thiazol-2-yl}-carbamic acid ethyl ester The title compound was prepared from carbamic acid, [{(1-(diethyl amino)ethylidene) amino}thiaoxomethyl]-ethyl ester and 2-chloromethyl-3-(3-methoxyphenyl)-3H-quinazoline-4-one as otherwise described in Example 154. Yield: 46.89%, M.P. 235-6° C., LC-MS: 438(M+1), Rf: 0.34

Example 210

2-(4-Methyl-2-phenylamino-thiazol-5-yl)-3-(3-methoxyphenyl)-3H-quinazolin-4-one

The title compound was prepared from 1-(1-diethylamino-eth-(E)-ylidene)-3-phenyl-thiourea and 2-chloromethyl-3-(3-methoxyphenyl)-3H-quinazoline-4-one as otherwise described in Example 154. Yield: 46.34%, M.P. >275° C., LC-MS: 441(M+1), Rf: 0.38

Example 211

2-[2-(4-Chlorophenylamino)-4-methyl-thiazol-5-yl]-3-(3-methoxyphenyl)-3H-quinazolin-4-one The title compound was prepared from 1-(4-chloro-phenyl)-3-[1-diethylamino-eth-(E)-ylidene]-thiourea and 2-chloromethyl-3-(3-methoxyphenyl)-3H-quinazoline-4-one as otherwise described in Example 154. M.P. 243-4° C., LC-MS: 475(M+1), Rf: 0.42

Example 212

[5-(4-Oxo-3-(3-methoxyphenyl)-3,4-dihydro-quinazolin-2-yl)-4-phenyl-thiazol-2-yl]-carbamic acid ethyl ester The title compound was prepared from benzencarboximidamide, N,N-diethyl-N'-[(ethoxycarbonylamino)thioxomethyl] and 2-chloromethyl-3-(3-methoxyphenyl)-3H-quinazoline-4-one as otherwise described in Example 154. Yield: 49.1%, M.P. 204-5° C., LC-MS: 499(M+1), Rf: 0.50

Example 213

3-(3-methoxyphenyl)-2-(4-phenyl-2-phenylamino-thiazol-5-yl)-3H-quinazolin-4-one

The title compound was prepared from 1-[1-diethylamino-1-phenyl-meth-(E)-ylidene]-3-[(E)-((Z)-1-propenyl)-buta-1,3-dienyl]-thiourea and 2-chloromethyl-3-(3-methoxyphenyl)-3H-quinazoline-4-one as otherwise described in Example 154. Yield: 48.52%, M.P. 250-52° C., LC-MS: 503 (M+1), Rf: 0.47

Example 214

N-[5-(4-Oxo-3-(3-methoxyphenyl)-3,4-dihydro-quinazolin-2-yl)-4-phenyl-thiazole-2-yl]benzamide The title compound was prepared from 1-benzoyl-3-[1-diethylamino-1-phenyl-meth-(E)-ylidene]-thiourea and 2-chloromethyl-3-(3-methoxyphenyl)l-3H-quinazoline-4-one as otherwise described in Example 154. M.P. 195-6° C., LC-MS: 531(M+1), Rf: 0.45

Example 215

{5-[3-(4-Methoxy-phenyl)-4-oxo-3,4-dihydro-quinazolin-yl]-thiazol-2-yl}-carbamic acid ethyl ester The title compound was prepared from Carbamic acid, [{(1-(diethyl amino)ethylidene) amino}thiaoxomethyl]-ethyl ester and 2-Chloromethyl-3-(4-methoxyphenyl)-3H-quinazoline-4-one as otherwise described in Example 154. Yield: 44.1%, M.P. >275° C., LC-MS: 437(M+1), Rf: 0.30

Example 216

2-(4-Methyl-2-phenylamino-thiazol-5-yl)-3-(4-methoxyphenyl)-3H-quinazolin-4-one

The title compound was prepared from 1-(1-diethylamino-eth-(E)-ylidene)-3-phenyl-thiourea and 2-chloromethyl-3-(4-methoxyphenyl)-3H-quinazoline-4-one as otherwise described in Example 154. Yield: 45.12%, M.P. 265-6° C., LC-MS: 441(M+1), Rf: 0.45

Example 217

2-[2-(4-Chlorophenylamino)-4-methyl-thiazol-5-yl]-3-(4-methoxyphenyl)-3H-quinazolin-4-one The title compound was prepared from 1-(4-chloro-phenyl)-3-[1-diethylamino-eth-(E)-ylidene]-thiourea and 2-chloromethyl-3-(4-methoxyphenyl)-3H-quinazoline-4-one as otherwise described in Example 154. Yield: 38.32%, M.P. >275, LC-MS: 475(M+1), Rf: 0.70

Example 218

[5-(4-Oxo-3-(4-methoxyphenyl)-3,4-dihydro-quinazolin-2-yl)-4-phenyl-thiazol-2-yl]-carbamic acid ethyl ester The title compound was prepared from benzencarboximidamide, N,N-diethyl-N'-[(ethoxycarbonylamino)thioxomethyl] and 2-chloromethyl-3-(4-methoxyphenyl)-3H-quinazoline-4-one as otherwise described in Example 154. Yield: 45.96%, M.P. 256-7° C., LC-MS: 499(M+1), Rf: 0.65

Example 219

[5-(4-Oxo-3-(4-methoxyphenyl)-3,4-dihydro-quinazolin-2-yl)-4-phenyl-thiazol-2-yl]-carbamic acid methyl ester The title compound was prepared from benzencarboximidamide, N,N-diethyl-N'-[(methoxycarbonylamino)thioxomethyl] and 2-chloromethyl-3-(4-methoxyphenyl)-3H-quinazoline-4-one as otherwise described in Example 154. Yield: 43.63%, M.P. 272-4° C., LC-MS: 485(M+1), Rf: 0.71

Example 220

2-(2-Methylamino-4-phenyl-thiazol-5-yl)-3-(4-methoxyphenyl)-3H-quinazolin-4-one

The title compound was prepared from 1-[1-diethylamino-1-phenyl-meth-(E)-ylidene]-3-methyl-thiourea and 2-chloromethyl-3-(4-methoxyphenyl)l-3H-quinazoline-4-one as otherwise described in Example 154. Yield: 38.98%, M.P. 235-6° C., LC-MS: 441(M+1), Rf: 0.62

Example 221

3-(4-Methoxyphenyl)-2-(4-phenyl-2-phenylamino-thiazol-5-yl)-3H-quinazolin-4-one

The title compound was prepared from 1-[1-diethylamino-1-phenyl-meth-(E)-ylidene]-3-[(E)-((Z)-1-propenyl)-buta-1,3-dienyl]-thiourea and 2-chloromethyl-3-(4-methoxyphenyl)-3H-quinazoline-4-one as otherwise described in Example 154. Yield: 48.52%, M.P. 135-7° C., LC-MS: 503 (M+1), Rf: 0.58

Example 222

N-[5-(4-Oxo-3-(4-methoxyphenyl)-3,4-dihydro-quinazolin-2-yl)-4-phenyl-thiazole-2-yl]benzamide The title compound was prepared from 1-benzoyl-3-[1-diethylamino-1-phenyl-meth-(E)-ylidene]-thiourea and 2-chloromethyl-3-(4-methoxyphenyl)-3H-quinazoline-4-one as otherwise described in Example 154. Yield: 56.76%, M.P. >275° C., LC-MS: 531(M+1), Rf: 0.61

Example 223

4-Methyl-N-[5-(4-oxo-3-(4-methoxyphenyl)-3,4-dihydro-quinazolin-2-yl)-4-phenyl-thiazol-2-yl]-benzamide The title compound was prepared from 1-[1-diethylamino-1-phenyl-meth-(E)-ylidene]-3-(4-methyl-benzoyl)-thiourea and 2-chloromethyl-3-(4-methoxyphenyl)-3H-quinazoline-4-one as otherwise described in Example 154. Yield: 52.66%, M.P. >/275° C., LC-MS: 544(M+1), Rf: 0.68

Example 224

2-[2-(1-Furan-2-yl-vinylamino)-4-phenyl-thiazol-5-yl]-3-(4-methoxyphenyl)-3H-quinazolin-4-one The title compound was prepared from 1-[1-diethylamino-1-phenyl-meth-(E)-ylidene]-3-(furan-2-carbonyl)-thiourea and 2-chloromethyl-3-(4-methoxyphenyl)-3H-quinazoline-4-one as otherwise described in Example 154. Yield: 46.21%, M.P. 262-4° C., LC-MS: 493(M+1), Rf: 0.63

Example 225

2-[2-(4-Chloro-phenylamino)-4-phenyl-thiazol-5-yl]-3-(4-methoxyphenyl)-3H-quinazolin-4-one The title compound was prepared from 1-(4-chloro-phenyl)-3-[1-diethylamino-1-phenyl-meth-(E)-ylidene]-thiourea and 2-chloromethyl-3-(4-methoxyphenyl)-3H-quinazoline-4-one as otherwise described in Example 154. Yield: 50.32%, M.P. 220-1° C., LC-MS: 537(M+1), Rf: 0.58

Example 226

(4-Methyl-5-(4-oxo-3-(2-Chloro-phenyl)-3,4-dihydro-quinazolin-2-yl)-thiazol-2-yl)-carbamic acid ethyl ester The title compound was prepared from carbamic acid, [{(1-(diethyl amino)ethylidene) amino}thiaoxomethyl]-ethyl ester (1 gm, 0.001 mole) and 2-chloromethyl-3-(2-chloro-phenyl)-3H-quinazoline-4-one as otherwise described in Example 154. Yield: 43.57%, M.P. 246-7° C., LC-MS: 442(M+1), Rf: 0.50

Example 227

(4-Methyl-5-(4-oxo-3-(2-Chloro-phenyl)-3,4-dihydro-quinazolin-2-yl)-thiazol-2-yl)-carbamic acid methyl ester The title compound was prepared from carbamic acid, [{(1-(diethyl amino)ethylidene) amino}thiaoxomethyl]-methyl ester and 2-chloromethyl-3-(2-chloro-phenyl)-3H-quinazoline-4-one as otherwise described in Example 154. Yield: 41.30%, M.P. 243-5° C., LC-MS: 428(M+1), Rf: 0.40

Example 228

2-(4-Methyl-2-methylamino-thiazol-5-yl)-3-(2-chloro-phenyl)-3H-quinazolin-4-one

The title compound was prepared from 1-(1-diethylamino-eth-(E)-ylidene)-3-methyl-thiourea and 2-chloromethyl-3-(2-chloro-phenyl)-3H-quinazoline-4-one as otherwise described in Example 154. Yield: 34%, M.P. 214-5° C., LC-MS: 384(M+1), Rf: 0.30

Example 229

2-(4-Methyl-2-phenylamino-thiazol-5-yl)-3-(2-chloro-phenyl)-3H-quinazolin-4-one

The title compound was prepared from 1-(1-diethylamino-eth-(E)-ylidene)-3-phenyl-thiourea and 2-chloromethyl-3-(2-chloro-phenyl)-3H-quinazoline-4-one as otherwise described in Example 154. M.P. 228-9° C., LC-MS: 446(M+1), Rf 0.40

Example 230

2-[2-(4-Chlorophenylamino)-4-methyl-thiazol-5-yl]-3-(2-chloro-phenyl)-3H-quinazolin-4-one The title compound was prepared from 1-(4-chloro-phenyl)-3-[1-diethylamino-eth-(E)-ylidene]-thiourea and 2-chloromethyl-3-(2-chloro-phenyl)-3H-quinazoline-4-one as otherwise described in Example 154. M.P. 237-8° C., LC-MS: 480(M+1), Rf: 0.51

Example 231

[5-(4-Oxo-3-(2-chloro-phenyl)-3,4-dihydro-quinazolin-2-yl)-4-phenyl-thiazol-2-yl]-carbamic acid ethyl ester The title compound was prepared from benzencarboximidamide, N,N-diethyl-N'-[(ethoxycarbonylamino)thioxomethyl] and 2-chloromethyl-3-(2-chloro-phenyl)-3H-quinazoline-4-one as otherwise described in Example 154. Yield: 50.30%, M.P. 236-8° C., LC-MS: 504(M+1), Rf: 0.66

Example 232

[5-(4-Oxo-3-(2-chloro-phenyl)-3,4-dihydro-quinazolin-2-yl)-4-phenyl-thiazol-2-yl]-carbamic acid methyl ester The title compound was prepared from benzencarboximidamide, N,N-diethyl-N'-[(methoxycarbonylamino)thioxomethyl] and 2-chloromethyl-3-(2-chloro-phenyl)-3H-quinazoline-4-one as otherwise described in Example 154. Yield: 46.98%, M.P. >275° C., LC-MS: 490(M+1), Rf: 0.60

Example 233

2-(2-Methylamino-4-phenyl-thiazol-5-yl)-3-(2-Chloro-phenyl)-3H-quinazolin-4-one

The title compound was prepared from 1-[1-diethylamino-1-phenyl-meth-(E)-ylidene]-3-methyl-thiourea and 2-chloromethyl-3-(2-chloro-phenyl)l-3H-quinazoline-4-one as otherwise described in Example 154. Yield: 41.34%, M.P. 215-7° C., LC-MS: 446(M+1), Rf: 0.60

Example 234

3-(2-Chloro-phenyl)-2-(4-phenyl-2-phenylamino-thiazol-5-yl)-3H-quinazolin-4-one

The title compound was prepared from 1-[1-diethylamino-1-phenyl-meth-(E)-ylidene]-3-[(E)-((Z)-1-propenyl)-buta-1,3-dienyl]-thiourea and 2-chloromethyl-(2-chloro-phenyl)-3H-quinazoline-4-one as otherwise described in Example 154. Yield: 54.25%, M.P. 210-12° C., LC-MS: 508(M+1), Rf: 0.65

Example 235

N-[5-(4-Oxo-3-(2-chloro-phenyl)-3,4-dihydro-quinazolin-2-yl)-4-phenyl-thiazole-2-yl]benzamide The title compound was prepared from 1-benzoyl-3-[1-diethylamino-1-phenyl-meth-(E)-ylidene]-thiourea and 2-chloromethyl-3-(2-chloro-phenyl)-3H-quinazoline-4-one as otherwise described in Example 154. Yield: 56%, M.P. 212-4° C., LC-MS: 536(M+1), Rf: 0.74

Example 236

4-Methyl-N-[5-(4-oxo-3-(2-chloro-phenyl)-3,4-dihydro-quinazolin-2-yl)-4-phenyl-thiazol-2-yl]-benzamide The title compound was prepared from 1-[1-diethylamino-1-phenyl-meth-(E)-ylidene]-3-(4-methyl-benzoyl)-thiourea and 2-chloromethyl-(2-chloro-phenyl)-3H-quinazoline-4-one as otherwise described in Example 154. Yield: 52.31%, M.P. >275° C., LC-MS: 549(M+1), Rf: 0.77

Example 237

2-[2-(1-Furan-2-yl-vinylamino)-4-phenyl-thiazol-5-yl]-3-(2-chloro-phenyl)-3H-quinazolin-4-one The title compound was prepared from 1-[1-diethylamino-1-phenyl-meth-(E)-ylidene]-3-(furan-2-carbonyl)-thiourea and 2-chloromethyl-3-(2-chloro-phenyl)l-3H-quinazoline-4-one as otherwise described in Example 154. Yield: 53.1%, M.P. >275° C., LC-MS: 498(M+1), Rf: 0.72

Example 238

2-[2-(4-Chlorophenylamino)-4-phenyl-thiazol-5-yl]-3-(2-Chloro-phenyl)l-3H-quinazolin-4-one The title compound was prepared from 1-(4-chloro-phenyl)-3-[1-diethylamino-1-phenyl-meth-(E)-ylidene]-thiourea and 2-chloromethyl-3-(2-chloro-phenyl)-3H-quinazoline-4-one as otherwise described in Example 154. Yield: 51.28%, M.P. 242-3° C., LC-MS: 542(M+1), Rf: 0.77

Example 239

(4-Methyl-5-(4-oxo-3-(3-chloro-phenyl)-3,4-dihydro-quinazolin-2-yl)-thiazol-2-yl)-carbamic acid ethyl ester The title compound was prepared from carbamic acid, [{(1-(diethyl amino)ethylidene) amino}thiaoxomethyl]-ethyl ester (1 g, 1 mmol) and 2-chloromethyl-3-(3-chloro-phenyl)-3H-quinazoline-4-one as otherwise described in Example 154. M.P. 262-3° C., LC-MS: 442(M+1), Rf: 0.48

Example 240

[5-(4-Oxo-3-(3-Chloro-phenyl)-3,4-dihydro-quinazolin-2-yl)-4-phenyl-thiazol-2-yl]-carbamic acid ethyl ester The title compound was prepared from benzencarboximidamide, N,N-diethyl-N'-[(ethoxycarbonylamino)thioxomethyl] and 2-chloromethyl-3-(3-chloro-phenyl)-3H-quinazoline-4-one as otherwise described in Example 154. Yield: 47.85%, M.P. 235-6° C., LC-MS: 504(M+1), Rf: 0.52

Example 241

[5-(4-Oxo-3-(3-chloro-phenyl)-3,4-dihydro-quinazolin-2-yl)-4-phenyl-thiazol-2-yl]-carbamic acid methyl ester The title compound was prepared from benzencarboximidamide, N,N-diethyl-N'-[(methoxycarbonylamino)thioxomethyl] and 2-chloromethyl-3-(3-chloro-phenyl)-3H-quinazoline-4-one as otherwise described in Example 154. M.P. 230-1° C., LC-MS: 490(M+1), Rf: 0.61

Example 242

(4-Methyl-5-(4-oxo-3-(4-chloro-phenyl)-3,4-dihydro-quinazolin-2-yl)-thiazol-2-yl)-carbamic acid ethyl ester The title compound was prepared from carbamic acid, [{(1-(diethyl amino)ethylidene) amino}thiaoxomethyl]-ethyl ester (1 g, 1 mmol) and 2-chloromethyl-3-(4-chloro-phenyl)-3H-quinazoline-4-one as otherwise described in Example 154. Yield: 45.81%, M.P. >275° C., LC-MS: 442 (M+1), Rf: 0.56

Example 243

(4-Methyl-5-(4-oxo-3-(4-Chloro-phenyl)-3,4-dihydro-quinazolin-2-yl)-thiazol-2-yl)-carbamic acid methyl ester The title compound was prepared from carbamic acid, [{(1-(diethyl amino)ethylidene) amino}thiaoxomethyl]-methyl ester and 2-chloromethyl-3-(4-chloro-phenyl)-3H-quinazoline-4-one as otherwise described in Example 154. Yield: 42.93%, M.P. >275° C., LC-MS: 428(M+1), Rf: 0.58

Example 244

2-(4-Methyl-2-methylamino-thiazol-5-yl)-3-(4-chloro-phenyl)-3H-quinazolin-4-one

The title compound was prepared from 1-(1-diethylamino-eth-(E)-ylidene)-3-methyl-thiourea and 2-chloromethyl-3-(4-chloro-phenyl)-3H-quinazoline-4-one as otherwise described in Example 154. Yield: 41%, M.P. 195-7° C., LC-MS: 484(M+1), Rf: 0.61

Example 245

2-(4-Methyl-2-phenylamino-thiazol-5-yl)-3-(4-chloro-phenyl)-3H-quinazolin-4-one

The title compound was prepared from 1-(1-diethylamino-eth-(E)-ylidene)-3-phenyl-thiourea and 2-chloromethyl-3-(4-chloro-phenyl)-3H-quinazoline-4-one as otherwise described in Example 154. Yield: 50.64%, M.P. >275, LC-MS: 446(M+1), Rf: 0.54

Example 246

2-[2-(4-Chlorophenylamino)-4-methyl-thiazol-5-yl]-3-(4-chloro-phenyl)-3H-quinazolin-4-one The title compound was prepared from 1-(4-chloro-phenyl)-3-[1-diethylamino-eth-(E)-ylidene]-thiourea and 2-chloromethyl-3-(4-chloro-phenyl)-3H-quinazoline-4-one as otherwise described in Example 154. Yield: 43.79%, M.P. 267-8° C., LC-MS: 480(M+1), Rf: 0.52

Example 247

2-[2-(4-Methylphenylamino)-4-methyl-thiazol-5-yl]-3-(4-chloro-phenyl)-3H-quinazolin-4-one The title compound was prepared from 1-(4-methyl-phenyl)-3-[1-diethylamino-eth-(E)-ylidene]-thiourea and 2-chloromethyl-3-(4-chloro-phenyl)-3H-quinazoline-4-one as otherwise described in Example 154. Yield: 50.34%, M.P. >275° C., LC-MS: 498.5(M+1), Rf: 0.48

Example 248

2-[2-(4-Methoxyl-phenylamino)-4-methyl-thiazol-5-yl]-3-(4-chloro-phenyl)-3H-quinazolin-4-one The title compound was prepared from 1-(4-methoxyl-phenyl)-3-[1-diethylamino-eth-(E)-ylidene]-thiourea and 2-chloromethyl-3-(4-chloro-phenyl)-3H-quinazoline-4-one as otherwise described in Example 154. Yield: 38.46%, M.P. >275° C., LC-MS: 542(M+1), Rf: 0.56

Example 249

[5-(4-Oxo-3-(4-Chloro-phenyl)-3,4-dihydro-quinazolin-2-yl)-4-phenyl-thiazol-2-yl]-carbamic acid ethyl ester The title compound was prepared from benzencarboximidamide, N,N-diethyl-N'-[(ethoxycarbonylamino)thioxomethyl] and 2-chloromethyl-3-(4-chloro-phenyl)-3H-quinazoline-4-one as otherwise described in Example 154. Yield: 50.31%, M.P. >275° C., LC-MS: 504(M+1), Rf: 0.62

Example 250

[5-(4-Oxo-3-(4-Chloro-phenyl)-3,4-dihydro-quinazolin-2-yl)-4-phenyl-thiazol-2-yl]-carbamic acid methyl ester The title compound was prepared from benzencarboximidamide, N,N-diethyl-N'-[(methoxycarbonylamino)thioxomethyl] and 2-chloromethyl-3-(4-chloro-phenyl)-3H-quinazoline-4-one as otherwise described in Example 154. Yield: 48.8%, M.P. >275° C., LC-MS: 490(M+1), Rf: 0.57

Example 251

2-(2-Methylamino-4-phenyl-thiazol-5-yl)-3-(4-Chloro-phenyl)-3H-quinazolin-4-one

The title compound was prepared from 1-[1-diethylamino-1-phenyl-meth-(E)-ylidene]-3-methyl-thiourea and 2-chloromethyl-3-(4-chloro-phenyl)l-3H-quinazoline-4-one as otherwise described in Example 154. Yield: 44.7%, M.P. >275° C., LC-MS: 446(M+1), Rf: 0.61

Example 252

3-(4-Chloro-phenyl)-2-(4-phenyl-2-phenylamino-thiazol-5-yl)-3H-quinazolin-4-one

The title compound was prepared from 1-[1-diethylamino-1-phenyl-meth-(E)-ylidene]-3-[(E)-((Z)-1-propenyl)-buta-1,3-dienyl]-thiourea and 2-chloromethyl-(4-chloro-phenyl)-3H-quinazoline-4-one as otherwise described in Example 154. Yield: 52.94%, M.P. 218-22° C., LC-MS: 508(M+1), Rf: 0.64

Example 253

N-[5-(4-Oxo-3-(4-Chloro-phenyl)-3,4-dihydro-quinazolin-2-yl)-4-phenyl-thiazole-2-yl]benzamide The title compound was prepared from 1-Benzoyl-3-[1-diethylamino-1-phenyl-meth-(E)-ylidene]-thiourea and 2-chloromethyl-3-(4-chloro-phenyl)-3H-quinazoline-4-one as otherwise described in Example 154. Yield: 53.33%, M.P. >275° C., LC-MS: 536(M+1), Rf: 0.54

Example 254

4-Methyl-N-[5-(4-oxo-3-(4-Chloro-phenyl)-3,4-dihydro-quinazolin-2-yl)-4-phenyl-thiazol-2-yl]-benzamide The title compound was prepared from 1-[1-diethylamino-1-phenyl-meth-(E)-ylidene]-3-(4-methyl-benzoyl)-thiourea and 2-chloromethyl-(4-chloro-phenyl)-3H-quinazoline-4-one as otherwise described in Example 154. Yield: 50.33%, M.P. >275° C., LC-MS: 549(M+1), Rf: 0.59

Example 255

2-[2-(1-Furan-2-yl-vinylamino)-4-phenyl-thiazol-5-yl]-3-(4-Chloro-phenyl)-3H-quinazolin-4-one The title compound was prepared from 1-[1-diethylamino-1-phenyl-meth-(E)-ylidene]-3-(furan-2-carbonyl)-thiourea and 2-chloromethyl-3-(4-chloro-phenyl)l-3H-quinazoline-4-one as otherwise described in Example 154. Yield: 53.34%, M.P. 270-4° C., LC-MS: 498(M+1), Rf: 0.62

Example 256

2-[2-(4-Chloro-phenylamino)-4-phenyl-thiazol-5-yl]-3-(4-Chloro-phenyl)-3H-quinazolin-4-one The title compound was prepared from 1-(4-chloro-phenyl)-3-[1-diethylamino-1-phenyl-meth-(E)-ylidene]-thiourea and 2-chloromethyl-3-(4-chloro-phenyl)-3H-quinazoline-4-one as otherwise described in Example 154. Yield: 38.46%, M.P. 271-2° C., LC-MS: 542(M+1), Rf: 0.64

Example 257

2-[2-(4-Methyl-phenylamino)-4-phenyl-thiazol-5-yl]-3-(4-Chloro-phenyl)-3H-quinazolin-4-one The title compound was prepared from 1-(4-methyl-phenyl)-3-[1-diethylamino-1-phenyl-meth-(E)-ylidene]-thiourea and 2-chloromethyl-3-(4-chloro-phenyl)-3H-quinazoline-4-one as otherwise described in Example 154. Yield: 48.52%, M.P. 225-7° C., LC-MS: 497(M+1), Rf: 0.61

Example 258

2-[2-(4-Methoxyl-phenylamino)-4-phenyl-thiazol-5-yl]-3-(4-Chloro-phenyl)-3H-quinazolin-4-one The title compound was prepared from 1-(4-methoxyl-phenyl)-3-[1-diethylamino-1-phenyl-meth-(E)-ylidene]-thiourea and 2-chloromethyl-3-(4-chloro-phenyl)-3H-quinazoline-4-one as otherwise described in Example 154. Yield: 43.96%, M.P. 262-3° C., LC-MS: 453 (M+1), Rf: 0.59

Example 259

(4-Methyl-5-(4-oxo-3-(4-acetyl-phenyl)-3,4-dihydro-quinazolin-2-yl)-thiazol-2-yl)-carbamic acid ethyl ester The title compound was prepared from carbamic acid, [{(1-(diethyl amino)ethylidene) amino}thiaoxomethyl]-ethyl ester (1 g, 1 mmol) and 2-chloromethyl-3-(4-acetyl-phenyl)-3H-quinazoline-4-one as otherwise described in Example 154. Yield: 47.25%, M.P. >275° C., LC-MS: 449 (M+1), Rf: 0.61

Example 260

(4-Methyl-5-(4-oxo-3-(4-acetyl-phenyl)-3,4-dihydro-quinazolin-2-yl)-thiazol-2-yl)-carbamic acid methyl ester The title compound was prepared from carbamic acid, [{(1-(diethyl amino)ethylidene)amino}thiaoxomethyl]-methylester and 2-chloromethyl-3-(4-acetyl-phenyl)-3H-quinazoline-4-one as otherwise described in Example 154. Yield: 44.9%, M.P. 232-4° C., LC-MS: 435(M+1), Rf: 0.47

Example 261

2-(4-Methyl-2-methylamino-thiazol-5-yl)-3-(4-acetyl-phenyl)-3H-quinazolin-4-one

The title compound was prepared from 1-(1-diethylamino-eth-(E)-ylidene)-3-methyl-thiourea and 2-chloromethyl-3-(4-acetyl-phenyl)-3H-quinazoline-4-one as otherwise described in Example 154. Yield: 29.52%, M.P. 245-6° C., LC-MS: 391(M+1), Rf: 0.46.

Example 262

2-(4-Methyl-2-phenylamino-thiazol-5-yl)-3-(4-acetyl-phenyl)-3H-quinazolin-4-one

The title compound was prepared from 1-(1-diethylamino-eth-(E)-ylidene)-3-phenyl-thiourea and 2-chloromethyl-3-(4-acetyl-phenyl)-3H-quinazoline-4-one as otherwise described in Example 154. Yield: 48.21%, M.P. 271-3° C., LC-MS: 453(M+1), Rf: 0.51.

Example 263

2-[2-(4-Chlorophenylamino)-4-methyl-thiazol-5-yl]-3-(4-acetyl-phenyl)-3H-quinazolin-4-one The title compound was prepared from 1-(4-chloro-phenyl)-3-[1-diethylamino-eth-(E)-ylidene]-thiourea and 2-chloromethyl-3-(4-acetyl-phenyl)-3H-quinazoline-4-one as otherwise described in Example 154. Yield: 43.27%, M.P. 209-1° C., LC-MS: 487(M+1), Rf: 0.52

Example 264

[5-(4-Oxo-3-(4-acetyl-phenyl)-3,4-dihydro-quinazolin-2-yl)-4-phenyl-thiazol-2-yl]-carbamic acid ethyl ester The title compound was prepared from benzencarboximidamide, N,N-diethyl-N'-[(ethoxycarbonylamino)thioxomethyl] and 2-chloromethyl-3-(4-acetyl-phenyl)-3H-quinazoline-4-one as otherwise described in Example 154. Yield: 50.60%, M.P. 245-7° C., LC-MS: 511(M+1), Rf: 0.58.

Example 265

[5-(4-Oxo-3-(4-acetyl-phenyl)-3,4-dihidro-quinazolin-2-yl)-4-phenyl-thiazol-2-yl]-carbamic acid methyl ester The title compound was prepared from benzencarboximidamide, N,N-diethyl-N'-[(methoxycarbonylamino)thioxomethyl] and 2-chloromethyl-3-(4-acetyl-phenyl)-3H-quinazoline-4-one as otherwise described in Example 154. Yield: 48.52%, M.P. 203-4° C., LC-MS: 497(M+1), Rf: 0.56

Example 266

2-(2-Methylamino-4-phenyl-thiazol-5-yl)-3-(4-acetyl-phenyl)-3H-quinazolin-4-one

The title compound was prepared from 1-[1-diethylamino-1-phenyl-meth-(E)-ylidene]-3-methyl-thiourea and 2-chloromethyl-3-(4-acetyl-phenyl)1-3H-quinazoline-4-one as otherwise described in Example 154. Yield: 43.96%, M.P. 239-40° C., LC-MS: 453(M+1), Rf: 0.53

Example 267

3-(4-acetyl-phenyl)-2-(4-phenyl-2-phenylamino-thiazol-5-yl)-3H-quinazolin-4-one

The title compound was prepared from 1-[1-diethylamino-1-phenyl-meth-(E)-ylidene]-3-[(E)-((Z)-1-propenyl)-buta-1,3-dienyl]-thiourea and 2-chloromethyl-(4-acetyl-phenyl)-3H-quinazoline-4-one as otherwise described in Example 154. Yield: 50.32%, M.P. 223-5° C., LC-MS: 515(M+1), Rf: 0.61.

Example 268

N-[5-(4-Oxo-3-(4-acetyl-phenyl)-3,4-dihydro-quinazolin-2-yl)-4-phenyl-thiazole-2-yl]benzamide The title compound was prepared from 1-benzoyl-3-[1-diethylamino-1-phenyl-meth-(E)-ylidene]-thiourea and 2-chloromethyl-3-(4-acetyl-phenyl)-3H-quinazoline-4-one as otherwise described in Example 154. Yield: 50.33%, M.P. 250-2° C., LC-MS: 543(M+1), Rf: 0.70

Example 269

4-Methyl-N-[5-(4-oxo-3-(4-acetyl-phenyl)-3,4-dihydro-quinazolin-2-yl)-4-phenyl-thiazol-2-yl]-benzamide The title compound was prepared from 1-[1-diethylamino-1-phenyl-meth-(E)-ylidene]-3-(4-methyl-benzoyl)-thiourea and 2-chloromethyl-(4-acetyl-phenyl)-3H-quinazoline-4-one as otherwise described in Example 154. Yield: 48.37%, M.P. 266-7° C., LC-MS: 556(M+1), Rf: 0.62.

Example 270

2-[2-(1-Furan-2-yl-vinylamino)-4-phenyl-thiazol-5-yl]-3-(4-acetyl-phenyl)-3H-quinazolin-4-one The title compound was prepared from 1-[1-diethylamino-1-phenyl-meth-(E)-ylidene]-3-(furan-2-carbonyl)-thiourea and 2-chloromethyl-3-(4-acetyl-phenyl)l-3H-quinazoline-4-one as otherwise described in Example 154. Yield: 45.64%, M.P. 232-3° C., LC-MS: 505(M+1), Rf: 0.40.

Example 271

2-[2-(4-Chlorophenylamino)-4-phenyl-thiazol-5-yl]-3-(4-acetyl-phenyl)-3H-quinazolin-4-one The title compound was prepared from 1-(4-chloro-phenyl)-3-[1-diethylamino-1-phenyl-meth-(E)-ylidene]-thiourea and 2-chloromethyl-3-(4-acetyl-phenyl)-3H-quinazoline-4-one as otherwise described in Example 154. Yield: 44.30%, M.P. 218-20° C., LC-MS: 548.5(M+1), Rf: 0.49.

Example 272

2-(5-Morpholin-4-yl-4-phenyl-thiophene-2-yl)-3-phenyl-3H-quinazolin-4-one (Z)-1,3-Di-morpholin-4-yl-2-phenyl-propenthione was dissolved in acetonitrile and heated to 78° C. At this temperature 2-chloromethyl-3-phenyl-3H-quinazolin-4-one in acetonitrile was added, and the reaction mixture was held at 78° C. for 6-8 hrs. Then it was cooled to room temperature, and solvent was removed under vacuum. The solid residue was recrystallized to obtain 2-(5-morpholin-4-yl-4-phenyl-thiophene-2-yl)-3-phenyl-3H-quinazolin-4-one. Yield: 57.82%, M.P. 218-20° C., LC-MS: 466(M+1), Rf: 0.53.

Example 273

2-[4-(4-Chloro-phenyl)-5-morpholin-4-yl-thiophen-2-yl]-3-phenyl-3H-quinazolin-4-one The title compound was prepared from (Z)-2-(4-chloro-phenyl)-1,3-dimorpholin-4-yl-propenethione and 2-chloromethyl-3-phenyl-3H-quinazoline-4-one as otherwise described in Example 272. Yield: 51.41%, M.P. 229-30° C., LC-MS: 500(M+1), Rf: 0.53

Example 274

N-{4-[2-Morpholin-4-yl-5-(4-oxo-3-phenyl-3-,4-dihydroquinazolin-2-yl)-thiophene-3-yl]-phenyl}-acetamide The title compound was prepared from N-{4-[(Z)-1-(morpholin-4-carbothioyl)-2-morpholin-4-yl-vinyl]-phenyl}-acetamide and 2-chloromethyl-3-phenyl-3H-quinazoline-4-one as otherwise described in Example 272. Yield: 56.83%, M.P. >275° C., LC-MS: 523(M+1), Rf: 0.34

Example 275

2-[4-(4-Methanesulfonyl-phenyl)-5-morpholin-4-yl-thiophen-2-yl]-3-phenyl-3H-quinazolin-4-one The title compound was prepared from (Z)-2-(4-methanesulfonyl-phenyl)-1,3-di-morpholin-4-yl-propenethione and 2-chloromethyl-3-phenyl-3H-quinazoline-4-one as otherwise described in Example 272. Yield: 58.39%, M.P. >275° C., LC-MS: 544(M+1), Rf: 0.53

Example 276

2-[4-(4-Methylsulfanyl-phenyl)-5-morpholin-4-yl-thiophen-2-yl]-3-phenyl-3H-quinazolin-4-one The title compound was prepared from (Z)-2-(4-methylsulfanyl-phenyl)-1,3-di-morpholin-4-yl-propenethione and 2-chloromethyl-3-phenyl-3H-quinazoline-4-one as otherwise described in Example 272. Yield: 46.15%, M.P. 218-20° C., LC-MS: 480(M+1), Rf: 0.53

Example 277

2-(5-Morpholin-4-yl-4-pyridin-4-yl-thiophen-2-yl)-3-phenyl-3H-quinazolin-4-one (Z)-1,3-Di-morpholin-4-yl-2-pyridin-4-yl-propenethione was dissolved in dimethyl formamide. At room temperature, 2-chloromethyl-3-phenyl-3H-quinazoline-4-one in dimethyl formamide was added. The reaction mixture was stirred at room temperature for 24 hrs, after which it was poured into ice water, stirred well for 10 minutes, and filtered. The residue was dried and recrystallized from methanol to obtain pure 2-(5-morpholin-4-yl-4-pyridin-4-yl-thiophen-2-yl)-3-phenyl-3H-quinazolin-4-one. Yield: 37.67%, M.P. 230-1° C., LC-MS: 467(M+1), Rf: 0.34

Example 278

2-(5-Morpholin-4-yl-4-phenyl-thiophene-2-yl)-3-O-tolyl-3H-quinazolin-4-one

The title compound was prepared from (Z)-1,3-dimorpholin-4-yl-2-phenyl-propenthione and 2-chloromethyl-3-O-tolyl-3H-quinazoline-4-one as otherwise described in Example 277. Yield: 54.30%, M.P. 187-8° C., LC-MS: 480 (M+1), Rf: 0.60.

Example 279

2-[4-(4-Chloro-phenyl)-5-morpholin-4-yl-thiophen-2-yl]-3-o-tolyl-3H-quinazolin-4-one The title compound was prepared from (Z)-2-(4-chloro-phenyl)-1,3-dimorpholin-4-yl-propenethione and 2-chloromethyl-3-o-tolyl-3H-quinazoline-4-one as otherwise described in Example 277. Yield: 53.42%, M.P. 186-9° C., LC-MS: 514(M+1), Rf: 0.0.62

Example 280

N-{4-[2-Morpholin-4-yl-5-(4-oxo-3-O-tolyl-3-,4-dihydroquinazolin-2-yl)-thiophene-3-yl]-phenyl}-acetamide The title compound was prepared from N-{4-[(Z)-1-(morpholin-4-carbothioyl)-2-morpholin-4-yl-vinyl]-phenyl}-acetamide and 2-chloromethyl-3-O-tolyl-3H-quinazoline-4-one as otherwise described in Example 277. Yield: 51.74%, M.P. 242-3° C., LC-MS: 537(M+1), Rf: 0.30.

Example 281

2-[4-(4-Methanesulfonylphenyl)-5-morpholin-4-yl-thiophen-2-yl]-3-o-tolyl-3H-quinazolin-4-one The title compound was prepared from (Z)-2-(4-methanesulfonyl-phenyl)-1,3-dimorpholin-4-yl-propenethione and 2-chloromethyl-3-o-tolyl-3H-quinazoline-4-one as otherwise described in Example 277. Yield: 55.71%, M.P. 255-8° C., LC-MS: 557(M+1), Rf: 0.42

Example 282

2-[4-(4-Methylsulfanylphenyl)-5-morpholin-4-yl-thiophen-2-yl]-3-O-tolyl-3H-quinazolin-4-one The title compound was prepared from (Z)-2-(4-methylsulfanyl-phenyl)-1,3-dimorpholin-4-yl-propenethione and 2-chloromethyl-3-O-tolyl-3H-quinazoline-4-one as otherwise described in Example 277. Yield: 43.75%, M.P. >275° C., LC-MS: 525(M+1), Rf: 0.59

Example 283

2-(5-Morpholin-4-yl-4-pyridin-4-yl-thiophen-2-yl)-3-o-tolyl-3H-quinazolin-4-one

The title compound was prepared from (Z)-1,3-mimorpholin-4-yl-2-pyridin-4-yl-propenethione and 2-chloromethyl-3-O-tolyl-3H-quinazoline-4-one as otherwise described in Example 285. Yield: 38.66%, M.P. 208-1° C., LC-MS: 481 (M+1), Rf: 0.38.

Example 284

2-(5-Morpholin-4-yl-4-phenyl-thiophene-2-yl)-3-m-tolyl-3H-quinazolin-4-one

The title compound was prepared from (Z)-1,3-dimorpholin-4-yl-2-phenyl-propenthione and 2-chloromethyl-3-m-tolyl-3H-quinazoline-4-one as otherwise described in Example 277. Yield: 53.64%, M.P. 194-6° C., LC-MS: 480 (M+1), Rf: 0.50.

Example 285

2-[4-(4-Chloro-phenyl)-5-morpholin-4-yl-thiophen-2-yl]-3-m-tolyl-3H-quinazolin-4-one The title compound was prepared from (Z)-2-(4-chlorophenyl)-1,3-dimorpholin-4-yl-propenethione and 2-chloromethyl-3-m-tolyl-3H-quinazoline-4-one as otherwise described in Example 277. Yield: 49.32%, M.P. 228-30° C., LC-MS: 514(M+1), Rf: 0.57.

Example 286

N-{4-[2-Morpholin-4-yl-5-(4-oxo-3-m-tolyl-3-,4-dihydroquinazolin-2-yl)-thiophene-3-yl]-phenyl}-acetamide The title compound was prepared from N-{4-[(Z)-1-(morpholin-4-carbothioyl)-2-morpholin-4-yl-vinyl]-phenyl}-acetamide and 2-chloromethyl-3-m-tolyl-3H-quinazoline-4-one as otherwise described in Example 277. Yield: 52.44%, M.P. >275° C., LC-MS: 537(M+1), Rf: 0.61

Example 287

2-[4-(4-Methanesulfonyl-phenyl)-5-morpholin-4-yl-thiophen-2-yl]-3-m-tolyl-3H-quinazolin-4-one The title compound was prepared from (Z)-2-(4-methanesulfonyl-phenyl)-1,3-dimorpholin-4-yl-propenethione and 2-chloromethyl-3-m-tolyl-3H-quinazoline-4-one as otherwise described in Example 277. Yield: 54.54%, M.P. 208-10° C., LC-MS: 558(M+1), Rf: 0.62

Example 288

2-[4-(4-Methylsulfanyl-phenyl)-5-morpholin-4-yl-thiophen-2-yl]-3-m-tolyl-3H-quinazolin-4-one The title compound was prepared from (Z)-2-(4-methylsulfanyl-phenyl)-1,3-dimorpholin-4-yl-propenethione and 2-chloromethyl-3-m-tolyl-3H-quinazoline-4-one as otherwise described in Example 277. Yield: 43.05%, M.P. 220-1° C., LC-MS: 525(M+1), Rf: 0.59

Example 289

2-(5-Morpholin-4-yl-4-pyridin-4-yl-thiophen-2-yl)-3-m-tolyl-3H-quinazolin-4-one

The title compound was prepared from (Z)-1,3-dimorpholin-4-yl-2-pyridin-4-yl-propenethione and 2-chloromethyl-3-m-tolyl-3H-quinazoline-4-one as otherwise described in Example 277. Yield: 36%%, M.P. 230-2° C., LC-MS: 481 (M+1), Rf: 0.57.

Example 290

2-(5-Morpholin-4-yl-4-phenyl-thiophene-2-yl)-3-p-tolyl-3H-quinazolin-4-one

The title compound was prepared from (Z)-1,3-di-morpholin-4-yl-2-phenyl-propenthione and 2-chloromethyl-3-p-tolyl-3H-quinazoline-4-one as otherwise described in Example 277. Yield: 54.30%, M.P. 207-9° C., LC-MS: 480 (M+1), Rf: 0.63.

Example 291

2-[4-(4-Chlorophenyl)-5-morpholin-4-yl-thiophen-2-yl]-3-p-tolyl-3H-quinazolin-4-one The title compound was prepared from (Z)-2-(4-chlorophenyl)-1,3-dimorpholin-4-yl-propenethione and 2-chloromethyl-3-p-tolyl-3H-quinazoline-4-one as otherwise described in Example 277. Yield: 51.36%, M.P. 224-6° C., LC-MS: 514(M+1), Rf: 0.63.

Example 292

2-[4-(4-Methanesulfonyl-phenyl)-5-morpholin-4-yl-thiophen-2-yl]-3-p-tolyl-3H-quinazolin-4-one The title compound was prepared from (Z)-2-(4-methanesulfonyl-phenyl)-1,3-dimorpholin-4-yl-propenethione and 2-chloromethyl-3-p-tolyl-3H-quinazoline-4-one as otherwise described in Example 277. Yield: 57.86%, M.P. 265-8° C., LC-MS: 558(M+1), Rf: 0.57.

Example 293

2-[4-(4-Methylsulfanyl-phenyl)-5-morpholin-4-yl-thiophen-2-yl]-3-p-tolyl-3H-quinazolin-4-one The title compound was prepared from (Z)-2-(4-methylsulfanyl-phenyl)-1,3-dimorpholin-4-yl-propenethione and 2-Chloromethyl-3-p-tolyl-3H-quinazoline-4-one as otherwise described in Example 277. M.P. 238-40° C., Rf: 0.59.

Example 294

3-(2-Methoxy-phenyl)-2-(5-morpholin-4-yl-4-phenyl-thiophen-2-yl)-3H-quinazolin-4-one The title compound was prepared from (Z)-1,3-dimorpholin-4-yl-2-phenyl-propenthione and 2-chloromethyl-3-(2- methoxy-phenyl)-3H-quinazoline-4-one as otherwise described in Example 277. Yield: 52.20%, M.P. 152-4° C., LC-MS: 496(M+1), Rf: 0.56.

Example 295

2-[4-(4-Chlorophenyl)-5-morpholin-4-yl-thiophene-2-yl]-3-(2-methoxy-phenyl)-3H-quinazolin-4-one The title compound was prepared from (Z)-2-(4-chlorophenyl)-1,3-dimorpholin-4-yl-propenethione and 2-chloromethyl-3-(2-methoxy-phenyl)-3H-quinazoline-4-one as otherwise described in Example 277. Yield: 47.68%, M.P. 216-7° C., LC-MS: 530(M+1), Rf: 0.65.

Example 296

N-(4-{5-[3-(2-methoxy-phenyl)-4-oxo-3,4-dihydroquinazolin-2-yl]-2-morpholin-4-yl-thiophene-3-yl}-acetamide The title compound was prepared from N-{4-[(Z)-1-(morpholin-4-carbothioyl)-2-morpholin-4-yl-vinyl]-phenyl}-acetamide and 2-chloromethyl-3-(2-methoxy-phenyl)-3H-quinazoline-4-one as otherwise described in Example 277. Yield: 53.74%, M.P. 163-4° C., LC-MS: 553(M+1), Rf: 0.64

Example 297

2-[4-(4-Methanesulphonyl-phenyl)-5-morpholin-4-yl-thiophen-2-yl]-3-(2-methoxy-phenyl)-3H-quinazolin-4-one The title compound was prepared from (Z)-2-(4-methanesulfonyl-phenyl)-1,3-di-morpholin-4-yl-propenethione and 2-chloromethyl-3-(2-methoxy-phenyl)-3H-quinazoline-4-one as otherwise described in Example 277. Yield: 55.17%, M.P. 222-3° C., LC-MS: 574(M+1), Rf: 0.62

Example 298

3-(2-Methoxy-phenyl)-2-(5-morpholin-4-yl-4-pyridin-4-yl-thiophen-2-yl)-3H-quinazolin-4-one The title compound was prepared from (Z)-1,3-dimorpholin-4-yl-2-pyridin-4-yl-propenethione and 2-chloromethyl-3-(2-methoxy-phenyl)-3H-quinazoline-4-one as otherwise described in Example 277. Yield: 41.29%, M.P. 204-5° C., LC-MS: 497(M+1), Rf: 0.58.

Example 299

3-(3-Methoxy-phenyl)-2-(5-morpholin-4-yl-4-phenyl-thiophen-2-yl)-3H-quinazolin-4-one The title compound was prepared from (Z)-1,3-dimorpholin-4-yl-2-phenyl-propenthione and 2-chloromethyl-3-(3-methoxy-phenyl)-3H-quinazoline-4-one as otherwise described in Example 277. Yield: 50.95%, MP: 269-72° C., LC-MS: 496(M+1), Rf: 0.63.

Example 300

2-[4-(4-Methanesulphonyl-phenyl)-5-morpholin-4-yl-thiophen-2-yl]-3-(3-methoxy-phenyl)-3H-quinazolin-4-one The title compound was prepared from (Z)-2-(4-methanesulfonyl-phenyl)-1,3-di-morpholin-4-yl-propenethione and 2-chloromethyl-3-(3-methoxy-phenyl)-3H-quinazoline-4-one as otherwise described in Example 277. Yield: 56.55%, M.P. 203-5° C., LC-MS: 574(M+1), Rf: 0.58.

Example 301

3-(4-Methoxy-phenyl)-2-(5-morpholin-4-yl-4-phenyl-thiophen-2-yl)-3H-quinazolin-4-one The title compound was prepared from (Z)-1,3-dimorpholin-4-yl-2-phenyl-propenthione and 2-chloromethyl-3-(4-methoxy-phenyl)-3H-quinazoline-4-one as otherwise described in Example 277. Yield: 52.23%, M.P. 164-5° C., LC-MS: 496(M+1), Rf: 0.67.

Example 302

2-[4-(4-Chloro-phenyl)-5-morpholin-4-yl-thiophene-2-yl]-3-(4-methoxy-phenyl)-3H-quinazolin-4-one The title compound was prepared from (Z)-2-(4-chlorophenyl)-1,3-dimorpholin-4-yl-propenethione and 2-chloromethyl-3-(4-methoxy-phenyl)-3H-quinazoline-4-one as otherwise described in Example 277. Yield: 49%, M.P. 217-8° C., LC-MS: 530(M+1), Rf: 0.69.

Example 303

2-[4-(4-Methanesulphonyl-phenyl)-5-morpholin-4-yl-thiophen-2-yl]-3-(4-methoxy-phenyl)-3H-quinazolin-4-one The title compound was prepared from (Z)-2-(4-methanesulfonyl-phenyl)-1,3-dimorpholin-4-yl-propenethione and 2-chloromethyl-3-(4-methoxy-phenyl)-3H-quinazoline-4-one as otherwise described in Example 277. Yield: 55.86%, M.P. 240-3° C., LC-MS: 574(M+1), Rf: 0.49.

Example 304

3-(2-Chlorophenyl)-2-(5-morpholin-4-yl-4-phenyl-thiophen-2-yl)-3H-quinazolin-4-one The title compound was prepared from (Z)-1,3-dimorpholin-4-yl-2-phenyl-propenthione and 2-chloromethyl-3-(2-chloro-phenyl)-3H-quinazoline-4-one as otherwise described in Example 277. Yield: 50.63%, M.P. 160-1° C., LC-MS: 500(M+1), Rf: 0.65.

Example 305

2-[4-(4-Chlorophenyl)-5-morpholin-4-yl-thiophene-2-yl]-3-(2-chlorophenyl)-3H-quinazolin-4-one The title compound was prepared from (Z)-2-(4-chlorophenyl)-1,3-dimorpholin-4-yl-propenethione and 2-chloromethyl-3-(2-chloro-phenyl)-3H-quinazoline-4-one as otherwise described in Example 277. Yield: 51.97%, M.P. 215-7° C., LC-MS: 534(M+1), Rf: 0.68.

Example 306

3-(2-Methoxy-phenyl)-2-(5-morpholin-4-yl-4-pyridin-4-yl-thiophen-2-yl)-3H-quinazolin-4-one The title compound was prepared from N-{4-[(Z)-1-(morpholin-4-carbothioyl)-2-morpholin-4-yl-vinyl]-phenyl}-acetamide and 2-chloromethyl-3-(2-chloro-phenyl)-3H-quinazoline-4-one as otherwise described in Example 277. Yield: 48.65%, M.P. 210-2° C., LC-MS: 557(M+1), Rf: 0.59.

Example 307

2-[4-(4-Methanesulphonyl-phenyl)-5-morpholin-4-yl-thiophen-2-yl]-3-(2-chloro-phenyl)-3H-quinazolin-4-one The title compound was prepared from (Z)-2-(4-methanesulfonyl-phenyl)-1,3-dimorpholin-4-yl-propenethione and 2-chloromethyl-3-(2-chloro-phenyl)-3H-quinazoline-4-one as otherwise described in Example 277. Yield: 58.62%, M.P. >275° C., LC-MS: 577, Rf: 0.56.

Example 308

3-(2-Chloro-phenyl)-2-(5-morpholin-4-yl-4-pyridin-4-yl-thiophen-2-yl)-3H-quinazolin-4-one The title compound was prepared from (Z)-1,3-dimorpholin-4-yl-2-pyridin-4-yl-propenethione and 2-chloromethyl-3-(2-chloro-phenyl)-3H-quinazoline-4-one as otherwise described in Example 277. Yield: 39.49%, M.P. 179-80° C., LC-MS: 501(M+1), Rf: 0.58.

Example 309

3-(4-Chloro-phenyl)-2-(5-morpholin-4-yl-4-phenyl-thiophen-2-yl)-3H-quinazolin-4-one The title compound was prepared from (Z)-1,3-dimorpholin-4-yl-2-phenyl-propenthione and 2-chloromethyl-3-(4-chloro-phenyl)-3H-quinazoline-4-one as otherwise described in Example 277. Yield: 54.43%, M.P. 223-4° C., LC-MS: 500(M+1), Rf: 0.68.

Example 310

2-[4-(4-Chloro-phenyl)-5-morpholin-4-yl-thiophene-2-yl]-3-(4-chloro-phenyl)-3H-quinazolin-4-one The title compound was prepared from (Z)-2-(4-chloro-phenyl)-1,3-dimorpholin-4-yl-propenethione and 2-chloromethyl-3-(4-chloro-phenyl)-3H-quinazoline-4-one as otherwise described in Example 277. Yield: 55.26%, MP: 240-3° C., LC-MS: 534(M+1), Rf: 0.68

Example 311

N-(4-{5-[3-(4-Chloro-phenyl)-4-oxo-3,4-dihydro-quinazolin-2-yl]-2-morpholin-4-yl-thiophene-3-yl}-acetamide The title compound was prepared from N-{4-[(Z)-1-(morpholin-4-carbothioyl)-2-morpholin-4-yl-vinyl]-phenyl}-acetamide and 2-chloromethyl-3-(4-chloro-phenyl)-3H-quinazoline-4-one as otherwise described in Example 277. Yield: 54.05%, M.P. >275° C., LC-MS: 557(M+1), Rf: 0.29.

Example 312

2-[4-(4-Methanesulphonyl-phenyl)-5-morpholin-4-yl-thiophen-2-yl]-3-(4-chloro-phenyl)-3H-quinazolin-4-one The title compound was prepared from (Z)-2-(4-methanesulfonyl-phenyl)-1,3-di-morpholin-4-yl-propenethione and 2-chloromethyl-3-(4-chloro-phenyl)-3H-quinazoline-4-one as otherwise described in Example 277. Yield: 56.55%, M.P. >275° C., LC-MS: 577(M+1), Rf: 0.54

Example 313

3-(4-Chloro-phenyl)-2-(5-morpholin-4-yl-4-pyridin-4-yl-thiophen-2-yl)-3H-quinazolin-4-one The title compound was prepared from (Z)-1,3-dimorpholin-4-yl-2-pyridin-4-yl-propenethione and 2-chloro-methyl-3-(4-chloro-phenyl)-3H-quinazoline-4-one as otherwise described in Example 285. Yield: 39.74%, MP: 195-7° C., LC-MS: 501(M+1), Rf: 0.57.

Example 314

3-(4-Acetyl-phenyl)-2-(5-morpholin-4-yl-4-phenyl-thiophen-2-yl)-3H-quinazolin-4-one The title compound was prepared from (Z)-1,3-dimorpholin-4-yl-2-phenyl-propenthione and 2-chloromethyl-3-(4-acetyl-phenyl)-3H-quinazoline-4-one as otherwise described in Example 277. Yield 51.88%, M.P. >275° C., LC-MS: 508 (M+1), Rf: 0.47.

Example 315

2-[4-(4-Acetyl-phenyl)-5-morpholin-4-yl-thiophene-2-yl]-3-(4-chloro-phenyl)-3H-quinazolin-4-one The title compound was prepared from (Z)-2-(4-chloro-phenyl)-1,3-di-morpholin-4-yl-propenethione and 2-chloromethyl-3-(4-acetyl-phenyl)-3H-quinazoline-4-one as otherwise described in Example 277. Yield: 50.32%, M.P. 222-6° C., LC-MS: 542(M+1), Rf: 0.45.

Example 316

N-(4-{5-[3-(4-Acetyl-phenyl)-4-oxo-3,4-dihydro-quinazolin-2-yl]-2-morpholin-4-yl-thiophene-3-yl}-acetamide The title compound was prepared from N-{4-[(Z)-1-(morpholin-4-carbothioyl)-2-morpholin-4-yl-vinyl]-phenyl}-acetamide and 2-chloromethyl-3-(4-acetyl-phenyl)-3H-quinazoline-4-one as otherwise described in Example 277. Yield: 55.33%, M.P. 259-61° C., LC-MS: 565(M+1), Rf: 0.49.

Example 317

2-[4-(4-Methanesulphonyl-phenyl)-5-morpholin-4-yl-thiophen-2-yl]-3-(4-acetyl-phenyl)-3H-quinazolin-4-one The title compound was prepared from (Z)-2-(4-methanesulfonyl-phenyl)-1,3-di-morpholin-4-yl-propenethione and 2-chloromethyl-3-(4-acetyl-phenyl)-3H-quinazoline-4-one as otherwise described in Example 277. Yield: 54.05%, M.P. 239-42° C., LC-MS: 586(M+1), Rf: 0.51.

Example 318

3-(4-Chlorophenyl)-2-[4-(4-methanesulfonyl-phenyl)-5-(4-methyl-piperazine-1-yl)-thiophen-2-yl]-3H-quinazolin-4-one The title compound was prepared from (Z)-2-(4-chloro-phenyl)-1,3-bis-(4-methyl-piperazin-1-yl)-propenethione and 2-chloromethyl-3-(4-chloro-phenyl)-3H-quinazoline-4-one as otherwise described in Example 277. Yield: 52.6%, M.P. 232-3° C., LC-MS: 590(M+1) Rf: 0.63

Example 319

3-(4-acetyl-phenyl)-2-(5-morpholin-4-yl-4-pyridin-4-yl-thiophen-2-yl)-3H-quinazolin-4-one The title compound was prepared from (Z)-1,3-di-morpholin-4-yl-2-pyridin-4-yl-propenethione and 2-chloromethyl-3-(4-acetyl-phenyl)-3H-quinazoline-4-one as otherwise describe in example 277. Yield: 42.0%, M.P.: 241-2° C., Rf: 0.53, LC-MS (m/e): 509 (M+1), $^1$H-NMR NMR(300 MHz, CDCl$_3$) δ[ppm]: 2.69 (s, 3H, —COCH3),2.92-2.95 (m, 4H, proton at C3 and C5 position of morpholine), 2.71-2.75 (m, 4H), 6.12 (s, 1H), 7.19-8.16 (m, 9H), 8.28-8.48 (m, 1H), 8.43-8.45 (m, 2H), Elemental analysis: Calculated: C, 68.49; H, 4.76; N, 11.02 Obtained: C, 68.44; H, 4.64; N, 11.54.

Example 320

2-(2-Methylamino-4-phenyl-thiazole-5-yl)-3-phenyl-3H-quinazolin-4-one

The title compound was prepared from 1-[1-diethylamino-1-phenyl-meth-(E)-ylidene]-3-methyl-thiourea and 2-chloromethyl-3-(phenyl)-3H-quinazoline-4-one as otherwise described in Example 154. Yield: 23.8%, M.P. 224-5° C., LC-MS: 411(M+1), Rf: 0.52.

Example 321

4-Amino-(2-phenylamino-thiazol-5-yl)-(4-methoxy-phenyl)-methanone

To a solution of 1-amidino-3-phenylthiourea (0.0077 mole) in 10 ml ethanol was added p-methoxyphenacyl bromide (0.0077 mole) and tri-ethylamine (0.0077 mole). The solution was refluxed for 3 hours, the reaction mixture was cooled to room temperature, and the reaction mixture was concentrated under vacuum. Crushed ice was added to the residue, and the separated solid was filtered and washed with water to give yellow crystals (41% yield). M.P. 222° C. Recrystallization Solvent: methanol. TLC: Mobile Phase: Ethyl acetate, Rf: 0.68. IR (KBr, cm-1) showed 3489 (NH), 3319, 3265 (NH2), 3084, 1885, 1622, 1562, 1499. Mass, (LC-MS, M+1): 326. 1H-NMR (CDCl3, δ, ppm): 3.8 (m, 3H, OCH3), 6.9 (d, 2H, phenyl), 7.2-7.4 (m, 2H of NH2 and 5H of phenyl), 7.43 (s, 1H, of NH), 7.74-7.76 (d, 2H, phenyl), and Molecular formula as C17H15N3O2S.

Example 322

4-Amino-(2-phenylamino-thiazol-5-yl)-p-tolyl-methanone

The title compound was prepared from 1-amidino-3-phenylthiourea (0.0077 mole) in 10 ml ethanol, p-methylphenacyl bromide (0.0077 mole) and tri-ethylamine (0.0077 mole) as per described in the example 39 to provide desired compound. Yield 50.72%. M.P. 211-212° C., LC MS: 310 (M+1). C17H15N3OS. TLC: Mobile Phase: Ethyl acetate, Rf: 0.78. IR (KBr, cm-1): 3480, 3250, 3200, 1610, 1590, 1520

Example 323

(4-Amino-2-phenylamino-thiazol-5-yl)-(4-chloro-phenyl)-methanone

The title compound was prepared from 1-amidino-3-phenylthiourea (0.0077 mole) in 10 ml ethanol, 4-chlorophenacyl bromide (0.0077 mole) and tri-ethylamine (0.0077 mole) as per described in the example 39 to provide desired compound. Yield 67.72%. M.P. 221-222° C., LC MS: 331 (M+2). C16H12ClN3OS. TLC: Mobile Phase: Ethyl acetate, Rf: 0.57. IR (KBr, cm-1): 3460, 3250, 3080, 1720, 1580, 1515

Example 324

(4-Amino-2-phenylamino-thiazol-5-yl)-(2,4-dichloro-phenyl)-methanone

The title compound was prepared from 1-amidino-3-phenylthiourea (0.0077 mole) in 10 ml ethanol, 2,4-dichlorophenacyl bromide (0.0077 mole) and tri-ethylamine (0.0077 mole) as per described in the example 39 to provide desired compound. Yield 47.34%. M.P. 234-235° C., LC MS: 366 (M+2). C16H11Cl2N3OS. TLC: Mobile Phase: Ethyl acetate, Rf: 0.48. IR (KBr, cm-1): 3456, 3290, 3050, 1690, 1570, 1520

Example 325

(4-Amino-2-phenylamino-thiazol-5-yl)-(4-methanesulfonyl-phenyl)-methanone

The title compound was prepared from 1-amidino-3-phenylthiourea (0.0077 mole) in 10 ml p-methylsulfonyl phenacylbromide (0.0077 mole) and tri-ethylamine (0.0077 mole) as per described in the example 39 to provide desired compound. Yield 39.4%. M.P. 257-258° C., LC MS: 374 (M+1). C17H15N3O3S2. TLC: Mobile Phase: Ethyl acetate, Rf: 0.37.

Example 326

N-[4-(4-Amino-2-phenylamino-thiazole-5-carbonyl)-phenyl]-acetamide

The title compound was prepared from 1-amidino-3-phenylthiourea (0.0077 mole) in 10 ml ethanol, N-[4-(2-Bromoacetyl)-phenyl]-acetamide (0.0077 mole) and tri-ethylamine (0.0077 mole) as per described in the example 39 to provide desired compound. Yield 39.4%. M.P. 257-258° C., LC MS: 353 (M+1). C18H16N4O2S. TLC: Mobile Phase: Ethyl acetate, Rf: 0.37.

Example 327

(4-Amino-2-phenylamino-thiazol-5-yl)-pyridin-3-yl-methanone

The title compound was prepared from 1-amidino-3-phenylthiourea (0.0077 mole) in 10 ml ethanol, 2-Boromo-1-pyridin-3yl-ethanone (0.0077 mole) and tri-ethylamine (0.0077 mole) as per described in the example 39 to provide desired compound. Yield 62.27%. M.P. 263-264° C., LC MS: 297 (M+1). C15H12N4OS. TLC: Mobile Phase: Ethyl acetate, Rf: 0.42.

Example 328

(4-Amino-2-phenylamino-thiazol-5-yl)-pyridin-4-yl-methanone

The title compound was prepared from 1-amidino-3-phenylthiourea (0.0077 mole) in 10 ml ethanol, 2-Boromo-1-pyridin-4yl-ethanone (0.0077 mole) and tri-ethylamine (0.0077 mole) as per described in the example to provide desired compound. Yield 77.32%. M.P. 257-258° C., LC MS: 297 (M+1). C15H12N4OS. TLC: Mobile Phase: Ethyl acetate, Rf: 0.44.

Example 329

(4-Amino-2-phenylamino-thiazol-5-yl)-pyridin-2-yl-methanone

The title compound was prepared from 1-amidino-3-phenylthiourea (0.0077 mole) in 10 ml ethanol, 2-Boromo-1-pyridin-2yl-ethanone (0.0077 mole) and tri-ethylamine (0.0077 mole) as per described in the example 39 to provide desired compound. Yield 24.22. 2%. M.P. 214-215° C., LC MS: 297 (M+1). C15H12N4OS. TLC: Mobile Phase: Ethyl acetate, Rf: 0.37.

Example 330

5-(4-Methoxy-3,5-dimethyl-pyridin-2-yl)-N2-phenyl-thiazole-2,4-diamine

The title compound was prepared from 1-amidino-3-phenylthiourea (0.0077 mole) in 10 ml ethanol, 2-Cholromethyl-4-methoxy-3,5-dimeth-yl-pyridine (0.0077 mole) and triethylamine (0.0077 mole) as per described in the example 39 to provide desired compound. Yield 26.32%. M.P. 251-253° C., LC MS: 327 (M+1). C17H18N4OS. TLC: Mobile Phase: Ethyl acetate, Rf: 0.52.

Example 331

5-[3-Methyl-4-(2,2,2-trifluoro-ethoxy)-pyridin-2-yl]-N2-phenyl-thiazole-2,4-diamine The title compound was prepared from 1-amidino-3-phenylthiourea (0.0077 mole) in 10 ml ethanol, 2-Chloromethyl-4-methyl-3-(2,2,2-trifluoro-ethoxy)-pyridine (0.0077 mole) and tri-ethylamine (0.0077 mole) as per described in the example 39 to provide desired compound. Yield 42.00%. M.P. 199-201° C., LC MS: 381 (M+1). C17H15F3N4OS. TLC: Mobile Phase Ethyl acetate, Rf: 0.53.

Example 332

[4-Amino-2-(4-chloro-phenylamino)-thiazol-5-yl]-(4-methoxy-phenyl)-methanone

The title compound was prepared from 1-amidino-3-p-chlorophenylthiourea (0.0057 mole) in 10 ml ethanol, p-methoxyphenacyl bromide (0.0057 mole) and tri-ethylamine (0.0057 mole) as per described in the example 39 to provide desired compound. Yield 51.79%. M.P. >280° C., LC MS: 361 (M+2). C17H14ClN3O2S. TLC: Mobile Phase: Ethyl acetate, Rf: 0.67.

Example 333

[4-Amino-2-(4-chloro-phenylamino)-thiazol-5-yl]-p-tolyl-methanone

The title compound was prepared from 1-amidino-3-p-chlorophenylthiourea (0.0057 mole) in 10 ml ethanol, p-methylphenacyl bromide (0.0057 mole) and tri-ethylamine (0.0057 mole) as per described in the example 39 to provide desired compound. Yield 40.47%. M.P. 195-196° C., LC MS: 345 (M+2). C17H14ClN3OS. TLC: Mobile Phase: Ethyl acetate, Rf: 0.54.

Example 334

[4-Amino-2-(4-chloro-phenylamino)-thiazol-5-yl]-(4-chloro-phenyl)-methanone

The title compound was prepared from 1-amidino-3-p-chlorophenylthiourea (0.0057 mole) in 10 ml ethanol, 4-chlorophenacyl bromide (0.0057 mole) and tri-ethylamine (0.0057 mole) as per described in the example 39 to provide desired compound. Yield 67.72%. M.P. 224-225° C., LC MS: 366 (M+2). C16H10Cl2N3OS. TLC: Mobile Phase: Ethyl acetate, Rf: 0.53.

Example 335

[4-Amino-2-(4-chloro-phenylamino)-thiazol-5-yl]-(2,4-dichloro-phenyl)-methanone

The title compound was prepared from 1-amidino-3-p-chlorophenylthiourea (0.0057 mole) in 10 ml ethanol, 2,4-dichlorophenacyl bromide (0.0057 mole) and tri-ethylamine (0.0057 mole) as per described in the example 39 to provide desired compound. Yield 27.34%. M.P. 254-235° C., LC MS: 398 (M+2). C16H10Cl3N3OS. TLC: Mobile Phase: Ethyl acetate, Rf: 0.78.

Example 336

[4-Amino-2-(4-chloro-phenylamino)-thiazol-5-yl]-(4-methanesulfonyl-phenyl)-methanone The title compound was prepared from 1-amidino-3-p-chlorophenylthiourea (0.0057 mole) in 10 ml ethanol, p-methylsulfonyl phenacyl bromide (0.0057 mole) and tri-ethylamine (0.0057 mole) as per described in the example 39 to provide desired compound. Yield 64.42%. M.P. >285° C., LC MS: 409 (M+2). C17H14ClN3O3S2. TLC: Mobile Phase: Ethyl acetate, Rf: 0.53.

Example 337

N-{4-[4-Amino-2-(4-chloro-phenylamino)-thiazole-5-carbonyl]-phenyl}-acetamide

The title compound was prepared from 1-amidino-3-p-chlorophenylthiourea (0.0057 mole) in 10 ml ethanol, N-[4-(2-Bromo-acetyl)-phenyl]-acetamide (0.0057 mole) and tri-ethylamine (0.0057 mole) as per described in the example 39 to provide desired compound. Yield 39.4%. M.P. >285° C., LC MS: 388 (M+2). C18H15ClN4O2S. TLC: Mobile Phase: Ethyl acetate, Rf: 0.42.

Example 338

(4-Amino-2-(4-chlorophenylamino)-thiazol-5-yl)-pyridin-3-yl-methanone

The title compound was prepared from 1-amidino-3-p-chlorophenylthiourea (0.0057 mole) in 10 ml ethanol, 2-Boromo-1-pyridin-3yl-ethanone (0.0057 mole) and tri-ethylamine (0.0057 mole) as per described in the example 39 to provide desired compound. Yield 62.27%. M.P. 223-224° C., LC MS: 332 (M+2). C15H12N4OS. TLC: Mobile Phase: Ethyl acetate, Rf: 0.42.

Example 339

[4-Amino-2-(4-chloro-phenylamino)-thiazol-5-yl]-pyridin-4-yl-methanone

The title compound was prepared from 1-amidino-3-p-chlorophenylthiourea (0.0057 mole) in 10 ml ethanol, 2-Boromo-1-pyridin-4yl-ethanone (0.0057 mole) and tri-ethylamine (0.0057 mole) as per described in the example 39 to provide desired compound. Yield 77.32%. M.P. 227-228° C., LC MS: 332 (M+2). C15H12N4OS. TLC: Mobile Phase: Ethyl acetate, Rf: 0.24.

Example 340

[4-Amino-2-(4-chloro-phenylamino)-thiazol-5-yl]-pyridin-2-yl-methanone

The title compound was prepared from 1-amidino-3-p-chlorophenylthiourea (0.0057 mole) in 10 ml ethanol, 2-Boromo-1-pyridin-2yl-ethanone (0.0057 mole) and tri-ethylamine (0.0057 mole) as per described in the example 39 to provide desired compound. Yield 24.22. 2%. M.P. 224-225° C., LC MS: 332 (M+2). C15H12N4OS. TLC: Mobile Phase: Ethyl acetate, Rf: 0.42.

Example 341

N2-(4-Chloro-phenyl)-5-(4-Methoxy-3,5-dimethyl-pyridin-2-yl)-thiazole-2,4-diamine)

The title compound was prepared from 1-amidino-3-p-chlorophenylthiourea (0.0057 mole) in 10 ml ethanol, 2-Cholromethyl-4-methoxy-3,5-dimeth-yl-pyridine (0.0057 mole) and tri-ethylamine (0.0057 mole) as per described in the example 39 to provide desired compound. Yield 26.32%. M.P. 255-256° C., LC MS: 362 (M+2). C17H18N4OS. TLC: Mobile Phase: Ethyl acetate, Rf: 0.47.

Example 342

(N2-(4-Chloro-phenyl)-5-[3-Methyl-4-(2,2,2-trifluoro-ethoxy)-pyridin-2-yl]-thiazole-2,4-diamine)

The title compound was prepared from 1-amidino-3-p-chlorophenylthiourea (0.0057 mole) in 10 ml ethanol, 2-Chloromethyl-3-methyl-4-(2,2,2-trifluoro-ethoxy)-pyridine (0.0057 mole) and tri-ethylamine (0.0057 mole) as per described in the example 39 to provide desired compound. Yield 42.00%. M.P. 199-201° C., LC MS: 416 (M+2). C17H14F3N4OS. TLC: Mobile Phase: Ethyl acetate, Rf: 0.43. IR (KBr, cm-1): 3390, 3260, 3050, 1615, 1550, 1490. 1H NMR (CDCl3, δ, ppm): 2.21 (m, 3H, CH3), 4.8 (m, 2H, OCH2CF3), 6.8-7.7 (m, 4H, phenyl), 8.2-8.3 (m, 2H of NH2 and 2H of pyridine), 10.4 (s, 1H, of NH).

Example 343

([4-Amino-2-(4-methoxy-phenylamino)-thiazol-5-yl]-(4-methoxy-phenyl)-methanone)

The title compound was prepared from 1-amidino-3-p-methoxyphenylthiourea (0.0057 mole) in 10 ml ethanol, p-methoxyphenacyl bromide (0.0057 mole) and tri-ethylamine (0.0057 mole) as described in the example 39 to provide desired compound. Yield 51.79%. M.P. >280° C., LC MS: 356 (M+1). C18H17N3O3S. TLC: Mobile Phase: Ethyl acetate, Rf: 0.76.

Example 344

([4-Amino-2-(4-methoxy-phenylamino)-thiazol-5-yl]-p-tolyl-methanone)

The title compound was prepared from 1-amidino-3-p-methoxyphenylthiourea (0.0077 mole) in 10 ml ethanol, p-methylphenacyl bromide (0.0077 mole) and tri-ethylamine (0.0077 mole) as described in the example 39 to provide desired compound. Yield 50.72%. M.P. >280° C., LC MS: 340 (M+1). C18H17N3O2S. TLC: Mobile Phase: Ethyl acetate, Rf: 0.67.

Example 345

([4-Amino-2-(4-methoxy-phenylamino)-thiazol-5-yl]-(4-chloro-phenyl)-methanone)

The title compound was prepared from 1-amidino-3-p-methoxyphenylthiourea (0.0077 mole) in 10 ml ethanol, 4-chlorophenacyl bromide (0.0077 mole) and tri-ethylamine (0.0077 mole) as per described in the example 39 to provide desired compound. Yield 67.72%. M.P. >280° C., LC MS: 361 (M+2). C17H14ClN3O2S. TLC: Mobile Phase: Ethyl acetate, Rf: 0.53.

Example 346

([4-Amino-2-(4-methoxy-phenylamino)-thiazol-5-yl]-(2,4-dichloro-phenyl)-methanone)

The title compound was prepared from 1-amidino-3-p-methoxyphenylthiourea (0.0077 mole) in 10 ml ethanol, 2,4-dichlorophenacyl bromide (0.0077 mole) and tri-ethylamine (0.0077 mole) as per described in the example 39 to provide desired compound. Yield 47.34%. M.P. >280° C., LC MS: 396 (M+2). C17H13Cl2N3O2S. TLC: Mobile Phase: Ethyl acetate, Rf: 0.43.

Example 347

([4-Amino-2-(4-methoxy-phenylamino)-thiazol-5-yl]-(4-methanesulfonyl-phenyl)-methanone)

The title compound was prepared from 1-amidino-3-p-methoxyphenylthiourea (0.0077 mole) in 10 ml ethanol, p-sulfonylphenacyl bromide (0.0077 mole) and tri-ethylamine (0.0077 mole) as per described in the example 39 to provide desired compound. Yield 37.2%. M.P. >280° C., LC MS: 404 (M+1). C18H17N3O4S2. TLC: Mobile Phase: Ethyl acetate, Rf: 0.47.

Example 348

(N-{4-[4-Amino-2-(4-methoxy-phenylamino)-thiazole-5-carbonyl]-phenyl}-acetamide)

The title compound was prepared from 1-amidino-3-p-methoxyphenylthiourea (0.0077 mole) in 10 ml ethanol, N-[4-(2-Bromo-acetyl)-phenyl]-acetamide (0.0077 mole) and tri-ethylamine (0.0077 mole) as per described in the example 39 to provide desired compound. Yield 39.4%. M.P. >280° C., LC MS: 383 (M+1). C19H18N4O3S. TLC: Mobile Phase: Ethyl acetate, Rf: 0.49.

Example 349

([4-Amino-2-(4-methoxy-phenylamino)thiazol-5-yl]-pyridin-3-yl-methanone)

The title compound was prepared from 1-amidino-3-p-methoxyphenylthiourea (0.0077 mole) in 10 ml ethanol, 2-Boromo-1-pyridin-3yl-ethanone (0.0077 mole) and tri-ethylamine (0.0077 mole) as per described in the example 39 to provide desired compound. Yield 62.27%. M.P. >280° C., LC MS: 327 (M+1). C15H12N4OS. TLC: Mobile Phase: Ethyl acetate, Rf: 0.34.

Example 350

([4-Amino-2-(4-methoxy-phenylamino)thiazol-5-yl]-pyridin-4-yl-methanone)

The title compound was prepared from 1-amidino-3-p-methoxyphenylthiourea (0.0077 mole) in 10 ml ethanol, 2-Boromo-1-pyridin-4yl-ethanone (0.0077 mole) and tri-ethylamine (0.0077 mole) as per described in the example 39 to provide desired compound. Yield 77.32%. M.P. >280° C., LC MS: 327 (M+1). C16H14N4O2S. TLC: Mobile Phase: Ethyl acetate, Rf: 0.32.

Example 351

([4-Amino-2-(4-methoxy-phenylamino)thiazol-5-yl]-pyridin-2-yl-methanone)

The title compound was prepared from 1-amidino-3-p-methoxyphenylthiourea (0.0077 mole) in 10 ml ethanol, 2-Boromo-1-pyridin-2yl-ethanone (0.0077 mole) and tri-ethylamine (0.0077 mole) as per described in the example 39 to provide desired compound. Yield 24.22. 2%. M.P. >280° C., LC MS: 327 (M+1). C16H14N4O2S. TLC: Mobile Phase: Ethyl acetate, Rf: 0.27.

Example 352

(5-(4-Methoxy-3,5-dimethyl-pyridin-2-yl)-N2-(4-methoxy-phenyl)-thiazole-2,4-diamine)

The title compound was prepared from 1-amidino-3-p-methoxyphenylthiourea (0.0077 mole) in 10 ml ethanol, 2-Chloromethyl-4-methoxy-3,5-dimeth-yl-pyridine (0.0077 mole) and tri-ethylamine (0.0077 mole) as per described in the example 39 to provide desired compound. Yield 26.32%. M.P. >280° C., LC MS: 357 (M+1). C18H20N4O2S. TLC: Mobile Phase: Ethyl acetate, Rf: 0.39. 1H NMR (CDCl3, δ, ppm): 2.21 (s, 6H, CH3), 3.7 (s, 6H, OCH3), 6.49-7.7 (m, 4H of phenyl and 1H of pyridine), 7.0-7.7 (m, 4H, phenyl), 8.2 (s, 2H of NH2), 10.5 (s, 1H, of NH). IR (KBr, cm-1): 3350, 3260, 3180, 1650, 1585, 1545.

Example 353

(N2-(4-Methoxy-phenyl)-5-[3-Methyl-4-(2,2,2-trifluoro-ethoxy)-pyridin-2-yl]-thiazole-2,4-diamine)

The title compound was prepared from 1-amidino-3-p-methoxyphenylthiourea (0.0077 mole) in 10 ml ethanol, 2-Chloromethyl-5-methyl-4-(2,2,2-trifluoro-ethoxy)-pyridine (0.0077 mole) and tri-ethylamine (0.0077 mole) as per described in the example 39 to provide desired compound. Yield 42.00%. M.P. >280° C., LC MS: 411 (M+1). C18H17F3N4O2S. TLC: Mobile Phase Ethyl acetate, Rf: 0.41.

Example 354

1-(4-Fluoro-phenyl)-3-[5-(4-methoxy-benzoyl)-2-phenylamino-thiazol-4-yl]-urea

The (4-amino-2-phenylamino-thiazol-5-yl)-(4-methoxy-phenyl)-methanone (0.0016 mole) was taken in 5 ml of THF and cooled to 0-5° C. and then slowly p-fluorophenyl isocyanate (0.0015) was added dropwise to it. The reaction mixture was stirred for 30 minutes at RT, the white precipitate was filtered, and then washed with cool THF. Rf: 0.64. Yield 67.98%. LC MS 463 (M+1). M.P. >280° C. M.F.=C24H19FN4O3S. Elemental Analysis: Calculated; C, 62.33; H, 4.14; N, 12.11. Observed; C, 62.35; H, 4.44; N, 12.45. 1H NMR (DMSO-d6, δ, ppm): 3.81 (s, 3H, —OCH3), 6.5-7.0 (m, 7H, aromatic), 7.08-7.69 (m, 6H, aromatic), 8.68 (s, 1H, —NH), 10.87 (s, 2H, —NH urea).

Example 355

1-[2-(4-Chloro-phenylamino)-5-(4-methoxy-benzoyl)-thiazol-4-yl]-3-(4-fluoro-phenyl)-urea The title compound was prepared from ([4-amino-2-(4-chloro-phenylamino)-thiazol-5-yl]-(4-methoxy-phenyl)-methanone) (0.0018 mole) in 10 ml THF and p-fluorophenyl isocyanate (0.0018) as per described in the example 353 to provide desired compound. Yield 70.79%. M.P. >280° C., LC MS: 498 (M+2). C24H18ClFN4O3S. TLC: M.P.: Ethyl acetate, Rf: 0.67. 1H NMR (DMSO-d6, δ, ppm): 3.67 (s, 3H, —OCH3), 6.9-7.1 (m, 6H, aromatic), 7.3-7.7 (m, 6H, aromatic), 8.87 (s, 1H, —NH), 10.91 (s, 2H, —NH urea).

Example 356

1-[2-(4-Chloro-phenylamino)-5-(4-methyl-benzoyl)-thiazol-4-yl]-3-(4-fluoro-phenyl)-urea The title compound was prepared from ((([4-amino-2-(4-chloro-phenylamino)-thiazol-5-yl]-p-tolyl-methanone) (0.0018 mole) in 10 ml THF and p-fluorophenyl isocyanate (0.0018) as per described in the example 353 to provide desired compound. Yield 75.79%. M.P. >280° C., LC MS: 482 (M+2). C24H18ClFN4O2S. TLC: M.P.: Ethyl acetate, Rf: 0.62. Elemental Analysis Calculated; C, 55.10; H, 3.02; N, 11.17;. Observed; C, 55.64; H, 3.52; N, 11.88. 1H NMR (DMSO-d6, δ, ppm): 2.39 (s, 3H, —CH3), 6.9 (m, 6H, aromatic), 7.2-7.7 (m, 6H, aromatic), 8.36 (s, 1H, —NH), 9.61 (s, 2H, —NH urea).

Example 357

1-[5-(4-Chloro-benzoyl)-2-(4-chloro-phenylamino)-thiazol-4-yl]-3-(4-fluoro-phenyl)-urea The title compound was prepared from ([4-amino-2-(4-chloro-phenylamino)-thiazol-5-yl]-(4-chloro-phenyl)-methanone (0.0018 mole) in 10 ml THF and p-fluorophenyl isocyanate (0.0018) as per described in the example 353 to provide desired compound. Yield 69.29%. M.P. >280° C., LC MS: 482 (M+2). C23H15Cl2FN4O2S. TLC: M.P.: Ethyl acetate, Rf: 0.72.

Example 358

1-[2-(4-Chloro-phenylamino)-5-(2,4-dichloro-benzoyl)-thiazol-4-yl]-3-(4-fluoro-phenyl)-urea The title compound was prepared from [4-amino-2-(4-chloro-phenylamino)-thiazol-5-yl]-(2,4-dichloro-phenyl)-methanone (0.0018 mole) in 10 ml THF and p-fluorophenyl isocyanate (0.0018) as per described in the example 353 to give the compound whose M.P. >280° C., yield 62.42%. IR (KBr, Cm-1); 3299, 3085, 1885, 1635, 1510, 1405, 1209, 1012. LC MS shows the 496 (M+), 497 (M+1) and 498 (M+2) peaks. TLC: M.P.: Ethyl acetate, Rf: 0.69., 1H-NMR (DMSO-d6, δ, ppm): 6.98-6.98 (m, 4H, aromatic), 7.2-7.4 (m, 8H, aromatic), 8.32 (s, 1H, —NH), 8.65 (s, 2H, —NH urea), and molecular formula as C23H14Cl3FN4O2S, Elemental Analysis is shown as Calculated; C, 51.56; H, 2.63; N, 10.46; Observed; C, 51.24; H, 2.52; N, 10.54.

Example 359

1-[2-(4-Chloro-phenylamino)-5-(pyridine-3-carbonyl)-thiazol-4-yl]-3-(4-fluoro-phenyl)-urea The title compound was prepared from (4-amino-2-phenylamino-thiazol-5-yl)-pyridin-3-yl-methanone (0.0018 mole) in 10 ml THF and p-fluorophenyl isocyanate (0.0018) as per described in the example 353 to provide desired compound. Yield 35.34%. M.P. >280° C., LC MS: 469 (M+2). C22H15ClFN5O2S. TLC: M.P.: Ethyl acetate, Rf: 0.42.

Example 360

1-[2-(4-Chloro-phenylamino)-5-(pyridine-4-carbonyl)-thiazol-4-yl]-3-(4-fluoro-phenyl)-urea The title compound was prepared from (4-amino-2-phenylamino-thiazol-5-yl)-pyridin-4-yl-methanone (0.0018 mole) in 10 ml THF and p-fluorophenyl isocyanate (0.0018) as per described in the example 353 to provide desired compound. Yield 47.23%. M.P. >280° C., LC MS: 469 (M+2). C22H15ClFN5O2S. TLC: M.P.: Ethyl acetate, Rf: 0.47.

Example 361

1-[2-(4-Chloro-phenylamino)-5-[4-methyl-5-(2,2,2-trifluoro-ethoxy)-pyridin-2-yl]-thiazol-4-yl]-3-(4-fluoro-phenyl)-urea The title compound was prepared from N2-(4-chloro-phenyl)-5-[4-methyl-5-(2,2,2-trifluoro-ethoxy)-pyridin-2-yl]-thiazole-2,4-diamine (0.0018 mole) in 10 ml THF and p-fluorophenyl isocyanate (0.0018) as per described in the example 353 to provide desired compound. Yield 62.43%. M.P. >280° C. LCMS: 553 (M+2). C24H18ClF4N5O2S. TLC:M.P.: Ethyl acetate, Rf: 0.47.

Example 362

1-[2-(4-Methoxy-phenylamino)-5-(4-methyl-benzoyl)-thiazol-4-yl]-3-(4-fluoro-phenyl)-urea The title compound was prepared from ([4-amino-2-(4-methoxy-phenylamino)-thiazol-5-yl]-(4-methoxy-phenyl)-methanone) (0.0018 mole) in 10 ml THF and p-fluorophenyl isocyanate (0.0018) as per described in the example 353 to provide desired compound. Yield 75.79%. M.P. >280° C., LC MS: 477 (M+1). C25H21FN4O3S. TLC: M.P.: Ethyl acetate, Rf: 0.59.

Example 363

1-[5-(4-Chloro-benzoyl)-2-(4-methoxy-phenylamino)-thiazol-4-yl]-3-(4-fluoro-phenyl)-urea The title compound was prepared from [4-amino-2-(4-methoxy-phenylamino)-thiazol-5-yl]-(4-chloro-phenyl)-methanone (0.0018 mole) in 10 ml THF and p-fluorophenyl isocyanate (0.0018) as per described in the example 353 to provide desired compound. Yield 56.34%. M.P. >280° C., LC MS: 498 (M+2). C24H18ClFN4O3S. TLC: M.P.: Ethyl acetate, Rf: 0.62.

Example 364

1-(4-Fluoro-phenyl)-3-[5-(4-methanesulfonyl-benzoyl)-2-(4-methoxy-phenylamino)-thiazol-4-yl]-urea The title compound was prepared from [4-amino-2-(4-methoxy-phenylamino)-thiazol-5-yl]-(4-methansulfonyl-phenyl)-methanone (0.0018 mole) in 10 ml THF and p-fluorophenyl isocyanate (0.0018) as per described in the example 353 to provide desired compound. Yield 56.34%. M.P. >280° C., LC MS: 541 (M+1). C25H21FN4O5S2. TLC: M.P.: Ethyl acetate, Rf: 0.62.

Example 365

1-(4-Fluoro-phenyl)-3-[2-(4-methoxy-phenylamino)-5-(pyridine-4-carbonyl)-thiazol-4-yl]-urea The title compound was prepared from [4-amino-2-(4-methoxy-phenylamino)-thiazol-5-yl]-pyridin-4-yl-methanone (0.0018 mole) in 10 ml THF and p-fluorophenyl isocyanate (0.0018) as per described in the example 353 to provide desired compound. Yield 37.39%. M.P. >280° C., LC MS: 541 (M+1). C23H18FN5O3S. TLC: M.P.: Ethyl acetate, Rf: 0.32.

Example 366

1-(4-Fluoro-phenyl)-3-[5-(5-methoxy-4,6-dimethyl-pyridin-2-yl)-2-(4-methoxy-phenylamino)-thiazol-4-yl]-urea The title compound was prepared from 5-(5-methoxy-4,6-dimethyl-pyridin-2-yl)-N2-(4-methoxy-phenyl)-thiazole-2,4-diamine (0.0018 mole) in 10 ml THF and p-fluorophenyl isocyanate (0.0018) as per described in the example 353 to provide desired compound. Yield 39.67%. M.P. >280° C., LC MS: 494 (M+1). C25H24FN5O3S. TLC: M. P.: Ethyl acetate, Rf: 0.32.

Example 367

1-(4-Fluoro-phenyl)-3-{2-(4-methoxy-phenylamino)-5-[4-methyl-5-(2,2,2-trifluoro-ethoxy)-pyridin-2-yl]-thiazol-4-yl}-urea The title compound was prepared from N2-(4-methoxy-phenyl)-5-[4-methyl-5-(2,2,2-trifluoro-ethoxy)-pyridin-2-yl]-thiazole-2,4-diamine (0.0018 mole) in 10 ml THF and p-fluorophenyl isocyanate (0.0018) as per described in the example 353 to provide desired compound. Yield 62.43%. M.P. >280° C., LC MS: 548(M+1). C25H21F4N5O3S. TLC: M.P.: Ethyl acetate, Rf: 0.47.

Example 368

1-(4-Fluoro-phenyl)-3-[2-(4-methoxy-phenylamino)-5-(pyridine-2-carbonyl)-thiazol-4-yl]-urea The title compound was prepared from [4-amino-2-(4-methoxy-phenylamino)-thiazol-5-yl]-pyridin-2-yl-methanone (0.0018 mole) in 10 ml THF and p-fluorophenyl isocyanate (0.0018) as per described in the example 353 to provide desired compound. Yield 27.39%. M.P. >280° C., LC MS: 541 (M+1). C23H18FN5O3S. TLC: M.P.: Ethyl acetate, Rf: 0.29.

Example 369

N-[4-(Furan-2-carbonyl)-piperazine-1-carbothioyl]-benzamide

A 250 ml, 2-necked round bottom flask was charged with furan-2-yl-piperazin-1-yl-methanone (0.056 mole) and 200 ml toluene and cooled to 0-5° C. Then benzoyl isothiocyanate was added drop wise at 5° C. The reaction mixture was stirred for 24 hr. at room temperature. The white precipitate was filtered out and washed with cold toluene. The precipitate was again re-crystallized with ethyl acetate. Mobile phase: Toluene:Acetonitrile 7:3, Rf: 0.73. LC MS (M+1): 344. C17H17N3O3S. Yield: 78.57%. 1H NMR (DMSO-d6, δ, ppm): 3.26-4.25 (m, 8H of piperazine and 1H of NH), 6.49-6.51 (m, 1H of furan), 7.04-7.08 (m, 1H of furan), 7.29-7.61 (m, 3H of phenyl and 1H of furan), 7.86-7.88 (m, 2H of phenyl). Elemental Analysis: Observed; C, 59.46; H, 4.99; N, 12.24. Calculated; C, 59.76; H, 5.17; N, 12.70.

Example 370

Furan-2-carboxylic acid [4-(furan-2-carbonyl)-piperazine-1-carbothioyl]-amide

A 250 ml, 2-necked round bottom flaskwas charged with furan-2-yl-piperazin-1-yl-methanone (0.056 mole) and 200 ml toluene and cooled to 0-5° C., Then furoyl isothiocyanate was added drop wise at 5° C. The reaction mixture was stirred for 24 hr. at room temperature. The white precipitate was filtered out and washed with cold toluene. The precipitate was re-crystallized with ethyl acetate. Mobile phase: Toluene: Acetonitrile 7:3, Rf: 0.69. LC MS (M+1): 334. C15H15N3O4S. Yield: 67.34%.

Example 371

{2-[4-(Furan-2-carbonyl)-piperazin-1-yl]-4-furan-2-yl-thiazol-5-yl}-p-tolyl-methanone A 25 ml 2-necked round bottom flask was charged with furan-2-carboxylic acid [4-(furan-2-carbonyl)-piperazine-1-carbothioyl]-amide (0.0015 mole) and 10 ml ethanol, followed by p-methylphenacyl bromide (0.0015 mole). The reaction mixture was stirred for 24 hr. This reaction mixture was cooled to −20° C. for 24 hr. The yellow precipitate was filtered and washed with cold methanol. Yield: 56.34%. LC MS (M+1): 448. C24H21N3O4S. M.P.: >280 C; Mobile phase: ethyl acetate:hexane (9:1) Rf: 0.59.

Example 372

[2-[4-(Furan-2-carbonyl)-piperazin-1-yl]-4-furan-2-yl-thiazol-5-yl]-(4-methoxy-phenyl)-methanone The title compound was made from furan-2-carboxylic acid [4-(furan-2-carbonyl)-piperazine-1-carbothioyl]-amide (0.0015 mole) and p-methoxyphenacyl bromide (0.0015 mole) as per example 39. Yield: 56.34%. LC MS (M+1): 464. C24H21N3O5S. M.P.: >280 C; Mobile phase: ethyl acetate:hexane (9:1) Rf: 0.54.

Example 373

(4-Chloro-phenyl)-{2-[4-(furan-2-carbonyl)-piperazin-1-yl]-4-furan-2-yl-thiazol-5-yl}-methanone The title compound was made from furan-2-carboxylic acid [4-(furan-2-carbonyl)-piperazine-1-carbothioyl]-amide (0.0015 mole) and p-chlorophenacyl bromide (0.0015 mole) as per example 39. Yield: 56.34%. LC MS (M+2): 469. C24H18ClN3O4S. M.P.: >280 C; Mobile phase: ethyl acetate:hexane (9:1) Rf: 0.62.

Example 374

(2,4-Dichloro-phenyl)-{2-[4-(furan-2-carbonyl)-piperazin-1-yl]-4-furan-2-yl-thiazol-5-yl}-methanone The title compound was made from furan-2-carboxylic acid [4-(furan-2-carbonyl)-piperazine-1-carbothioyl]-amide (0.0015 mole) and 2,4-dichlorophenacyl bromide (0.0015 mole) as per example 39. Yield: 37.34%. LC MS (M+2): 503. C24H17Cl2N3O4S. M.P.: >280 C; Mobile phase: ethyl acetate:hexane (9:1) Rf: 0.69.

Example 375

{2-[4-(Furan-2-carbonyl)-piperazin-1-yl]-4-furan-2-yl-thiazol-5-yl}-(4-methanesulfonyl-phenyl)-methanone The title compound was made from furan-2-carboxylic acid [4-(furan-2-carbonyl)-piperazine-1-carbothioyl]-amide (0.0015 mole) and p-methylsulfonylphenacyl bromide (0.0015 mole) as per example 39. Yield: 42.34%. LC MS (M+1): 512. C24H21N3O6S2. M.P.: >280 C; Mobile phase: ethyl acetate:hexane (9:1) Rf: 0.71.

Example 376

[2-[4-(Furan-2-carbonyl)-piperazin-1-yl]-4-furan-2-yl-thiazol-5-yl]-pyridin-3-yl-methanone The title compound was made from furan-2-carboxylic acid [4-(furan-2-carbonyl)-piperazine-1-carbothioyl]-amide (0.0015 mole) and 2-bromo-1-pyridin-3-yl-ethanone (0.0015 mole) as per example 39. Yield: 48.34%. LC MS (M+1): 435. C22H18N4O4S. M.P.: >280 C; Mobile phase: ethyl acetate:hexane (9:1) Rf: 0.37.

Example 377

{2-[4-(Furan-2-carbonyl)-piperazin-1-yl]-4-furan-2-yl-thiazol-5-yl}-pyridin-4-yl-methanone The title compound was made from furan-2-carboxylic acid [4-(furan-2-carbonyl)-piperazine-1-carbothioyl]-amide (0.0015 mole) and 2-bromo-1-pyridin-4-yl-ethanone (0.0015 mole) as per example 39. Yield: 37.34%. LC MS (M+1): 435. C22H18N4O4S. M.P.: >280 C; Mobile phase: ethyl acetate:hexane (9:1) Rf: 0.42.

Example 378

Furan-2-yl-[4-{4-furan-2-yl-5-(4-methoxy-3,5-dimethyl-pyridin-2-yl)-thiazol-2-yl]-piperazin-1-yl}-methanone The title compound was made from furan-2-carboxylic acid [4-(furan-2-carbonyl)-piperazine-1-carbothioyl]-amide (0.0015 mole) and 2-chloromethyl-4-methoxy-3,5-dimethyl-pyridine (0.0015 mole) as per Example 39. Yield: 54.34%. LC MS (M+1): 465. C24H24N4O4S. M.P.: >280 C; Mobile phase: ethyl acetate:hexane (9:1) Rf: 0.52.

Example 379

Furan-2-yl-(4-{4-furan-2-yl-5-[3-methyl-4-(2,2,2-trifluoro-ethoxy)-pyridin-2-yl]-thiazol-2-yl}-piperazin-1-yl)-methanone The title compound was made from USA-2 (0.0015 mole) and 2-chloromethyl-3-methyl-4-(2,2,2-trifluoro-ethoxy)-pyridine (0.0015 mole) as per example 39. Yield: 23.47%. LC MS (M+1): 519. C24H21F3N4O4S. M.P.: >280 C; Mobile phase: ethyl acetate:hexane (9:1) Rf: 0.52.

Example 380

{2-[4-(Furan-2-carbonyl)-piperazin-1-yl]-4-furan-2-yl-thiazol-5-yl}-pyridin-2-yl-methanone The title compound was made from furan-2-carboxylic acid [4-(furan-2-carbonyl)-piperazine-1-carbothioyl]-amide (0.0015 mole) and 2-bromo-1-pyridin-2-yl-ethanone (0.0015 mole) as per example 39. Yield: 37.34%. LC MS (M+1): 435. C22H18N4O4S. M.P.: >280 C; Mobile phase: ethyl acetate:hexane (9:1) Rf: 0.32.

Example 381

{2-[4-(Furan-2-carbonyl)-piperazin-1-yl]-4-phenyl-thiazol-5-yl}-p-tolyl-methanone The title compound was made from N-[4-(Furan-2-carbonyl)-piperazine-1-carbothioyl]-benzamide (0.0015 mole) and p-methylphenacyl bromide (0.0015 mole) as per example 39. Yield: 66.34%. LC MS (M+1): 458. C26H23N3O3S. M.P.: >280 C; Mobile phase: ethyl acetate:hexane (9:1) Rf: 0.67.

Example 382

{2-[4-(Furan-2-carbonyl)-piperazin-1-yl]-4-phenyl-thiazol-5-yl}-(4-methoxy-phenyl)-methanone The title compound was made from N-[4-(Furan-2-carbonyl)-piperazine-1-carbothioyl]-benzamide (0.0015 mole) and p-methoxyphenacyl bromide (0.0015 mole) as per example 39. Yield: 47.44%. LC MS (M+1): 474.

C26H23N3O4S. M.P.: >280 C; Mobile phase: ethyl acetate: hexane (9:1) Rf: 0.62. Elemental Analysis: Observed; C, 65.94; H, 4.90; N, 8.87. Calculated; C, 65.67; H, 4.77; N, 8.97. 1H NMR (DMSO-d6, δ, ppm): 3.7-3.8 (m, 8H of piperazine and 3H of OCH3), 6.6-6.7 (m, 2H of furan and 1H of phenyl), 7.05-7.4 (m, 1H of furan and 6H phenyl), 7.8-8.0 (m, 2H of phenyl).

Example 383

(4-Chloro-phenyl)-{2-[4-(furan-2-carbonyl)-piperazin-1-yl]-4-phenyl-thiazol-5-yl}-methanone The title compound was made from N-[4-(Furan-2-carbonyl)-piperazine-1-carbothioyl]-benzamide (0.0015 mole) and p-chlorophenacyl bromide (0.0015 mole) as per example 39. Yield: 56.34%. LC MS (M+2): 479. C25H20ClN3O3S. M.P.: >280 C; Mobile phase: ethyl acetate:hexane (9:1) Rf: 0.59.

Example 384

(2,4-Dichloro-phenyl)-{2-[4-(furan-2-carbonyl)-piperazin-1-yl]-4-phenyl-thiazol-5-yl}-methanone The title compound was made from N-[4-(Furan-2-carbonyl)-piperazine-1-carbothioyl]-benzamide (0.0015 mole) and 2,4-dichlorolphenacyl bromide (0.0015 mole) as per example 39. Yield: 37.45%. LC MS (M+2): 513. C25H19Cl2N3O3S. M.P.: >280 C; Mobile phase: ethyl acetate:hexane (9:1) Rf: 0.57.

Example 385

{2-[4-(Furan-2-carbonyl)-piperazin-1-yl]-4-phenyl-thiazol-5-yl}-(4-methanesulfonyl-phenyl)-methanone The title compound was made from USA-2 (0.0015 mole) and p-sulfonylphenacyl bromide (0.0015 mole) as per US-1. Yield: 42.34%. LC MS (M+1): 522. M.P.: >280 C; Mobile phase: ethyl acetate:hexane (9:1) Rf: 0.71., IR (KBr, Cm-1); 3333, 3114, 2930, 2866, 1757, 1681, 1616, 1291, 1091, 1H NMR (DMSO-d6, δ, ppm): 3.1-3.8 (m, 8H of piperazine and 3H of SO2CH3), 6.6 (s, 1H of furan), 7.0-8.3 (series of peaks like m, 2H of furan and 9H phenyl), Elemental Analysis Observed; C, 59.87; H, 4.44; N, 8.06. Calculated; C, 59.62; H, 4.89; N, 8.32., and molecular formula as C26H23N3O5S2.

Example 386

{2-[4-(Furan-2-carbonyl)-piperazin-1-yl]-4-phenyl-thiazol-5-yl}-pyridin-3-yl-methanone The title compound was made from N-[4-(Furan-2-carbonyl)-piperazine-1-carbothioyl]-benzamide (0.0015 mole) and 2-bromo-1-pyridin-3-yl-ethanone (0.0015 mole) as per example 39. Yield: 48.34%. LC MS (M+1): 445. C24H20N4O3S. M.P.: >280 C; Mobile phase: ethyl acetate: hexane (9:1) Rf: 0.33.

Example 387

{2-[4-(Furan-2-carbonyl)-piperazin-1-yl]-4-phenyl-thiazol-5-yl}-pyridin-4-yl-methanone The title compound was made from N-[4-(Furan-2-carbonyl)-piperazine-1-carbothioyl]-benzamide (0.0015 mole) and 2-bromo-1-pyridin-4-yl-ethanone (0.0015 mole) as per example 39. Yield: 37.34%. LC MS (M+1): 445. C24H20N4O3S. M.P.: >280 C; Mobile phase: ethyl acetate: hexane (9:1) Rf: 0.42.

Example 388

Furan-2-yl-{4-[5-(4-methoxy-3,5-dimethyl-pyridin-2-yl)-4-phenyl-thiazol-2-yl]-piperazin-1-yl}-methanone The title compound was made from N-[4-(Furan-2-carbonyl)-piperazine-1-carbothioyl]-benzamide (0.0015 mole) and 2-chloromethyl-4-methoxy-3,5-dimethyl-pyridine (0.0015 mole) as per example 39. Yield: 54.34%. LC MS (M+1): 475. C26H26N4O3S. M.P.: >280 C; Mobile phase: ethyl acetate:hexane (9:1) Rf: 0.27.

Example 389

Furan-2-yl-(4-{5-[3-methyl-4-(2,2,2-trifluoro-ethoxy)-pyridin-2-yl]-4-phenyl-thiazol-2-yl}-piperazin-1-yl)-methanone The title compound was made from N-[4-(Furan-2-carbonyl)-piperazine-1-carbothioyl]-benzamide (0.0015 mole) and 2-chloromethyl-3-methyl-4-(2,2,2-trifluoro-ethoxy)-pyridine (0.0015 mole) as per example 39. Yield: 23.47%. LC MS (M+1): 529. C26H23F3N4O3S. M.P.: >280 C; Mobile phase: ethyl acetate:hexane (9:1) Rf: 0.52.

Example 390

{2-[4-(Furan-2-carbonyl)-piperazin-1-yl]-4-phenyl-thiazol-5-yl}-pyridin-2-yl-methanone The title compound was made from N-[4-(Furan-2-carbonyl)-piperazine-1-carbothioyl]-benzamide (0.0015 mole) and the 2-bromo-1-pyridin-2-yl-ethanone (0.0015 mole) as per example 39. Yield: 37.34%. LC MS (M+1): 445. C24H20N4O3S. M.P.: >280 C; Mobile phase: ethyl acetate: hexane (9:1) Rf: 0.32.

Example 391

Bis-[2-(2-methoxy-phenylamino)-4-phenyl-thiazol-5-yl]-methanone

The title compound was made from ethyl 1-(diethylamino-phenyl-methylene)-3-(2-methoxy-phenyl)-thiourea (0.0026 moles) and 1,3-dichloroacetone (0.0013 moles) as described in example 39. Yield 43%. LC MS (M+1) 591, M.P.: >285° C., Rf; 0.46. C33H26N4O3S2

Example 392

Bis-[2-(3-methoxy-phenylamino)-4-phenyl-thiazol-5-yl]-methanone

The title compound was made from ethyl 1-(diethylamino-phenyl-methylene)-3-(3-methoxy-phenyl)-thiourea (0.0026 moles) and 1,3-dichloroacetone (0.0013 moles) as described in example 39. Yield 54%. LC MS (M+1) 591, M.P.: >285° C., Rf; 0.39. C33H26N4O3S2

Example 393

Bis-[2-(4-methoxy-phenylamino)-4-phenyl-thiazol-5-yl]-methanone

The title compound was made from ethyl 1-(diethylamino-phenyl-methylene)-3-(4-methoxy-phenyl)-thiourea (0.0026 moles) and 1,3-dichloroacetone (0.0013 moles) as described in example 39. Yield 62%. LC MS (M+1) 591, M.P.: >285° C., Rf; 0.37. C33H26N4O3S2

Example 394

Bis-[2-(4-methyl-phenylamino)-4-phenyl-thiazol-5-yl]-methanone

The title compound was made from ethyl 1-(diethylamino-phenyl-methylene)-3-(4-methyl-phenyl)-thiourea (0.0026 moles) and 1,3-dichloroacetone (0.0013 moles) as described in example 39. Yield 49%. LC MS (M+1) 559, M.P: >285° C., Rf; 0.42. C32H26N4O2S2

Example 395

Diphenyl [carbonylbis(4-Benzyl-1,3-thiazole-5,2-diyl)]bis-carbamate

The title compound was made from ethyl ({[1-(diphenylamino) (phenyl)methylene]amino}carbonothioyl)carbamate (0.0026 moles) and 1,3-dichloroacetone (0.0013 moles) as described in example 39. Yield 49%. LC MS (M+1) 559, M.P: >285° C., Rf; 0.42. C33H22N4O5S2

Example 396

N-(4-methyl-5-(4-oxo-3-p-tolyl-3,4-dihydroquinazolin-2-yl)thiazol-2-yl)furan-2-carboxamide The title compound was prepared from 1-[1-Diethylamino-1-phenyl-meth-(E)-ylidene]-3-(furan-2-carbonyl)-thiourea and 2-Chloro methyl-3-(4-phenyl)-3H-quinazoline-4-one as described in example 201. Yield: 52.77%, M.P. >275: LC-MS (m/e):443; (M+1); Rf; 0.59.

EXAMPLES OF COMPOUNDS

Examples of Compounds that may be used in practicing this invention include but are not limited to the various general structures depicted below, as well as the specific exemplary compounds with specific substituents listed in the following tables. The tables give cross-references to the above "Example" numbers. The "% Protection" is defined in Example 397. The "NF-κB Inhibition @ 1 μM" and "AP-1 Inhibition @ 1 μM" were determined as described in Example 398:

TABLE 1

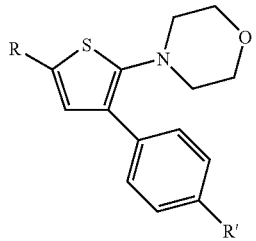

| R | R' | % Protection P | NFkB inhibition @ 1 uM | AP-1 inhibition @ 1 uM | Example No. |
|---|---|---|---|---|---|
| H | CO-Phenyl | 53.46 | NT | NT | Example 42 |
| H | CO-p-methyl phenyl | 5.33 | −15.26 | 27.3 | Example 43 |
| H | CO-p-methoxy phenyl | 66.67 | 14.88 | 55.37 | Example 44 |
| H | CO-p-Chloro phenyl | 53.46 | NT | NT | Example 45 |
| H | CO-2,4-Dichloro phenyl | 68.31 | NT | NT | Example 46 |
| H | CO-p-sulfanyl phenyl | 5 | −1.5 | 21.23 | Example 47 |
| H | CO-p-sulfonyl phenyl | 30 | NT | NT | Example 48 |
| H | CO-p-acetyl amino phinyl | 68.31 | NT | NT | Example 49 |
| H | CO-3-pyridin | 6.9 | NT | NT | Example 50 |
| H | CO-4-pyridine | 39.65 | 8.36 | 16.77 | Example 51 |
| H | 4-methoxy-3,5-dimethyl pyridine | 38 | 7.26 | 30.77 | Example 37 |
| H | 3-methyl-4-(2,2,2-trifluoroethoxy)pyridine | 10.89 | NT | NT | Example 38 |
| H | 3,4,5-trimethoxypyridine | 19.65 | NT | NT | Example 39 |
| SO2CH3 | CO-Phenyl | 17.82 | NT | NT | Example 54 |
| SO2CH3 | CO-p-methyl phenyl | −13.54 | NT | NT | Example 55 |
| SO2CH3 | CO-p-methoxyphenyl | 77.78 | 18.07 | 76.09 | Example 56 |
| SO2CH3 | CO-p-Chloro phenyl | 26.88 | NT | NT | Example 57 |
| SO2CH3 | CO-2,4-Dichloro phenyl | 50 | NT | NT | Example 58 |
| SO2CH3 | CO-p-sulfanyl phenyl | 45.83 | NT | NT | Example 59 |
| SO2CH3 | CO-p-sulfonyl phenyl | 59.88 | NT | NT | Example 60 |
| SO2CH3 | CO-p-acetyl amino phinyl | 25 | NT | NT | Example 61 |
| SO2CH3 | CO-3-pyridin | 0 | NT | NT | Example 62 |
| SO2CH3 | CO-4-pyridine | 50 | 10.47 | 5.71 | Example 63 |
| SO2CH3 | 4-methoxy-3,5-dimethyl pyridine | 61.11 | 5.81 | −7.93 | Example 52 |
| SO2CH3 | 3-methyl-4-(2,2,2-trifluoroethoxy)pyridine | 2.08 | −2.17 | 25.04 | Example 53 |
| NHCOCH3 | CO-Phenyl | 40 | 24.23 | −2.98 | Example 66 |
| NHCOCH3 | CO-p-methyl phenyl | 7.67 | NT | NT | Example 67 |
| NHCOCH3 | CO-p-methoxy phenyl | 40 | NT | NT | Example 68 |
| NHCOCH3 | CO-p-Chloro phenyl | −21.78 | NT | NT | Example 69 |
| NHCOCH3 | CO-2,4-Dichlorophenyl | 39.16 | 18.58 | 54.04 | Example 70 |
| NHCOCH3 | CO-p-sulfanyl phenyl | 2.5 | 7.6 | 27.75 | Example 71 |
| NHCOCH3 | CO-p-sulfonyl phenyl | 50 | NT | NT | Example 72 |
| NHCOCH3 | CO-p-acetyl amino phinyl | −23.49 | −28.62 | 19.87 | Example 73 |

TABLE 1-continued

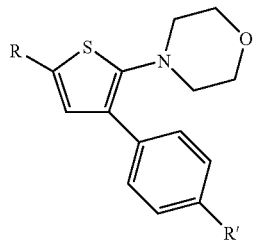

| R | R' | % Protection P | NFkB inhibition @ 1 uM | AP-1 inhibition @ 1 uM | Example No. |
| --- | --- | --- | --- | --- | --- |
| NHCOCH3 | CO-3-pyridin | 34 | NT | NT | Example 74 |
| NHCOCH3 | CO-4-pyridine | 45.69 | 17.44 | 45.5 | Example 75 |
| NHCOCH3 | 4-methoxy-3,5-dimethyl pyridine | 49.05 | −4.95 | 26.2 | Example 64 |
| NHCOCH3 | 3-methyl-4-(2,2,2-trifluoroethoxy)pyridine | 30 | NT | NT | Example 65 |
| Cl | CO-Phenyl | −48.27 | NT | NT | Example 78 |
| Cl | CO-p-methyl phenyl | −31.03 | NT | NT | Example 79 |
| Cl | CO-p-methoxyphenyl | 18.85 | −2.91 | 30.55 | Example 80 |
| Cl | CO-p-Chloro phenyl | 20 | NT | NT | Example 81 |
| Cl | CO-2,4-Dichloro phenyl | 22.75 | 0.6 | 34.27 | Example 82 |
| Cl | CO-p-sulfanyl phenyl | 27 | NT | NT | Example 83 |
| Cl | CO-p-sulfonyl phenyl | 23 | −11.66 | 30.88 | Example 84 |
| Cl | CO-p-acetyl amino phinyl | 20 | −17.34 | 22.58 | Example 85 |
| Cl | CO-3-pyridin | 28.09 | 3.6 | 15.17 | Example 86 |
| Cl | CO-4-pyridine | 35 | NT | NT | Example 87 |
| Cl | 4-methoxy-3,5-dimethyl pyridine | 17 | NT | NT | Example 76 |
| Cl | 3-methyl-4-(2,2,2-trifluoroethoxy)pyridine | 23 | NT | NT | Example 77 |
| 3-pyridine | CO-Phenyl | 6.09 | 7.91 | 59.49 | Example 90 |
| 3-pyridine | CO-p-methylphenyl | 25.33 | 1.28 | 48.98 | Example 91 |
| 3-pyridine | CO-p-methoxy phenyl | 68.98 | NT | NT | Example 92 |
| 3-pyridine | CO-p-Chloro phenyl | 0 | NT | NT | Example 93 |
| 3-pyridine | CO-2,4-Dichloro phenyl | −51.4 | NT | NT | Example 94 |
| 3-pyridine | CO-p-sulfanyl phenyl | 42.44 | 11.24 | 64.02 | Example 95 |
| 3-pyridine | CO-p-sulfonyl phenyl | 46.75 | −12.88 | 37.72 | Example 96 |
| 3-pyridine | CO-p-acetyl amino phinyl | 46.75 | NT | NT | Example 97 |
| 3-pyridine | CO-3-pyridin | 42 | NT | NT | Example 98 |
| 3-pyridine | CO-4-pyridine | 26.04 | NT | NT | Example 99 |
| 3-pyridine | 4-methoxy-3,5-dimethyl pyridine | −18.05 | NT | NT | Example 88 |
| 3-pyridine | 3-methyl-4-(2,2,2-trifluoroethoxy)pyridine | −18.05 | NT | NT | Example 89 |
| 4-Pyridine | CO-Phenyl | 52 | NT | NT | Example 102 |
| 4-Pyridine | CO-p-methyl phenyl | −30.79 | 10.32 | 4.35 | Example 103 |
| 4-Pyridine | CO-p-methoxy phenyl | 43.47 | NT | NT | Example 104 |
| 4-Pyridine | CO-p-Chloro phenyl | 47.22 | NT | NT | Example 105 |
| 4-Pyridine | CO-2,4-Dichloro phenyl | −75.24 | NT | NT | Example 106 |
| 4-Pyridine | CO-p-sulfanyl phenyl | −42.44 | 1.69 | 19.05 | Example 107 |
| 4-Pyridine | CO-p-sulfonyl phenyl | 54.24 | −8.31 | 46.59 | Example 108 |
| 4-Pyridine | CO-p-acetyl amino phinyl | −75.24 | NT | NT | Example 109 |
| 4-Pyridine | CO-3-pyridin | −6.93 | NT | NT | Example 110 |
| 4-Pyridine | CO-4-pyridine | 59.08 | NT | NT | Example 111 |
| 4-Pyridine | 4-methoxy-3,5-dimethyl pyridine | 54.24 | 5.21 | 47.43 | Example 100 |
| 4-Pyridine | 3-methyl-4-(2,2,2-trifluoroethoxy)pyridine | 47 | NT | NT | Example 101 |

TABLE 2

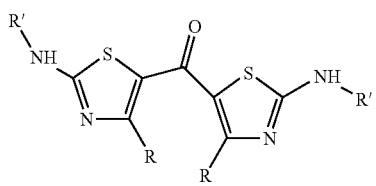

| R | R' | % Protection P | NFkB inhibition @ 1 uM | AP-1 inhibition @ 1 uM | Example No. |
| --- | --- | --- | --- | --- | --- |
| CH3 | CH3 | 58.62 | 22.14 | 51.05 | Example 117 |
| CH3 | Ph | 40.89 | 8.84 | 33.36 | Example 118 |
| CH3 | p-ClPh | 45.46 | 8.39 | 26.01 | Example 119 |

TABLE 2-continued

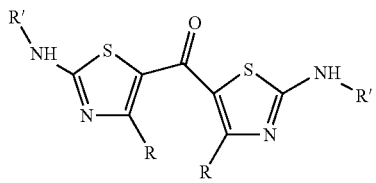

| R | R' | % Protection P | NFkB inhibition @ 1 uM | AP-1 inhibition @ 1 uM | Example No. |
|---|---|---|---|---|---|
| CH3 | COPh | 64.62 | 20.3 | 76.25 | Example 120 |
| CH3 | CO-Furan | 62 | NT | NT | Example 121 |
| CH3 | NHCOOCH3 | 23.89 | NT | NT | Example 123 |
| CH3 | NHCOOC2H5 | 65.66 | 20.06 | 71.56 | Example 124 |
| Ph | CH3 | 23.24 | 27.08 | 23.8 | Example 125 |
| Ph | Ph | 64.54 | 22.19 | 27.11 | Example 126 |
| Ph | p-ClPh | 43.49 | NT | NT | Example 127 |
| Ph | COPh | 34 | NT | NT | Example 128 |
| Ph | CO-Furan | 55 | NT | NT | Example 129 |
| Ph | NHCOOCH3 | 40.78 | 12.78 | 9.2 | Example 130 |
| Ph | NHCOOC2H5 | 69.77 | NT | NT | Example 131 |
| Ph | (C2H5)2 | 47 | NT | NT | Example 132 |
| Ph | CO-p-MethoxyPh | 59 | NT | NT | Example 391 |
| Ph | p-MethylPh | 62 | NT | NT | Example 392 |
| Ph | o-MethoxyPh | 32 | NT | NT | Example 393 |
|  | m-MethoxyPh | 56 | 18.74 | 41.92 | Example 394 |
| Ph | p-MethoxyPh | 66 | NT | NT | Example 395 |
| Benzyl | CH3 | 19.09 | 17.74 | 24.53 | Example 133 |
| Benzyl | Ph | 75.69 | 67.87 | 72.77 | Example 134 |
| Benzyl | p-ClPh | 34.72 | 39.98 | 41.43 | Example 135 |
| Benzyl | COPh | 45.13 | 44.46 | 32.23 | Example 136 |
| Benzyl | CO-Furan | 47.22 | 7.69 | 51.3 | Example 137 |
| Benzyl | NHCOOCH3 | 88.89 | 55.56 | 83.62 | Example 138 |
| Benzyl | NHCOOC2H5 | 69.61 | 62.63 | 74.4 | Example 139 |

TABLE 3

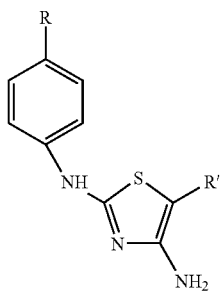

| R | R' | % Protection P | NFkB inhibition @ 1 uM | AP-1 inhibition @ 1 uM | Example No. |
|---|---|---|---|---|---|
| H | p-methoxy benzoyl | 30.55 | −39.33 | −70.59 | Example 114 |
| H | p-methyl benzoyl | 12.25 | NT | NT | Example 321 |
| H | p-chloro benzoyl | 23.98 | NT | NT | Example 322 |
| H | 2,4-dichloro benzoyl | 43 | NT | NT | Example 323 |
| H | p-methylsulfonyl benzoyl | 55 | NT | NT | Example 324 |
| H | p-acetyl amino benzoyl | 12 | NT | NT | Example 325 |
| H | 3-pyridinoyl | 34 | NT | NT | Example 326 |
| H | 4-pyridinoyl | 32 | NT | NT | Example 327 |
| H | 4-methoxy-3,5-dimethyl pyridinyl | 76 | NT | NT | Example 328 |
| H | 3-methyl-4-(2,2,2-trifluoroethoxy)pyridinyl | 54 | NT | NT | Example 329 |
| H | 2-pyridinoyl | 24 | NT | NT | Example 330 |
| Cl | p-methoxy benzoyl | 62.26 | −10.62 | 27.39 | Example 331 |
| Cl | p-methyl benzoyl | 36 | 0.13 | −32.18 | Example 332 |
| Cl | p-chloro benzoyl | 34.59 | 8.19 | 14.23 | Example333 |
| Cl | 2,4-dichloro benzoyl | 28.3 | −38.54 | 37.62 | Example 334 |
| Cl | p-methylsulfonyl benzoyl | 30.32 | NT | NT | Example 335 |
| Cl | p-acetyl amino benzoyl | 28.3 | NT | NT | Example 336 |

TABLE 3-continued

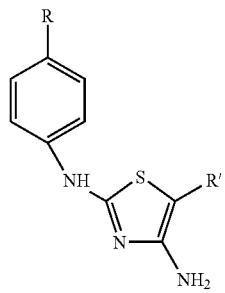

| R | R' | % Protection P | NFkB inhibition @ 1 uM | AP-1 inhibition @ 1 uM | Example No. |
|---|---|---|---|---|---|
| Cl | 3-pyridinoyl | 18.23 | −93.38 | −37.01 | Example 337 |
| Cl | 4-pyridinoyl | 25.78 | −84.08 | −89.08 | Example 338 |
| Cl | 4-methoxy-3,5-dimethyl pyridinyl | 12 | NT | NT | Example 339 |
| Cl | 3-methyl-4-(2,2,2-trifluoroethoxy)pyridinyl | 34 | −18.22 | 57.3 | Example 340 |
| Cl | 2-pyridinoyl | 32 | NT | NT | Example 341 |
| OCH3 | p-methoxy benzoyl | 76 | NT | NT | Example 342 |
| OCH3 | p-methyl benzoyl | 54 | NT | NT | Example 343 |
| OCH3 | p-chloro benzoyl | 79.8 | 49.01 | 70.28 | Example 344 |
| OCH3 | 2,4-dichloro benzoyl | 34.59 | NT | NT | Example 345 |
| OCH3 | p-methylsulfonyl benzoyl | 28.3 | −4.13 | 64.63 | Example 346 |
| OCH3 | p-acetyl amino benzoyl | 30.32 | NT | NT | Example 347 |
| OCH3 | 3-pyridinoyl | 28.3 | NT | NT | Example 348 |
| OCH3 | 4-pyridinoyl | 18.23 | −35.86 | 51.52 | Example 349 |
| OCH3 | 4-methoxy-3,5-dimethyl pyridinyl | 25.78 | NT | NT | Example 350 |
| OCH3 | 3-methyl-4-(2,2,2-trifluoroethoxy)pyridinyl | 27 | −35.86 | 51.52 | Example 351 |
| OCH3 | 2-pyridinoyl | 23 | NT | NT | Example 352 |

TABLE 4

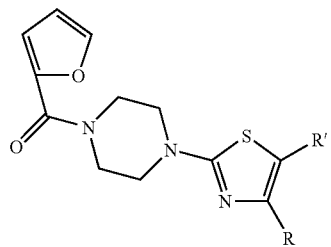

| R | R' | % Protection P | NFkB inhibition @ 1 uM | AP-1 inhibition @ 1 uM | Example No. |
|---|---|---|---|---|---|
| Furan | p-methyl benzoyl | 34 | 10.37 | 25.65 | Example 371 |
| Furan | p-methoxy benzoyl | 52.21 | NT | NT | Example 372 |
| Furan | p-Chloro benzoyl | 42 | −6.07 | 26.93 | Example 373 |
| Furan | 2,4-Dichloro benzoyl | 62.63 | 6.25 | 46.22 | Example 374 |
| Furan | p-methylsulfonyl benzoyl | 49 | −13.24 | 22.11 | Example 375 |
| Furan | 3-pyridinoyl | 33 | −14.11 | 45.91 | Example 376 |
| Furan | 4-pyridinoyl | 32 | −7.88 | 4.84 | Example 377 |
| Furan | 4-methoxy-3,5-dimethyl pyridin-2-yl | 84.21 | 22.05 | 43.26 | Example 378 |
| Furan | 3-methyl-4-(2,2,2-trifluoroethoxy)pyridin-2-yl | 62.42 | 51.11 | 3.23 | Example 379 |
| Furan | 2-pyridinoyl | 42 | NT | NT | Example 380 |
| Ph | p-methyl benzoyl | 53 | −1.91 | 10.42 | Example 381 |
| Ph | p-methoxy benzoyl | 45.96 | NT | NT | Example 382 |
| Ph | p-Chloro benzoyl | 62 | −0.23 | 13.28 | Example 383 |
| Ph | 2,4-Dichloro benzoyl | 71.61 | −1.4 | 42.53 | Example 384 |
| Ph | p-methylsulfonyl benzoyl | 67 | −15.1 | 6.44 | Example 385 |
| Ph | 3-pyridinoyl | 23 | 52.83 | 22.49 | Example 386 |
| Ph | 4-pyridinoyl | 32 | NT | NT | Example 387 |
| Ph | 4-methoxy-3,5-dimethyl pyridin-2-yl | 73.4 | 7.64 | 52.06 | Example 388 |
| Ph | 3-methyl-4-(2,2,2-trifluoroethoxy)pyridin-2-yl | 61.61 | 30.74 | 42.45 | Example 389 |
| Ph | 2-pyridinoyl | 17 | 0.47 | 40.89 | Example 390 |

TABLE 5

[Structure: bis(morpholino-thiophene) ketone with two p-R-phenyl substituents, linker (CH2)n]

| R | n | % Protection P | NFkB inhibition @ 1 uM | AP-1 inhibition @ 1 uM | Example No. |
|---|---|---|---|---|---|
| SO2CH3 | 1 | 55.65 | | | Example 112 |
| NHCOCH3 | 1 | 45.54 | | | Example 113 |
| Cl | 1 | 56.57 | | | Example 114 |

TABLE 6

[Structure: 2-(R-NH)-5-R'-4-(4-pyridinyl)thiazole]

| R | R' | % Protection P | NFkB inhibition @ 1 uM | AP-1 inhibition @ 1 uM | Example No. |
|---|---|---|---|---|---|
| CH3 | COPhenyl | 90.92 | | | Example 115 |

TABLE 7

[Structure: 2-(4-R-phenylamino)-5-R'-4-[N'-(4-fluorophenyl)ureido]thiazole]

| R | R' | % Protection P | NFkB inhibition @ 1 uM | AP-1 inhibition @ 1 uM | Example No. |
|---|---|---|---|---|---|
| H | p-methoxy benzoyl | 45.49 | 34.2 | 2.59 | Example 116 |
| Cl | p-methoxy benzoyl | 82.49 | 59.1 | 62.02 | Example 353 |
| Cl | p-methyl benzoyl | 26.27 | NT | NT | Example 354 |
| Cl | p-Chloro benzoyl | 62.57 | NT | NT | Example 355 |
| Cl | 2,4-Dichloro benzoyl | 69.54 | 54.62 | 48.44 | Example 356 |
| Cl | 3-pyridinyl | 24.27 | NT | NT | Example 357 |
| Cl | 4-pyridinyl | 72.54 | NT | NT | Example 358 |
| Cl | 3-methyl-4-(2,2,2-trifluoroethoxy)pyridine | 64.23 | NT | NT | Example 359 |
| OCH3 | p-methyl benzoyl | 69.84 | NT | NT | Example 360 |
| OCH3 | p-Chloro benzoyl | 77.89 | NT | NT | Example 361 |
| OCH3 | p-sulfonyl benzoyl | 61.34 | NT | NT | Example 362 |
| OCH3 | 4-pyridinyl | 54.54 | NT | NT | Example 363 |
| OCH3 | 4-methoxy-3,5-dimethyl pyridine | 66.78 | NT | NT | Example 364 |
| OCH3 | 3-methyl-4-(2,2,2-trifluoroethoxy)pyridine | 69.56 | NT | NT | Example 365 |
| OCH3 | 2-pyridinyl | 19.14 | NT | NT | Example 366 |

TABLE 8

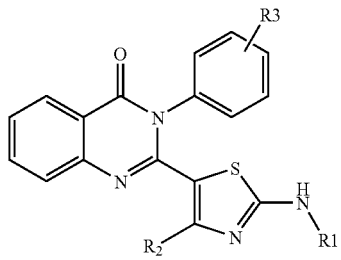

| R1 | R2 | R3 | % Protection | NFkB inhibition @ 1 uM | AP-1 inhibition @ 1 uM | Example No |
|---|---|---|---|---|---|---|
| COOC2H5 | CH3 | H | 12.00% | 19 | −13 | 154 |
| COOCH3 | CH3 | H | 0 | 24 | −1 | 155 |
| CH3 | CH3 | H | NT | | | 156 |
| Ph | CH3 | H | 12 | 25 | 16 | 157 |
| p-Cl Ph | CH3 | H | 4 | −9 | −20 | 158 |
| COOC2H5 | Ph | H | 75% | 80 | 7 | 159 |
| COOCH3 | Ph | H | NT | | | 160 |
| Ph | Ph | H | 60 | 80 | 7 | 161 |
| Benzoyl | Ph | H | 87% | 58 | 17 | 162 |
| p-CH3 Benzoyl | Ph | H | 77 | 88 | 68 | 163 |
| Furoyl | Ph | H | 66 | 2 | 53 | 164 |
| p-Cl Ph | Ph | H | 87% | −47 | 27 | 165 |
| COOC2H5 | CH3 | 2-CH3 | NT | 21 | 14 | 166 |
| COOCH3 | CH3 | 2-CH3 | NT | | | 167 |
| CH3 | CH3 | 2-CH3 | 35 | 16 | 67 | 168 |
| Ph | CH3 | 2-CH3 | 42 | 21 | 60 | 169 |
| p-Cl Ph | CH3 | 2-CH3 | 45 | | | 170 |
| COOC2H5 | Ph | 2-CH3 | 52 | 23 | 52 | 171 |
| COOCH3 | Ph | 2-CH3 | NT | 0 | 25 | 172 |
| CH3 | Ph | 2-CH3 | NT | | | 173 |
| Ph | Ph | 2-CH3 | NT | | | 174 |
| Benzoyl | Ph | 2-CH3 | NT | | | 175 |
| p-CH3 Benzoyl | Ph | 2-CH3 | NT | −8 | 29 | 176 |
| Furoyl | Ph | 2-CH3 | NT | | | 177 |
| p-Cl Ph | Ph | 2-CH3 | 51 | nt | nt | 178 |
| COOC2H5 | CH3 | 3-CH3 | NT | | | 179 |
| COOCH3 | CH3 | 3-CH3 | NT | | | 180 |
| CH3 | CH3 | 3-CH3 | nt | 10 | 20 | 181 |
| Ph | CH3 | 3-CH3 | NT | | | 182 |
| p-Cl Ph | CH3 | 3-CH3 | NT | 2 | 39 | 183 |
| COOC2H5 | Ph | 3-CH3 | NT | | | 184 |
| COOCH3 | Ph | 3-CH3 | NT | | | 185 |
| CH3 | Ph | 3-CH3 | nt | 23 | 10 | 186 |
| Ph | Ph | 3-CH3 | NT | | | 187 |
| Benzoyl | Ph | 3-CH3 | NT | 42 | 63 | 188 |
| p-Cl Ph | Ph | 3-CH3 | 38 | −4 | 83 | 189 |
| COOC2H5 | CH3 | 4-CH3 | 23.97 | | | 190 |
| Ph | CH3 | 4-CH3 | NT | | | 191 |
| p-Cl Ph | CH3 | 4-CH3 | 37 | 12 | 2 | 192 |
| COOC2H5 | Ph | 4-CH3 | 31 | 2 | 11 | 193 |
| COOCH3 | Ph | 4-CH3 | NT | | | 194 |
| CH3 | Ph | 4-CH3 | NT | | | 195 |
| Ph | Ph | 4-CH3 | NT | 38 | 10 | 196 |
| Benzoyl | Ph | 4-CH3 | NT | | | 197 |
| p-CH3 Benzoyl | Ph | 4-CH3 | NT | | | 198 |
| Furoyl | Ph | 4-CH3 | NT | | | 199 |
| p-Cl Ph | Ph | 4-CH3 | 56 | −16 | 2 | 200 |
| COOC2H5 | CH3 | 2-OCH3 | NT | | | 201 |
| Ph | CH3 | 2-OCH3 | NT | | | 202 |
| p-Cl Ph | CH3 | 2-OCH3 | 27 | NT | NT | 203 |
| COOCH3 | Ph | 2-OCH3 | NT | | | 204 |
| CH3 | Ph | 2-OCH3 | 56 | 61 | 90 | 205 |
| Ph | Ph | 2-OCH3 | NT | | | 206 |
| Furoyl | Ph | 2-OCH3 | NT | | | 207 |
| p-Cl Ph | Ph | 2-OCH3 | 31 | NT | NT | 208 |
| COOC2H5 | CH3 | 3-OCH3 | NT | 29 | 5 | 209 |
| Ph | CH3 | 3-OCH3 | | | | 210 |
| p-Cl Ph | CH3 | 3-OCH3 | NT | | | 211 |
| COOC2H5 | Ph | 3-OCH3 | NT | | | 212 |
| Ph | Ph | 3-OCH3 | 38 | 35 | 33 | 213 |
| Benzoyl | Ph | 3-OCH3 | NT | 34 | 30 | 214 |

TABLE 8-continued

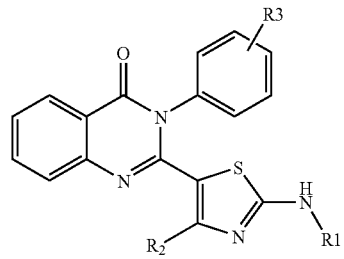

| R1 | R2 | R3 | % Protection | NFkB inhibition @ 1 uM | AP-1 inhibition @ 1 uM | Example No |
|---|---|---|---|---|---|---|
| COOC2H5 | CH3 | 4-OCH3 | 25 | 34 | −6 | 215 |
| Ph | CH3 | 4-OCH3 | NT | | | 216 |
| p-Cl Ph | CH3 | 4-OCH3 | 50 | −38 | −43 | 217 |
| COOC2H5 | Ph | 4-OCH3 | 20 | 22 | 24 | 218 |
| COOCH3 | Ph | 4-OCH3 | NT | | | 219 |
| CH3 | Ph | 4-OCH3 | NT | | | 220 |
| Ph | Ph | 4-OCH3 | 85.00% | 79 | 18 | 221 |
| Benzoyl | Ph | 4-OCH3 | 24% | 15 | 0 | 222 |
| p-CH3 Benzoyl | Ph | 4-OCH3 | NT | −24 | −28 | 223 |
| Furoyl | Ph | 4-OCH3 | 79% | −24 | 2 | 224 |
| p-Cl Ph | Ph | 4-OCH3 | 80.00% | 47 | 58 | 225 |
| COOC2H5 | CH3 | 2-Cl | NT | | | 226 |
| COOCH3 | CH3 | 2-Cl | NT | | | 227 |
| CH3 | CH3 | 2-Cl | NT | | | 228 |
| Ph | CH3 | 2-Cl | NT | 6 | 21 | 229 |
| p-Cl Ph | CH3 | 2-Cl | 58 | 60 | 21 | 230 |
| COOC2H5 | Ph | 2-Cl | NT | | | 231 |
| COOCH3 | Ph | 2-Cl | NT | 55 | 67 | 232 |
| CH3 | Ph | 2-Cl | NT | | | 233 |
| Ph | Ph | 2-Cl | NT | | | 234 |
| Benzoyl | Ph | 2-Cl | NT | | | 235 |
| p-CH3 Benzoyl | Ph | 2-Cl | NT | | | 236 |
| Furoyl | Ph | 2-Cl | NT | | | 237 |
| p-Cl Ph | Ph | 2-Cl | 61 | | | 238 |
| COOC2H5 | CH3 | 3-Cl | NT | | | 239 |
| COOC2H5 | Ph | 3-Cl | NT | | | 240 |
| COOCH3 | Ph | 3-Cl | NT | | | 241 |
| COOC2H5 | CH3 | 4-Cl | 65% | 53 | 12 | 242 |
| COOCH3 | CH3 | 4-Cl | NT | | | 243 |
| CH3 | CH3 | 4-Cl | 71% | 93 | 82 | 244 |
| Ph | CH3 | 4-Cl | 72 | 79 | 82 | 245 |
| p-Cl Ph | CH3 | 4-Cl | 38% | 96 | 74 | 246 |
| p-CH3 Ph | CH3 | 4-Cl | 71.90% | | | 247 |
| p-OCH3Ph | CH3 | 4-Cl | NT | | | 248 |
| COOC2H5 | Ph | 4-Cl | 81% | 16 | 0 | 249 |
| COOCH3 | Ph | 4-Cl | 83 | 17 | 5 | 250 |
| CH3 | Ph | 4-Cl | 92.00% | 85 | 69 | 251 |
| Ph | Ph | 4-Cl | 81% | 80 | 21 | 252 |
| Benzoyl | Ph | 4-Cl | 83 | 87 | 28 | 253 |
| p-CH3 Benzoyl | Ph | 4-Cl | NT | 0 | 2 | 254 |
| Furoyl | Ph | 4-Cl | NT | 0 | 7 | 255 |
| p-Cl Ph | Ph | 4-Cl | 84% | 99 | 61 | 256 |
| p-CH3 Ph | Ph | 4-Cl | NT | −10 | −51 | 257 |
| p-OCH3Ph | Ph | 4-Cl | NT | | | 258 |
| COOC2H5 | CH3 | 4-COCH3 | 69.17% | | | 259 |
| COOCH3 | CH3 | 4-COCH3 | NT | | | 260 |
| CH3 | CH3 | 4-COCH3 | 42 | 71 | −33 | 261 |
| Ph | CH3 | 4-COCH3 | NT | 15 | 7 | 262 |
| p-Cl Ph | CH3 | 4-COCH3 | 13 | 0 | 2 | 263 |
| COOC2H5 | Ph | 4-COCH3 | 40 | 25 | 25 | 264 |
| COOCH3 | Ph | 4-COCH3 | NT | 0 | 16 | 265 |
| CH3 | Ph | 4-COCH3 | NT | 4 | 15 | 266 |
| Ph | Ph | 4-COCH3 | NT | 43 | 19 | 267 |
| Benzoyl | Ph | 4-COCH3 | NT | 18 | 44 | 268 |
| p-CH3 Benzoyl | Ph | 4-COCH3 | NT | 27 | 1 | 269 |
| Furoyl | Ph | 4-COCH3 | 20 | 11 | 18 | 270 |
| p-Cl Ph | Ph | 4-COCH3 | 23 | −12 | 31 | 271 |

TABLE 9

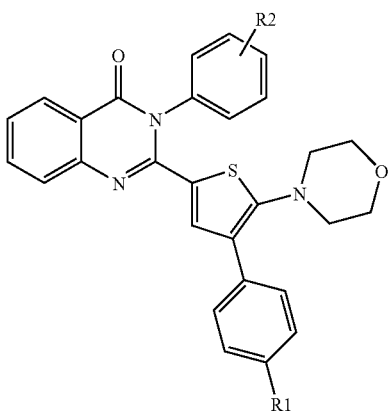

| R1 | R2 | % Protection | NFkB inhibition @ 1 uM | AP-1 inhibition @ 1 uM | Example No |
|---|---|---|---|---|---|
| H | H | 30 | -2 | 11 | 272 |
| Cl | H | 0 | -35 | -17 | 273 |
| NHCOCH3 | H | 28 | 29 | NT | 274 |
| SO2CH3 | H | 25 | 9 | 28 | 275 |
| SCH3 | H | 49 | -10 | -17 | 276 |
| 4-Pyridyl | H | 65 | 30 | 38 | 277 |
| H | 2-CH3 | 37 | NT | NT | 278 |
| Cl | 2-CH3 | 0 | NT | NT | 279 |
| NHCOCH3 | 2-CH3 | NT | | | 280 |
| SO2CH3 | 2-CH3 | 50 | NT | NT | 281 |
| SCH3 | 2-CH3 | NT | | | 282 |
| 4-Pyridyl | 2-CH3 | 51 | 53 | -18 | 282 |
| H | 3-CH3 | NT | | | 284 |
| Cl | 3-CH3 | NT | | | 285 |
| NHCOCH3 | 3-CH3 | 52 | 35 | 13 | 286 |
| SO2CH3 | 3-CH3 | 51 | NT | NT | 287 |
| SCH3 | 3-CH3 | 31 | NT | NT | 288 |
| 4-Pyridyl | 3-CH3 | 30 | 42 | 35 | 289 |
| H | 4-CH3 | 48 | NT | NT | 290 |
| Cl | 4-CH3 | 53 | NT | NT | 291 |
| SO2CH3 | 4-CH3 | 31 | NT | NT | 292 |
| 4-Pyridyl | 4-CH3 | | | | 293 |
| H | 2-OCH3 | 34 | NT | NT | 294 |
| Cl | 2-OCH3 | 52 | NT | NT | 294 |
| NHCOCH3 | 2-OCH3 | NT | | | 296 |
| SO2CH3 | 2-OCH3 | 63 | 55 | 33 | 297 |
| 4-Pyridyl | 2-OCH3 | 42 | 55 | 33 | 298 |
| H | 3-OCH3 | NT | | | 299 |
| SO2CH3 | 3-OCH3 | 48 | 20 | -4 | 300 |
| H | 4-OCH3 | NT | | | 301 |
| Cl | 4-OCH3 | NT | | | 302 |
| SO2CH3 | 4-OCH3 | 53 | 60 | 10 | 303 |
| H | 2-Cl | 37 | NT | NT | 304 |
| Cl | 2-Cl | 40 | NT | NT | 305 |
| NHCOCH3 | 2-Cl | NT | | | 306 |
| SO2CH3 | 2-Cl | 31 | NT | NT | 307 |
| 4-Pyridyl | 2-Cl | 43 | 80 | 35 | 308 |
| H | 4-Cl | 66 | 0 | 2 | 309 |
| Cl | 4-Cl | 60 | 0 | 14 | 310 |
| NHCOCH3 | 4-Cl | 28 | 0 | 17 | 311 |
| SO2CH3 | 4-Cl | 57 | 0 | 7 | 312 |
| 4-Pyridyl | 4-Cl | 52 | 68 | 32 | 313 |
| H | 4-COCH3 | 36 | 0 | 25 | 314 |
| Cl | 4-COCH3 | 51 | 0 | 7 | 315 |
| NHCOCH3 | 4-COCH3 | NT | | | 316 |
| SO2CH3 | 4-COCH3 | 73 | 46 | 31 | 317 |
| 4-Pyridyl | 4-COCH3 | 81 | 66 | 84 | 319 |

TABLE 10

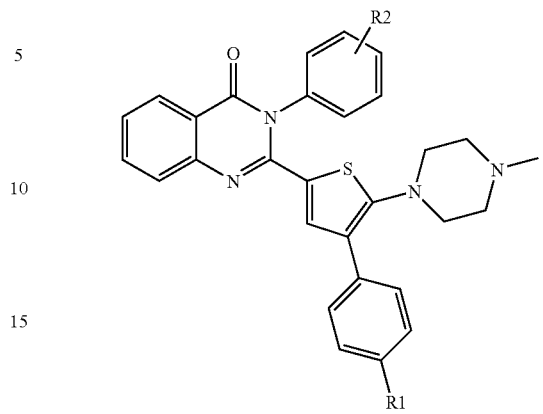

| R1 | R2 | % Protection | NFkB inhibition @ 1 uM | AP-1 inhibition @ 1 uM | Example No. |
|---|---|---|---|---|---|
| SO2CH3 | 4-Cl | 21 | NT | NT | 318 |

Example 397

Anti-Inflammatory Activity

Sprague-Dawley rats, male and female, 150-250 g will be used in an edema test. Rats will be deprived of food but not water for 18 hours prior to the experiment. The test compounds will be administered with a blunt-tipped needle orally, 50 mg/kg, as a suspension in 0.1% sodium CMC (carboxymethylcellulose) vehicle. Alternatively, the test compounds will be injected intravenously, subcutaneously, or intraperitoneally. One hour later, 0.1 ml of a 1% carrageenan solution in saline will be injected in the sub-plantar region of the right hind paw of each rat. Five minutes after the administration of carrageenan, displacement in a mercury-filled plethysmometer will be observed by dipping the treated paw up to a pre-marked line on ankle. The reading will be repeated 3 hours later. The displacement readings give a measure of carageenan-induced edema. Any reduction in carageenan-induced edema with a test compound, as compared to saline control, is a measure of the anti-inflammatory activity of the test compound. The percentage protection at 50-mg/kg doses was calculated according to the following formula: % Protection=[(Control−Test)/Control]×100%.

Example 398

Development and Results of Screening Assays (eIF4E, ARE, NF-κB and AP-1)

Development of eIF4E Screen: The focus of this assay is to identify compounds capable of inhibiting highly cap-dependent translation, without affecting normal cap-dependent translation. Since highly cap-dependent translation is associated with synthesis of proteins involved in cancer, a compound that inhibits this pathway may be used as an anti-cancer agent. The assay was developed by cloning the highly structured 5' UTR of FGF, which requires high levels of eIF4E before protein synthesis can initiate, into the proper orientation of the reporter gene luciferase, and then stably transfecting the modified luciferase gene into the cell line FaDu that is known to have high levels of eIF4E. The activity of luciferase is then monitored in the presence and absence of the tested compound.

Generation of Stable Cell Lines: The pMS110 plasmid (pGL3-control plasmid from Promega which contains a neo selectable marker) was used to generate pMS110-5'UTR by cloning the 5' UTR of FGF just upstream of the luciferase AUG start codon. FaDu cells, a head and neck cancer cell line, were transfected using Lipofectamine2000 (Invitrogen). Twenty-four hours after transfection G418 was added at 500 µg/ml. Cells were maintained in G418 for 14 days, and then individual colonies were transferred to a 96-well plate for propagation. Individual clones were analyzed for luciferase expression by plating $10^4$ cells per well in a 96-well plate for 24 hours before lysing the cells and analyzing for luciferase activity in a Victor 111 (Perkin Elmer) or Lucy2 (Rosys Anthos). FaDu9000 and FaDuUTR were the clones that expressed the highest level of active luciferase following transfection of pMS110 and pMS110-5'UTR, respectively.

Analysis of Rapamycin Responsiveness: Cells of FaDu9000 and FaDuUTR were plated at $1 \times 10^4$ cells/well in a 96-well dish. Twenty-four hours after plating, 0.1% DMSO (vehicle control) or 10 nM rapamycin were added to each well, and the cells were maintained for an additional 24 or 48 hours. The cells were then lysed and luciferase activity was determined using BriteGlo (Promega) as per manufacturer's instruction and recorded using the Victor III. Following subtraction of background activity, the mean value of quadruplicate samples for a given experiment was determined, and the treated cells were normalized to the control. At least four separate experiments were conducted, and the mean and standard error were calculated. To determine if rapamycin affected cell viability, an MTS assay (Cell Proliferation One Solution, Promega) was carried out on each population at 48 hours in two separate experiments.

Development of ARE Screen: The regulation of TNF-α and other cytokines that are involved in inflammation and cancer progression occurs, in part, at the post-transcriptional level through an AU-rich element in the 3' UTR called ARE. The ARE regulates both the stability and the translational efficiency of the mRNA and thus represents a potential target for novel anti-inflammatory molecules. The 3' UTR from TNF-α, which contains the ARE, was cloned in the proper orientation and used to screen a compound library as reported in reference 55. Briefly, the 3' UTR was cloned into pMS110, and both the UTR and parental plasmids were stably transfected into RAW264.7 cells, a macrophage cell line. Individual clones were propagated and tested for luciferase activity. Clones with and without the UTR that demonstrated similar levels of luciferase activity were recovered and used for compound screening. The UTR-containing clones responded to LPS by inducing luciferase expression similar to the endogenous increase in TNF-α following LPS stimulation. Compounds that decreased luciferase expression in the UTR-containing construct but did not affect luciferase expression of the control construct are useful as anti-inflammatory agents. Thus, molecules identified with this screening assay are also useful as anti-cancer agents. By analogy, thalidomide, which has been reported to work in part through posttranscriptional regulation of TNF-α, has been approved for the treatment of multiple myeloma and is now in development for the treatment of cancers.

Development of NF-κB and AP-1 Screens: Two HEK293 cell lines were purchased from Panomics. One cell line was stably transfected with a plasmid in which luciferase expression is regulated by six copies of the NF-κB transcriptional element (5'-AGTTGAGGGGACTTTCCCAGGC-3'); and the other cell line was stably transfected with a plasmid in which luciferase expression is regulated by three copies of the AP-1 transcriptional element (TGACTAA). To test the biological activity of the promoters, the HEK/NF-κB cell line was stimulated with TNF-α (20 ng/ml) for 24 hours, and the HEK/AP-1 cell line was stimulated with PMA (10 ng/ml) for 24 hours. Both cell lines increased luciferase activity after stimulation: stimulation with NF-κB increased luciferase expression by 100-fold, and stimulation with AP-1 increase luciferase expression by 30-fold. In addition, a pyrimidine carboxylmide that had previously been shown (ref. 58) to be an inhibitor of transcription mediated by NF-κB and AP-1 reduced luciferase activity by approximately 40% in each of the NF-κB and AP-1 cell lines.

Thirty-nine representative compounds have been screened through the four screens (eIF4E, ARE, NF-κB and AP-1) to identify multi-pathway inhibitors. These 39 compounds were:

| Compound # | Compound Designation | Example # of Compound Description |
|---|---|---|
| 1 | PMCR111 | Example 224 |
| 2 | PMCR112 | Example 225 |
| 3 | PMCR145 | Example 242 |
| 4 | PMCR147 | Example 244 |
| 5 | PMCR148 | Example 245 |
| 6 | PMCR152 | Example 246 |
| 7 | PMCR153 | Example 249 |
| 8 | PMCR155 | Example 251 |
| 9 | PMCR156 | Example 252 |
| 10 | PMCR157 | Example 253 |
| 11 | PMCR9 | Example 159 |
| 12 | PMCR11 | Example 320 |
| 13 | PMCR12 | Example 161 |
| 14 | PMCR13 | Example 162 |
| 15 | PMCR16 | Example 165 |
| 16 | PMCR105 | Example 218 |
| 17 | PMCR108 | Example 221 |
| 18 | PMCR109 | Example 222 |
| 19 | PMCH18 | Example 135 |
| 20 | PMCH19 | Example 136 |
| 21 | $PMCH_20$ | Example 113 |
| 22 | $PMCH_21$ | Example 112 |
| 23 | $PMCH_22$ | Example 114 |
| 24 | $PMCH_23$ | Example 115 |
| 25 | $PMCH_24$ | Example 116 |
| 26 | $PMCH_25$ | Example 46 |
| 27 | $PMCH_26$ | Example 105 |
| 28 | $PMCH_27$ | Example 116 |
| 29 | PMCH4 | Example 123 |
| 30 | PMCH8 | Example 126 |
| 31 | PMCH9 | Example 127 |
| 32 | PMCH13 | Example 132 |
| 33 | PMCH14 | Example 139 |
| 34 | PMCH15 | Example 138 |
| 35 | PMCH16 | Example 134 |
| 36 | PMCH17 | Example 133 |
| 37 | PMCR14 | Example 163 |
| 38 | PMCR159 | Example 255 |
| 39 | PMCR160 | Example 256 | eIF4E Assay Development

Following transfection and selection with G418, individual clones were transferred to 96-well plates and propagated, before testing for luciferase activity. A total of 118 individual clones were analyzed for luciferase activity, 87 with a pMS110 plasmid lacking a structured FGF 5'UTR, and 31 with a plasmid containing the 5' UTR of FGF. For both clone types, almost 50% of the clones did not demonstrate any luciferase activity. Of those clones that did express luciferase, the clones without the FGF 5' UTR had higher luciferase activity than did the clones containing the FGF 5'UTR (FIG.

Figure 6:
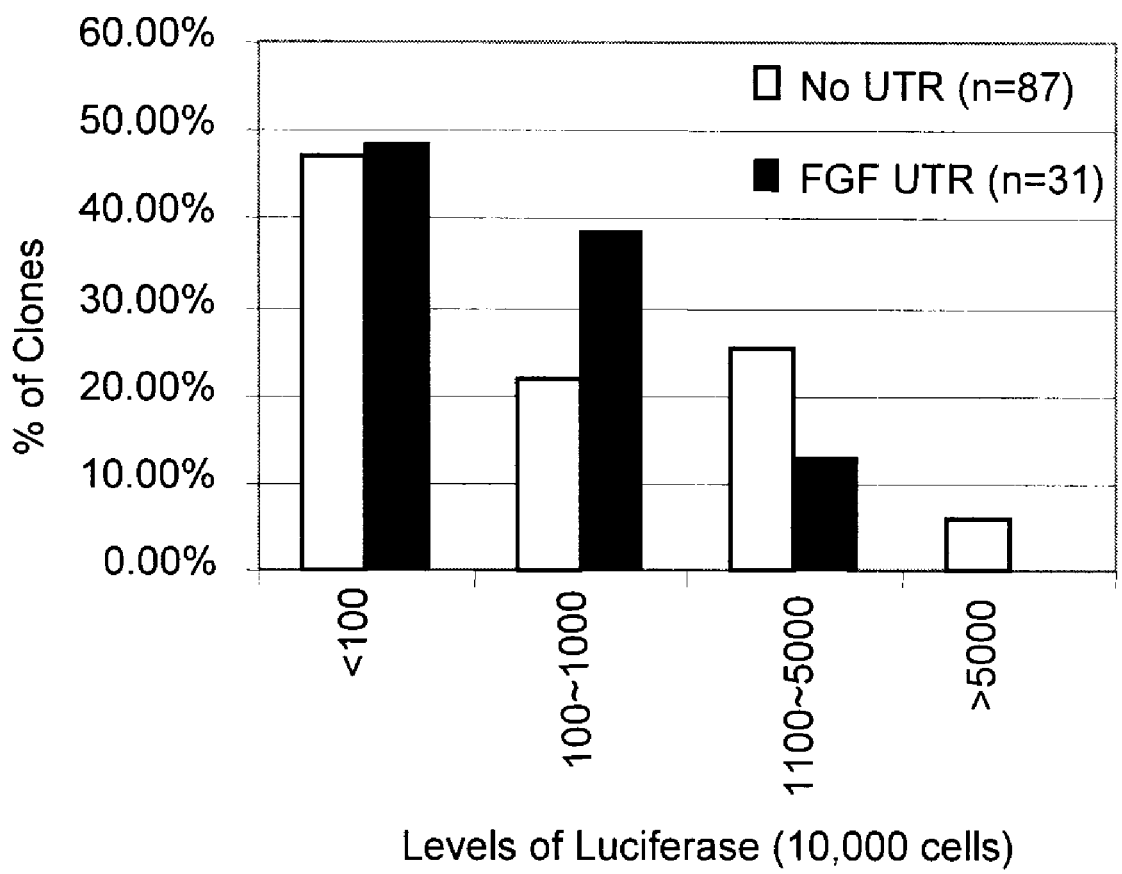
FIG. 6 illustrates the percent of individual clones of FaDu cells stably transfected with the FGF 5'UTR or without the UTR that express luciferase activity in one of four groups (<100 units, 100-1000 units, 1100-5000 units, and >5000 units).

6). In FIG. 6, luciferase activity was tested using a Victor II luminometer. Expression levels of luciferase were placed into four groups: no expression (<100 units), low expression (100-1000 units), mid expression (1100-5000 units), and high expression (>5000 units). The percentages of clones from each transfection (with and without UTR) that fell into each of the four groups is shown in FIG. 6. A similar depression of luciferase activity was noted when two sets of independently transfected populations were analyzed (data not shown). These results demonstrated that while the 5' UTR of FGF somewhat inhibited luciferase expression, FaDu cells transfected with the FGF 5'UTR were capable of translating the luciferase RNA, consistent with high levels of intracellular eIF4E.

Figure 7:
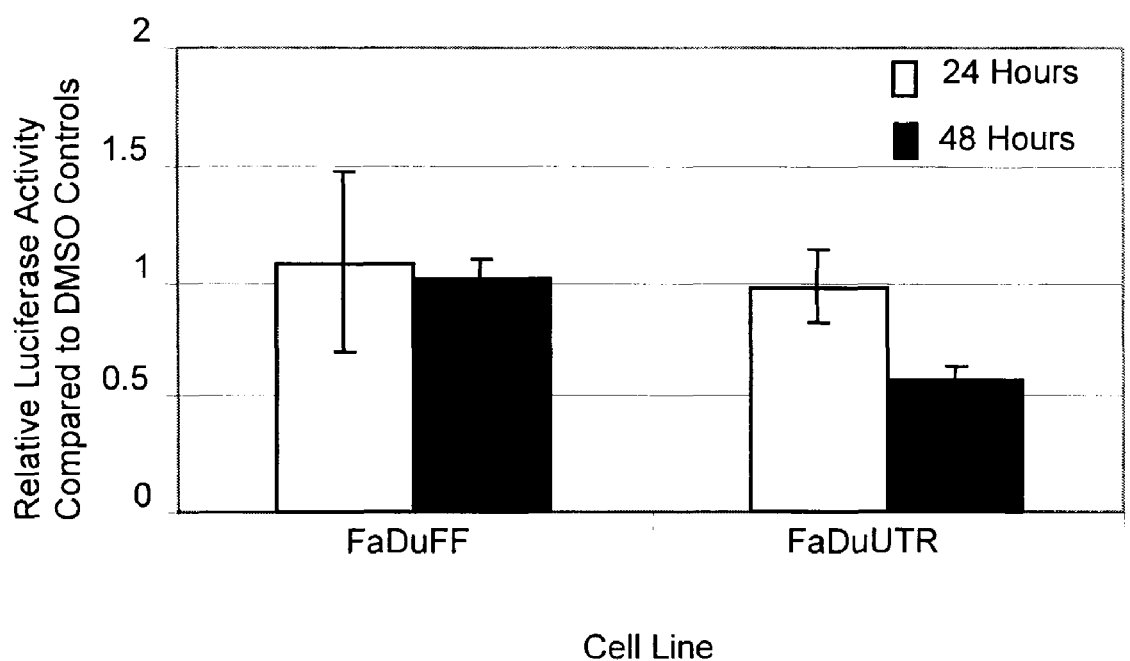
FIG. 7 illustrates the effect of 10 nM rapamycin on luciferase expression as measured from FaDu cells stably transfected with the FGF 5'UTR (FaDu UTR) or without the UTR (FaDu FF).

Rapamycin, a well-established inhibitor of eIF4E, was tested for its ability to inhibit luciferase expression in the transfected FaDu cells. Rapamycin would be expected to preferentially inhibit the FaDu cells expressing luciferase under the control of the FGF 5' UTR, since lowering levels of eIF4E would affect those transcripts containing highly structured UTRs, thus affecting highly cap-dependent translation. Although 24 hr treatment did not decrease expression in either cell line, after 48 hr luciferase expression decreased significantly ($p<0.001$) in the FaDu cells containing the plasmid with the FGF UTR (FIG. 7). In FIG. 7, FaDu cells transfected with the luciferase reporter gene with the 5'UTR of FGF (FaDu UTR) or without this UTR (FaDu FF) were plated at 50% confluence. After 24 hr, the cells were treated with either 10 nM rapamycin or vehicle (DMSO). Luciferase activity was then measured as above, and the activity was normalized versus the vehicle-treated cells.

eIF4E Inhibitor Screen

Figure 8:
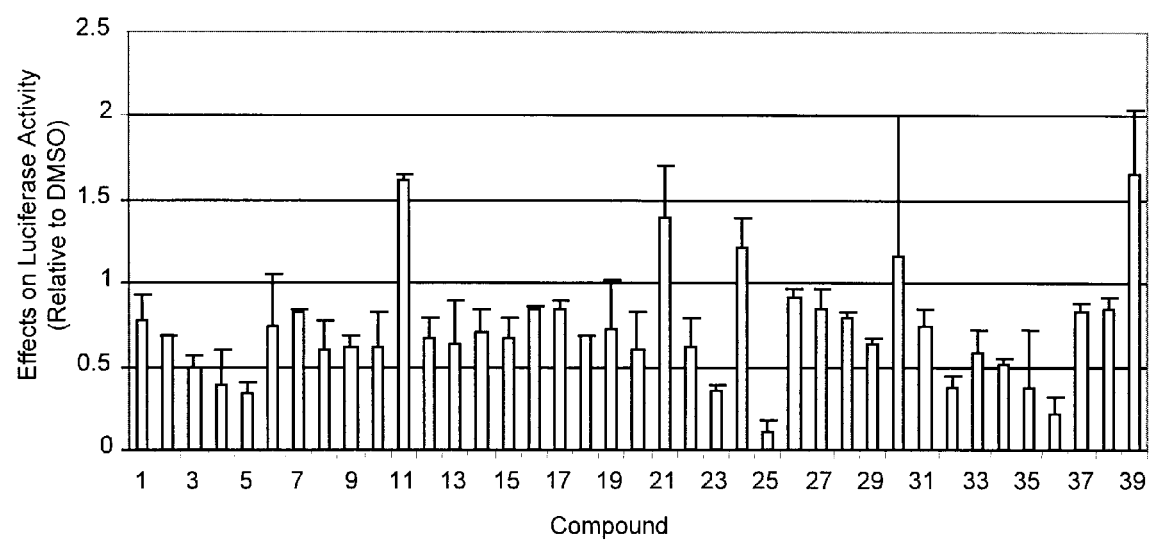
FIG. 8 illustrates the effect of 1 μM of each of 39 compounds dissolved in DMSO (0.3%) on luciferase expression as measured from FaDu cells stably transfected with the FGF 5'UTR (FaDu UTR) with values normalized to that of a DMSO control. Each bar represents the average and standard deviation of two experiments, each experiment testing each compound in triplicate.

The FaDu cell line stably transfected with FGF 5'UTR was used to screen thirty-nine representative compounds, each at a concentration of 1.0 µM. Additional cells were treated with vehicle, 0.3% DMSO. Cells were plated for twenty-four hours in a 96-well plate. Each compound was then added to triplicate wells, and the cells were incubated for forty-eight hours before measuring luciferase activity as above. The mean luciferase activity was measured using Promega's Brite-Glo kit, and the mean for each sample was normalized to DMSO. The experiment was then repeated, and the average and standard deviation of the two experiments were determined (FIG. 8).

Figure 9:
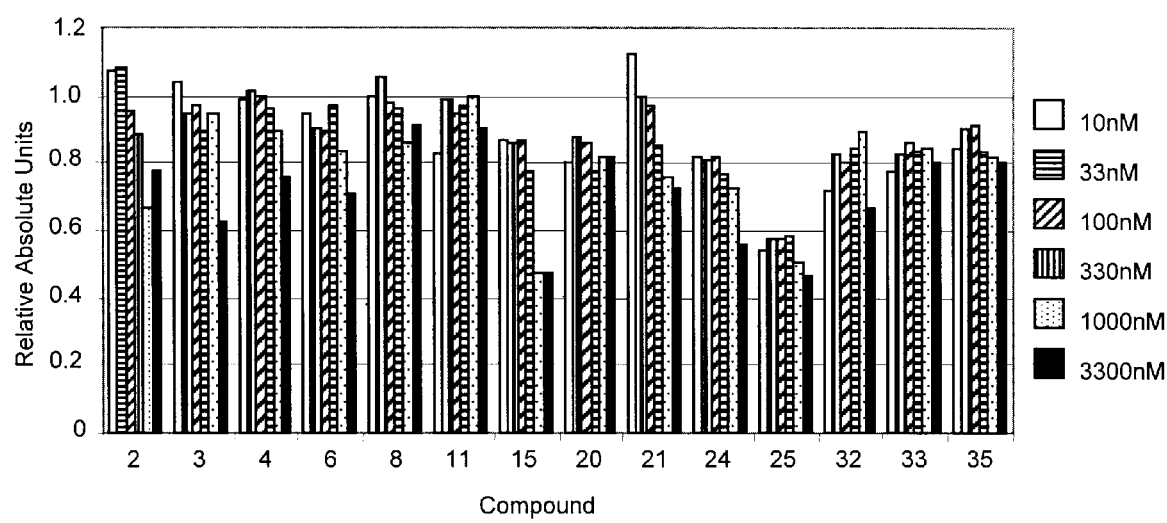
FIG. 9 illustrates the effect of 14 selected compounds tested at each of six concentrations dissolved in DMSO (0.3%) on FaDu cell viability using an MTT assay with values normalized to that of a DMSO control. Each bar represents the result of one experiment.

A number of the compounds inhibited luciferase expression under the control of the FGF 5'UTR (notably, compounds numbered 4, 5, 23, 25, 35, and 36), and a few compounds actually increased luciferase expression (Compounds numbered 11, 21, 24, 30, and 39) (Compound numbers as indicated in table 11, column 1. Values greater than 1.0 indicate activation, and values less than 1.0 indicate inhibition.) The compounds that inhibited luciferase translation might, potentially, act by generally inhibiting translation, by reducing cell numbers through inhibition of growth or by cell toxicity, or specifically by inhibiting highly cap-dependent translation. To analyze any general effects on cell viability, fourteen compounds were selected that altered luciferase activity (including a few that increased activity) to test for any effects on cell number. An MTT assay was used to monitor compounds for inhibition of cell growth and cell toxicity. The compounds were tested once in a six-point dose-response assay starting at 10 nM and increasing to 3.3 µM. FaDu cells were plated in a 96-well plate for 24 hr before addition of the compounds. Each compound was added in each of six concentrations (10 nM, 30 nM, 100 nM, 330 nM, 1000 nM, and 3300 nM), and each concentration was tested in triplicate. In addition, DMSO was used as a control. After incubating for 24 hr, the cell number was measured using the MTT assay. FIG. 9 shows the results of the 14 compounds at each of the indicated concentrations after normalizing the results to the DMSO control.

Compound 35 strongly inhibited luciferase activity (>60% inhibition) without affecting cell viability (~20% inhibition) at the highest concentration tested. Compound 25 was also interesting. Although it inhibited cell numbers at each concentration tested, it had the most pronounced effect on luciferase activity, inhibiting it by greater than 90% at the highest concentration tested, 10 µM. Other compounds, such as Compound 3, inhibited luciferase activity at 1 µM and cell growth at nearly the same concentration (3.3 µM). While this inhibition of eIF4E-induced luciferase expression may simply be due to fewer cells, it is also possible that the inhibition leads to reduced cell number. It seems more likely that the remaining cells would also have lower levels of expression, suggesting that compounds 35 and 27 would be of greater interest for identification of specific eIF4E inhibitors.

ARE Screen

Figure 10:
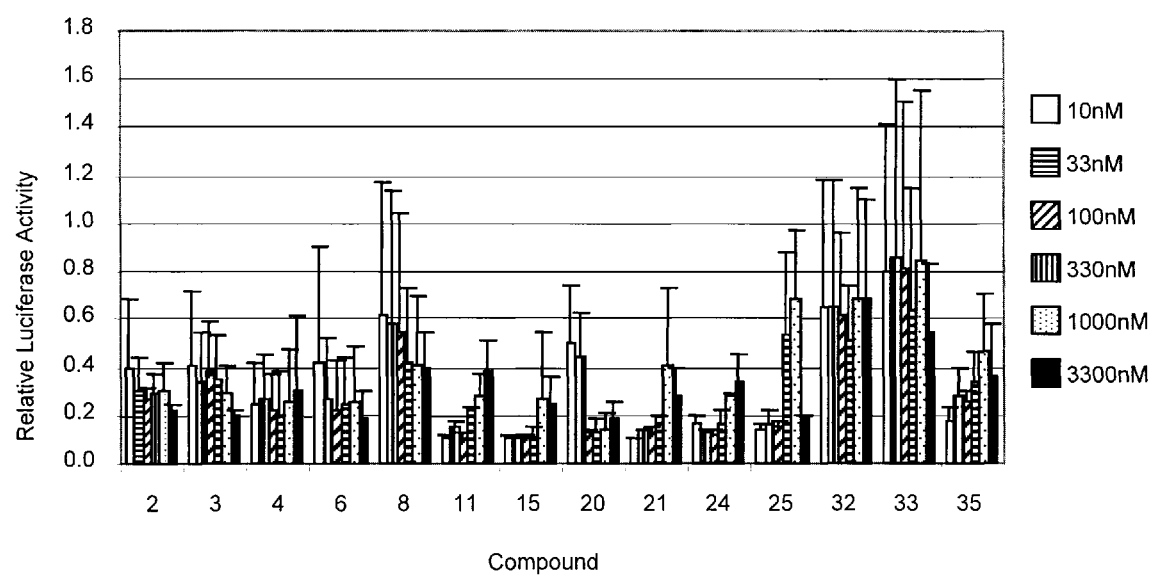
FIG. 10 illustrates the effect of 1 μM of each of 14 selected compounds tested at each of six concentrations dissolved in DMSO (0.3%) on luciferase expression as measured from RAW 264.7 cells stably transfected with a vector expressing luciferase under the post-transcriptional control of the ARE from TNF-α with values normalized to that of the average expression level at the lowest tested concentration. Each bar represents the average and standard deviation of testing each compound in triplicate.

The same fourteen compounds (those numbered 2, 3, 4, 6, 8, 11, 15, 20, 21, 24, 25, 32, 33, and 35) were tested for dose-response in an assay that measured inhibition of luciferase expression under control of an ARE. As in the eIF4E assay, AREs are responsible for post-transcriptional regulation of gene expression, influencing both translation and mRNA stability. Raw 254.7 cells stably transfected with a vector expressing luciferase under the post-transcriptional control of the ARE from TNF-α were plated in a 96-well plate. After 24 hr, each compound was added in triplicate for each of six concentrations (10 nM, 33 nM, 100 nM, 330 nM, 1000 nM, and 3300 nM). After 24 hr incubation, the cells were lysed and a luciferase assay was conducted. The results were normalized to DMSO by the average expression level at the lowest concentration tested. (On the first run, 3% DMSO instead of 0.3% was used as a control, and the cells died. The average luciferase units from all the compounds tested at 10 nM in experiment 1 was 0.568, and in experiment 2 was 0.561. Thus, since we did not have a true DMSO control for experiment 1, we normalized to the average value of the lowest concentration for each experiment. The actual luciferase level in experiment 2 was 1.897. Because the two averages at 10 nM were essentially identical, the actual inhibition was greater than what it may appear.) The results are shown in FIG. 10.

Almost all of the fourteen compounds inhibited luciferase expression in the presence of ARE. Compounds 2 and 3 were the only two that indicated a substantial dose response. The strength of the inhibition, in many cases ≧80% at 3.3 µM, was impressive, and indicated that these compounds are potent anti-inflammatory agents.

NF-κB Inhibitor Screen

Figure 11:
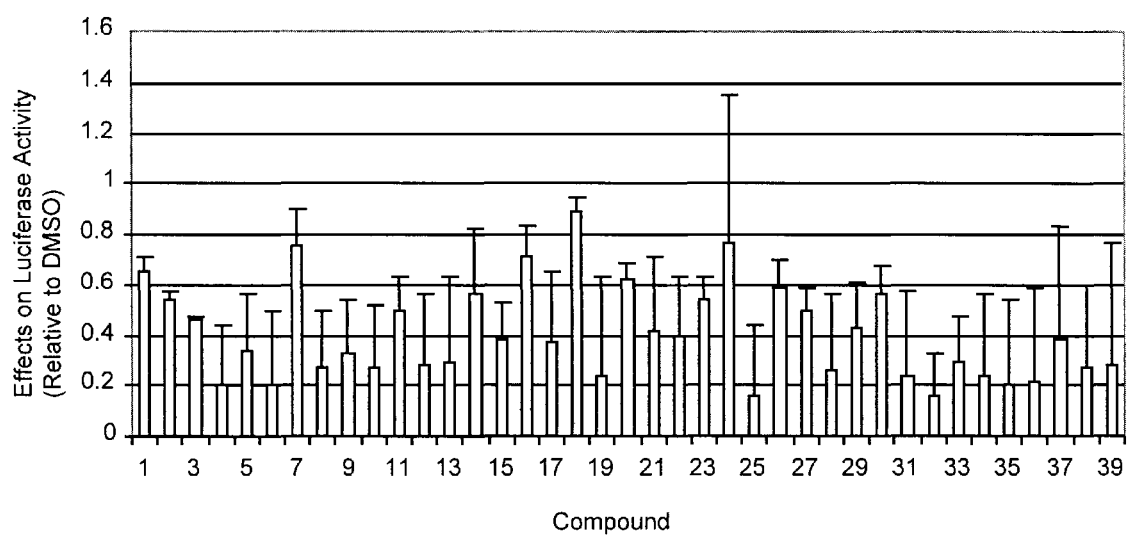
FIG. 11 illustrates the effect of 1 μM of each of 39 compounds dissolved in DMSO (0.3%) on luciferase expression as measured from HEK cells stably transfected with a plasmid expressing luciferase under the control of the NF-κB promoter with values normalized to that of a DMSO control. Each bar represents the average and standard deviation of two experiments, each experiment testing each compound in triplicate.

The above two assays analyzed the effects of the compounds on post-transcriptional gene regulation, which is known to play a key role in cancer and inflammation. By contrast, the NF-κB assay and the following assay (AP-1) test whether the compounds act at the transcriptional level. Thirty-nine representative compounds were screened in an HEK/NF-κB cell line. HEK cells were stably transfected with a plasmid expressing luciferase under the control of the NF-κB promoter. These transfected cells were plated on a 96-well plate. As above, initial screening was carried out at 1.0 µM by adding compound in DMSO (0.3%) twenty-four hours after plating. Each compound was added to each of triplicate wells. DMSO (0.3%) was added to one set of wells as a control. Luciferase activity was determined using Promega's Brite-Glo kit, and the mean for each sample was normalized to that for DMSO. The experiment was repeated, and the average and standard deviation of the two experiments are shown in FIG. 11.

Most of the compounds inhibited NF-κB-dependent luciferase expression, indicating anti-inflammatory activity. One compound (compound 24) actually potentiated expression in one of the two experiments.

The fourteen representative compounds identified in the eIF4E screen as interesting (Numbered 2, 3, 4, 6, 8, 11, 15, 20, 21, 24, 25, 32, 33, and 35) were then tested for luciferase activity in a six-point dose response (10 nM, 33 nM, 100 nM, 330 nM, 1000 nM, and 3300 nM). Screening was carried out as described above by monitoring the effects of the compounds on basal NF-κB-dependent luciferase expression. Each dose was used out in triplicate, and repeated between two and four times. Results were normalized by the average expression level at the lowest concentration level, as described above. The mean and standard deviation of the averages from each replicate are presented in FIG. 12.

Figure 12:
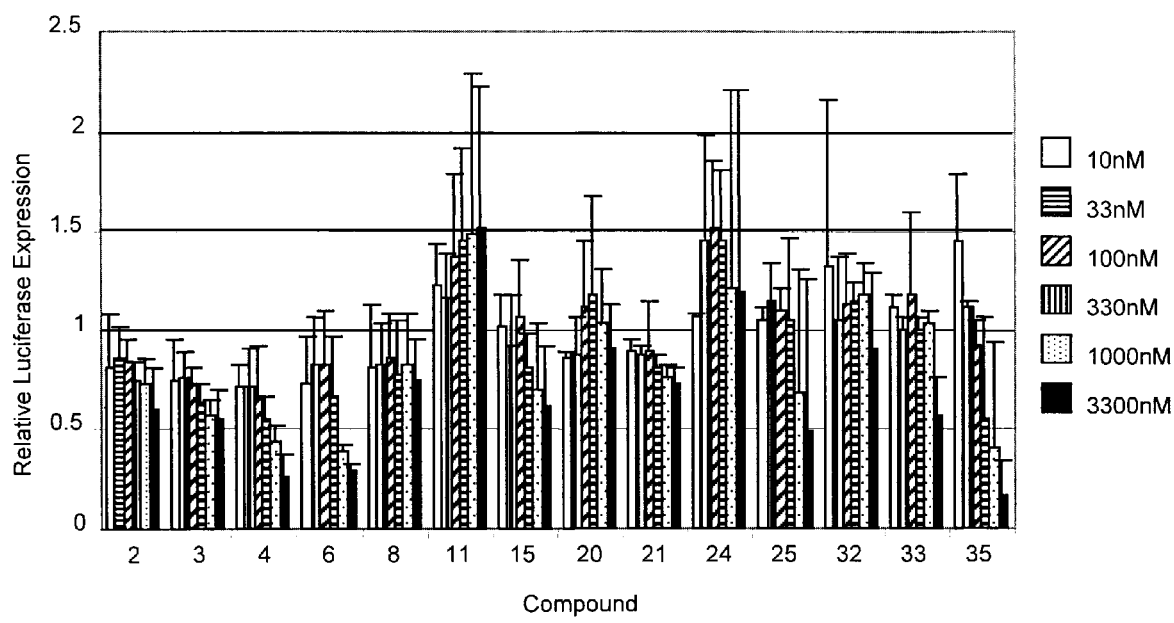
FIG. 12 illustrates the effect of 14 selected compounds tested at six concentrations dissolved in DMSO (0.3%) on luciferase expression as measured from HEK cells stably transfected with a plasmid expressing luciferase under the control of the NF-κB promoter with values normalized to that of the average expression level at the lowest tested concentration. Each bar represents the average and standard deviation of testing each compound in triplicate.

As shown in FIG. 12, five compounds (numbered 3, 4, 6, 25 and 35) inhibited NF-κB-dependent luciferase expression by about 50% at 3.3 µM. As shown above, at this concentration, all but Compound 35 inhibited the growth/viability of the FaDu cancer cell line. Each of the five compounds also demonstrated a substantial dose-response over the concentrations tested. Four of the five compounds (3, 4, 6 and 35) had substantial activity at submicromolar concentrations. As NF-κB activation has been demonstrated to play a role in cancer, in addition to its well understood role in inflammation, these inhibitors will be useful as anti-cancer agents.

AP-1 Inhibitor Screen

Figure 13:
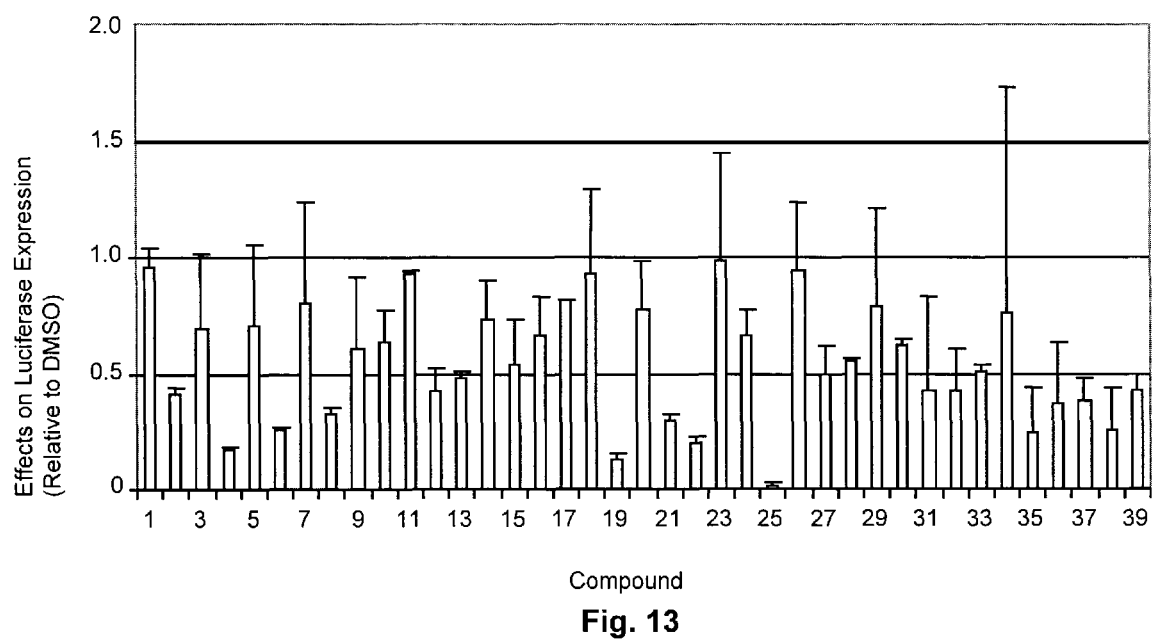
FIG. 13 illustrates the effect of 1 μM of each of 39 compounds dissolved in DMSO (0.3%) on luciferase expression as measured from HEK cells stably transfected with a plasmid expressing luciferase under the control of the AP-1 promoter with values normalized to that of a DMSO control. Each bar represents the average and standard deviation of two experiments, each experiment testing each compound in triplicate.

Since inflammation and cancer have also been linked to AP-1 promoter activation, the thirty nine representative compounds were also screened for inhibition in an HEK/AP-1 cell line. HEK cells were stably transfected with a plasmid expressing luciferase under the control of the AP-1 promoter. The transfected cells were plated on a 96-well plate for 24 hr. Then 1.0 µM of each compound in DMSO (0.3%) was added to triplicate wells and incubated for 48 hr. DMSO (0.3%) was added to one set of triplicate wells as a control. Luciferase activity was determined using Promega's Brite-Glo kit, and the mean for each sample was normalized to that for DMSO. The experiment was repeated, and the average and standard deviation of the two experiments are shown in FIG. 13.

As seen above using the NF-κB screen, many of these compounds inhibited AP-1-dependent luciferase expression, although fewer demonstrated the robust inhibition observed in the NF-κB screen. In the AP-1 screen, about 50% of the compounds inhibited activity by about 50%, compared with about 75% of the compounds in the NF-κB screen. Interestingly, Compound 25 showed almost complete inhibition of activity in both AP-1 replicates.

The fourteen representative compounds identified in the eIF4E screen as interesting (Numbered 2, 3, 4, 6, 8, 11, 15, 20, 21, 24, 25, 32, 33, and 35) were then tested for luciferase activity in a six-point dose response (10 nM, 33 nM, 100 nM, 330 nM, 1000 nM, and 3300 nM). Screening was carried out as described above, monitoring the compounds' effects on basal AP-1-dependent luciferase expression. Each dose-response experiment was carried out in triplicate and repeated between two and four times. The mean and standard deviation of the averages from each replicate are presented in FIG. 9.

Figure 14:
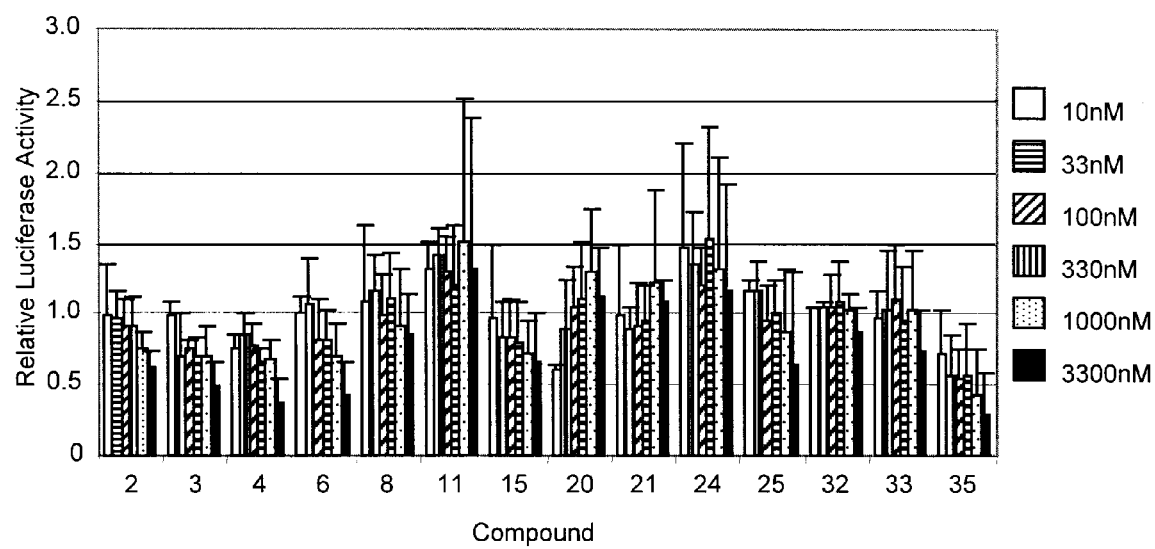
FIG. 14 illustrates the effect of 14 selected compounds tested at six concentrations dissolved in DMSO (0.3%) on luciferase expression as measured from HEK cells stably transfected with a plasmid expressing luciferase under the control of the AP-1 promoter with values normalized to that of the average expression level at the lowest tested concentration. Each bar represents the average and standard deviation of testing each compound in triplicate.

As shown in FIG. 14, compounds 2, 3, 4, 6, 15, 25 and 35 all inhibited AP-1-dependent luciferase expression by about 50% or greater at 3.3 µM. As with the NF-κB inhibitors, at this concentration, all but Compound 35 inhibited the growth/viability of the FaDu cancer cell line. Each of the five compounds also demonstrated a substantial dose-response over the concentrations tested. Five of the seven compounds (3, 4, 6, 15 and 35) had substantial activity at submicromolar concentrations. As AP-1 activation has been demonstrated to play a role in cancer, in addition to its well understood role in inflammation, these inhibitors will have activity as anti-cancer agents.

Selected Compound Effects on NF-κB Induction

The above screening for transcriptional inhibition of luciferase expression was carried out in non-induced cell lines to determine the effects of compound on basal gene expression. However, in some cancer cases, these transcriptional factors may induce transcription. To analyze the effects of selected compounds on TNF-α induced NF-κB dependent luciferase expression, HEK cells were stably transfected with a plasmid expressing luciferase under the control of NF-κB, and were plated in a 96-well plate for 24 hr. Four of the compounds (numbered 3, 4, 25, and 35) that demonstrated robust inhibition in the dose-response assay above were added at six different concentrations (10 nM, 33 nM, 100 nM, 330 nM, 1000 nM, and 3300 nM). After 2 hr incubation, 20 ng/ml TNF-α was added to each well to induce NF-κB dependent gene transcription. After 24 hr, the cells were lysed and the luciferase assay was conducted as described above. The experiment was repeated. The results were normalized by the average expression level at the lowest concentration tested, and are shown in FIG. 15.

Figure 15:
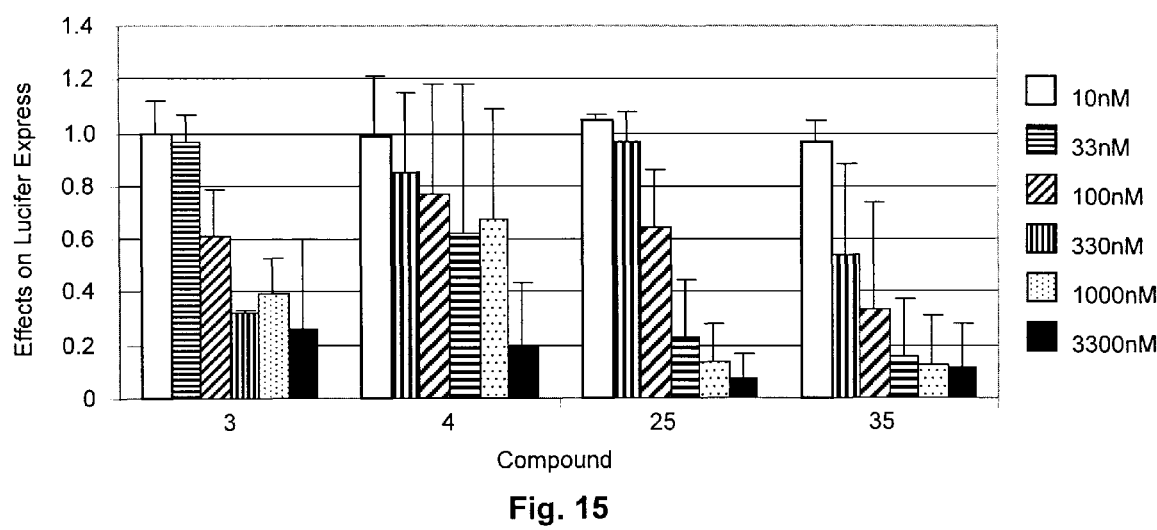
FIG. 15 illustrates the effect of 4 selected compounds tested at six concentrations dissolved in DMSO (0.3%) on TNF-α-induced luciferase expression as measured from HEK cells stably transfected with a plasmid expressing luciferase under the control of the NF-κB promoter with values normalized to that of the average expression level at the lowest tested concentration. Each bar represents the average and standard deviation of two experiments, each experiment testing each compound in triplicate.

As seen in FIG. 15, all four of the compounds strongly inhibited (>70%) TNF-α induced NF-κB gene expression at 3.3 µM concentration. One of the compounds, Compound 35 had an $IC_{50}$ of less than 100 nM, with each of the other three at sub-µM activities. These compounds have activity as anti-cancer and anti-inflammatory agents.

All four of the compounds shown in FIG. 15 showed inhibitory effects in all the screens—indicating an ability to inhibit multiple pathways involved in cancer and inflammation. All compounds tested (39 total) showed some inhibition in at least one of the assays, indicating inhibition of at least one pathway involved in cancer and inflammation.

Additional compounds have also been tested for their ability to inhibit both TNF-α-induced NF-κB expression and PMA-induced AP-1 expression. In both tests, the compound was added for 1 h, then the appropriate inducer was added, and luciferase activity was monitored 24 h later. Values were then normalized to the vehicle control, DMSO. Following the initial luciferase screens, studies were conducted to assess the cytotoxicity of the compounds in normal cells such as VSMC, HUVEC, or HPT cells. Human umbilical vein endothelial cells (HUVEC) represent the normal endothelium, vascular smooth muscle cells (VSMC) were represented by cells from the adult rat aorta, and human proximal tubule (HPT) cells represent the normal proximal tubule in vivo. These cells were grown to near confluency in multi-well plates, and were then treated for 48 h with either vehicle (0.1% DMSO) or 10 µM of each drug candidate. Following treatment, the media from the VSMC and HUVEC incubations were removed, and the amount of lactate dehydrogenase (LDH) released into the medium was determined with a commercial kit. LDH is normally confined to the cytosol, and its release represents "leakiness" of the plasma membrane. LDH activity was expressed as % increase over vehicle-treated cells.

In another assay of viability, the treated VSMC and HUVEC were removed by trypsinization and treated with trypan blue, a dye that is taken up only by dead cells. The number of both live and dead cells was counted using an automated cell viability analyzer. The % decrease in numbers of viable cells was determined. Toxicity in the treated HPT cells was determined by the ethidium homodimer (EthHD) uptake assay. EthHD is a fluorescent dye that is excluded from live cells, but is taken up by cells that have lost permeability barriers. Inside the cell, EthHD produces a strong fluorescent signal, which is proportional to the number of dead cells. Results were expressed as a % increase in cell death over vehicle-treated cells. The lead compounds were also tested in two pairs of cell lines from either the skin or prostate, one tumorigenic and one non-tumorigenic, to test for any differences in toxicity or heightened sensitivity in the tumorigenic lines. The cells were treated for 48 h with vehicle (0.1% DMSO) or 10 μM of each drug candidate. Following treatment, the viability of the cells was determined by the MTT assay. In this assay, the MTT dye is converted only in viable cells by intracellular enzymes to a calorimetric product that is quantitated by a microplate reader. Results are presented in the Table 12.

homodimer fluorescence, relative to vehicle control cells for each compound are marked as #. The $IC_{50}$ concentration, designated by * for the four lead compounds, was determined for AP-1 or NF-κB activity from 6 point dose-response curves.

From these results, four lead compounds were chosen from the 18 compounds that had been screened (Table 13). All four compounds were inhibitors of AP-1, NF-κB, or both. Three compounds showed a lack of toxicity in one or more of the normal cells, or were selectively toxic to cancer cells in culture. PCMR242 was selected differently in that it was a dual inhibitor and also strongly inhibited inflammation in the in vivo assay. In contrast to the other three compounds, it showed significant toxicity in normal cells, but it was included as a lead compound to check the validity of the battery of safety assays.

For the results in Table 13, cells were grown to near confluency in multi-well plates, then treated for 48 h with either vehicle (0.1% DMSO) or 10 μM of each drug candidate. Following treatment, the media from the VSMC and HUVEC incubations were removed, and the amount of lactate dehydrogenase (LDH) released into the medium was determined with a commercial kit and expressed as a % increase over vehicle-treated cells. HPT toxicity was determined by the ethidium homodimer (EthHD) uptake assay. Inside the cell, EthHD produces a strong fluorescent signal, which is propor-

TABLE 12

Compound Charcterization Data

| | | Functional Assays | | Toxicity Assays (Normal Cell Lines) | | | | Cell Death | Viability | Viability (MTT) |
|---|---|---|---|---|---|---|---|---|---|---|
| Example No. | Compound | NF-κB % inhibition | AP-1 % inhibition | Viable Cells % Decrease VSMC | Viable Cells % Decrease HUVEC | LDH release % Increase VSMC | LDH release % Increase HUVEC | (EthHD) % Increase HPT | (MTT) % Decrease HaCaT | % Decrease SRB12-p9 |
| | Vehicle | 100 | 100 | 0 | 0 | 0 | 0 | −10 | 0 | 0 |
| Example 164 | PMCR15 | 2 | 53** | 4 | 7 | 2 | 4 | 101# | 7 | 18 |
| Example 168 | PMCR19 | 18 | 67** | 29# | 20 | 4 | 14 | 63# | 6 | 21 |
| Example 169 | PMCR20 | 21 | 73** | 34# | 28# | 9 | 17 | 109# | 6 | 14 |
| Example 171 | PMCR25 | 23 | 52** | 56# | 40# | 78# | 59# | 34# | −5 | 28# |
| Example 188 | PMCR45 | 42 | 63** | 67# | 41# | 116# | 123# | 49# | 19 | 20 |
| Example 397 | PMCR55 | 68** | 83** | 90# | 72# | 137# | 199# | 1 | 59# | 40# |
| Example 205 | PMCR75 | 61** | 90** | 70# | 41# | 31# | 15 | 4 | 46# | 61# |
| Example 230 | PMCR120 | 60** | 27 | 13 | 16 | 11 | 6 | 17 | −4 | 85# |
| Example 232 | PMCR122 | 55** | 66** | 45# | 32# | 20 | 37# | 210# | 6 | 11 |
| Example 244 | PMCR147 | 0 | 87** | 70# | 63# | 68# | 124# | 180# | 25# | 28# |
| Example 283 | PMCR188 | 53 | 0 | 92# | 60# | 148# | 160# | 250# | 0 | 0 |
| Example 297 | PMCR204 | 55** | 33 | 70# | 65# | 164# | 214# | 207# | −8 | 12 |
| Example 298 | PMCR206 | 31 | 33 | 0 | 12 | 0 | −1 | 147# | 11 | 30# |
| Example 303 | PMCR216 | 60** | 10 | 6 | −1 | −10 | 0 | 152# | −21 | 16 |
| Example 308 | PMCR224 | 80** | 45 | 63# | 43# | 18 | 28# | 266# | −4 | 13 |
| Example 313 | PMCR236 | 68** | 32 | 94# | 60# | 91# | 39# | 172# | 6 | 19 |
| Example 319 | PMCR242 | 66** | 84** | 90# | 60# | 68# | 61# | 50# | −28 | 14 |
| | PMCR302 | 27 | 67** | 81# | 77# | 68# | 125# | 4 | 16 | 48# |

| $IC_{50}$ concentrations | | |
|---|---|---|
| | NF-κB | AP-1 |
| PMCR 20 | — | 10 μM* |
| PMCR 75 | 500 nM* | 200 nM* |
| PMCR 120 | 10 μM* | — |
| PMCR 242 | 10 μM* | 5 μM* |

As shown in Table 12, functional assays identified 18 compounds with greater than 50% inhibition of either AP-1 or NF-κB activity (Values marked with **). From the toxicology assays, the percent (over 25%) viable endothelial or epithelial cells, percent increase in LDH release, or ethidium homodimer fluorescence, relative to vehicle control cells were also tested in two pairs of cell lines from the skin or prostate, one tumorigenic and one non-tumorigenic, to test for differing toxicity or heightened sensitivity in the tumorigenic lines. The cells were treated for 48 h with vehicle (0.1%

DMSO) or 10 μM of each drug candidate, and the viability of the cells was determined by the MTT assay, expressed as a % decrease in viability compared to vehicle-treated cells. The in vivo inflammation model measured the % inhibition of rat paw edema induced by carageenan injection.

TABLE 13

Summary of Properties of Four Lead Compounds

| Compound | NF-κB % inhibition | AP-1 % inhibition | VSMC Toxicity | HUVEC Toxicity | HPT Toxicity | Differential Toxicity* | | In vivo inflammation % inhibition |
|---|---|---|---|---|---|---|---|---|
| | | | | | | Skin | Prostate | |
| PMCR 20 | 21 | 73 | – | – | + | Neither | Cancer | 42 |
| PMCR 75 | 61 | 90 | + | – | – | Both | Normal | 56 |
| PMCR 120 | 60 | 27 | – | – | – | Cancer | Both | 58 |
| PMCR 242 | 66 | 84 | + | + | + | Neither | Cancer | 80 |

Miscellaneous

Anticancer Activities of Compounds

The compounds identified in this invention may be used for the treatment of cancer or other proliferative disorders. A compound's activity may be measured against a known cancer cell line or against primary cancer cells for its ability to inhibit cancer cell growth, cancer cell migration, invasion or metastasis, or for the ability to cause death of the cancer cell. Some of the cell lines which can be used in such testing include, without limitation, MCF-7, MDA-MB-231, FaDu, DU145, PC3, and SKBR3. A compound's activity to inhibit growth/viability may be tested, for example, in the NIH cell screening assay, which provides access to over 60 different cancer cell lines representing a large number of different cancer types. For each compound that inhibits cancer cell growth or cause cancer cell death in vitro, further tests will confirm that the compound has low toxicity to normal, non-cancerous cells, such as WI-38 cells. The compound is then tested in standard animal models for its ability to kill tumors, prevent/inhibit tumor growth, or prevent/inhibit tumor metastasis. Additionally, a compound may be tested for its ability to prevent/inhibit tumor recurrence. A number of animal models are available for these tests and are well known to those skilled in the art. A compound can be administered to an animal either alone or in combination, including combinations with other known or suspected anticancer agents. Compounds demonstrating efficacy in an animal model will then be tested for human efficacy through an FDA approved protocol in clinical trials generally similar to those used to test other anticancer agents.

Compound Administration

Compounds of the present invention may be administered in pharmaceutical compositions to treat patients (humans and other mammals) with auto-immune disorders, inflammation, or cancer. Thus, the invention includes pharmaceutical compositions containing at least one compound from the present invention and a pharmaceutically acceptable carrier. A composition of the invention may further include at least one other therapeutic agent, for example, a combination formulation or combination of differently formulated active agents for use in a combination therapy method.

The present invention also features methods of using or preparing or formulating such pharmaceutical compositions. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to give slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Singer's solution and isotonic sodium chloride. Such forms will be presented in unit dose form such as ampoules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation consisting of the compound of the invention and a suitable carrier.

Methods are known in the art for determining effective doses for therapeutic (treatment) and prophylactic (preventative) purposes for the pharmaceutical compositions or the drug combinations of the present invention, whether or not formulated in the same composition. The specific dosage level required for any particular patient will depend on a number of factors, including severity of the condition being treated, the route of administration, and the weight of the patient. For therapeutic purposes, "effective dose" or "effective amount" refers to that amount of each active compound or pharmaceutical agent, alone or in combination, that elicits the biological or medicinal response in a tissue system, animal, or human that is being sought by a researcher, veterinarian, medical doctor, or other clinician, which includes alleviation of the symptoms of the disease or disorder being treated. For prophylactic purposes (i.e., preventing or inhibiting the onset or progression of a disorder), the term "effective dose" or "effective amount" or "therapeutically effective dose" or "therapeutically effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by the NF-κB and/or AP-1 mediated transcription factors and/or the post-transcriptional regulation through eIF4E and/or AREs. Methods of combination therapy include co-administration of a single formulation containing all active agents; essentially contemporaneous administration of more than one formulation; and administration of two or more active agents separately formulated.

It is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg. Preferably, oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 μg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

It will be appreciated that, although specific embodiments of this invention have been described herein for purpose of illustration, various modification may be made without departing from the spirit and scope of the invention.

The complete disclosures of all references cited in this specification are hereby incorporated by reference, as is the complete disclosures of priority U.S. provisional patent applications 60/790,105 and 60/795,430. In the event of an otherwise irreconcilable difference, however, the present specification shall govern.

References

1. Rajappa, S., et al. (1979) *J. Chem. Soc Perkins Trans. I*, 1762.
2. Rajasekharan, K. N. (1986) *Synthesis*, 353.
3. Palanki, M. S. S. P. M., A. M. (1999) *Exp. Opin. Ther. Patents*, 9, 27.
4. Manning, A. M. (1996) *Drug Discovery Today*, 1, 151-160.
5. Lewis, A. J. (1996) *In Emerging Drugs: The prospect for Improved Medicines, Annual Executive Briefing*, Ashley Publications Ltd., 31.
6. Brandhuber, B. J. B. T., Kenney, W. C.; McKay D. B. (1987) Three-dimensional structure of interleukin-2. *Science*, 238, 1707-1709.
7. MoorthyS. S., Palanki. (2002) *Current Medicinal Chemistry*, 9, 219-227.
8. Angel, P. K., M. (1991) The role of Jun, Fos and the AP-1 complex in cell-proliferation and transformation. *Biochim. Biophys. Acta*, 1072, 129-157.
9. Ryseck, R., Bravo, R. (1991) c-JUN, JUN B, and JUN D differ in their binding affinities to AP-1 and CRE consensus sequences: effect of FOS proteins. *Oncogene*, 6, 533-542.
10. Whitmarsh, A., Shore, P, Sharrocks, A D, Davis, R J. (1995) Integration of MAP kinase signal transduction pathways at the serum response element. *Science*, 269, 403-407.
11. Pahl, H. (1999) Activators and target genes of Rel/NF-kappaB transcription factors. *Oncogene*, 18, 6853-6866.
12. Karin, M. and Delhase, M. (2000) The I[kappa]B kinase (IKK) and NF-[kappa]B: key elements of proinflammatory signalling *Seminars in Immunolog*, 12, 85-98.
13. Karin, M. (1999) How NF-kappaB is activated: the role of the IkappaB kinase (IKK) complex. *Oncogene*, 18, 6867-6874.
14. Shaw, K., Ho, A., Raghavan, A., Kim, J., Jain, J., Park, J., Sharma, S., Rao, A. and Hogan, P. (1995) Immunosuppressive Drugs Prevent a Rapid Dephosphorylation of Transcription Factor NFAT 1 in Stimulated Immune Cells *PNAS*, 92, 11205-11209.
15. Rao, A., Luo, C, Hogan, P G. (1997) Transcription factors of the NFAT family: regulation and function. *Annu Rev Immunol.*, 15, 707-747.
16. Porter, C. M., Havens, M. A. and Clipstone, N. A. (2000) Identification of Amino Acid Residues and Protein Kinases Involved in the Regulation of NFATc Subcellular Localization *J. Biol. Chem.*, 275, 3543-3551.
17. Giordano, A., Powers, G. D., Sturgess, M. A. and Yang, K. (2003) Identification of compounds for the treatment or prevention of proliferative diseases U.S. Pat. No. 6,630, 589 B1.
18. Child, S. J., Miller, M. K. and Geballe, A. P. (1999) Cell type-dependent and -independent control of HER-2/neu translation. *Int J. Biochem. Cell Biolog*, 31, 201-213.
19. Child, S. J., Miller, M. K. and Geballe, A. P. (1999) Translational control by an upstream open reading frame in the HER-2/neu transcript. *J Biol Chem*, 274, 24335-24341.
20. De Benedetti, A. and Graff, J. R. (2004) eIF-4E expression and its role in malignancies and metastases *Oncogene*, 23, 3189-3199.

21. Mamane, E., Petroulakis, E., Rong, L., Yoshida, K., Ler, L. W. and Sonenberg, N. (2004) eIF4E—from translation to transformation *Oncogene,* 23, 3172-3179.
22. Li, B. D. L., McDonald, J., Nassar, R. and De Benedetti, A. (1998) Clinical outcome in stage 1 to 3 breast carcinomas and eIF4E overexpression *Ann. Surg. Soc.,* 227, 756-762.
23. Sliva, D. (2004) Signaling pathways responsible for cancer cell invasion as targets for cancer therapy. *Curr Cancer Drug Targets,* 4, 327-336.
24. Sliva, D., English, D., Lyons, D., Lloyd, F. P., Jr. (2002) Protein kinase C induces motility of breast cancers by upregulating secretion of urokinase-type plasminogen activator through activation of AP-1 and NF-κB. *Biochem. Biophys. Res. Comm.,* 290, 552-557.
25. Shi, Q., Le, X., Abbruzzese, J. L., Wang, B., Mujaida, N., Matsushima, K., Huang, S., Xiong, Q., Xie, K. (1999) Cooperation between transcription factor AP-1 and NF-κB in the induction of interleukin-8 in human pancreatic adenocarcinoma cells by hypoxia. *J. Interferon Cytokine Res.,* 19, 1363-1371.
26. Hahn, W. (2002) Rules for making human tumor cells. *New Engl J Med,* 347, 1593-1603.
27. Leaf, C. (2004) Why we're losing the war on cancer (and how to win it). *Fortune,* 149, 77-96.
28. Li, J. J., Westergaard, C., Ghosh, P., Colbum, N. H. (1997) Inhibitors of both nuclear factor-kappaB and activator protein-1 activation block the neoplastic transformation response. *Cancer Res.,* 57, 3569-3576.
29. Bancroft C C, C. Z., Dong G, Sunwoo J B, Yeh N, Park C, Van Waes C. (2001) Coexpression of proangiogenic factors IL-8 and VEGF by human head and neck squamous cell carcinoma involves coactivation by MEK-MAPK and IKK-NF-kappaB signal pathways. *Clin. Cancer Res.,* 7, 435-442.
30. Duvoix, A., Delhalle, S., Blasius, R., Schnekenburger, M., Morceau, F., Fougere, M., Henry, E., Galteau, M., Dicato, M., Diedrich, M. (2004) Effect of chemopreventive agents on glutathione S-transferase p1-1 gene expression mechanisms via activating protein 1 and nuclear factor kappaB inhibition. *Biochemical Pharmacology,* 68, 1101-1111.
31. Eferl, R., Wagner, E. F. (2003) AP-1: A double-edged sword in tumorigenesis. *Nature Reviews,* 3, 859-868.
32. Karin, M., Yamamoto, Y., Wang, Q. M. (2004) The IKK NF-κB system: A treasure trove for drug development *Nature Reviews,* 3, 17-26.
33. Shaulian, E., Karin, M. (2002) AP-1 as a regulator of cell life and death. *Nature Cell Biology,* 4, e131-e135.
34. Kikuchi, T., Hagiwara, K., Honda, Y., Gomi, K., Kobayashi, T., Takahashi, H., Tokue, Y., Watanabe, A., Nukiwa, T. (2002) Clarithromycin suppresses lipopolysaccharide-induce interleukin-8 production by human monocytes through AP-1 and NF-κB transcription factors. *J. Antimicrobial Chemotherapy,* 49, 645-755.
35. Sancho, R., Macho, A., de La Vega, L., Calzado, M. A., Fiebich, B. L., Appendino, G., Munoz, E. (2004) Immunosuppressive activity of endovanilloids: N-arachidonoyl-dopamine inhibits activation of the NF-κB, NFAT, and Activator Protein 1 signaling pathways. *J. Immunology,* 172, 2341-2351.
36. Ahmed, S., Wang, N., Lalonde, M., Goldberg, V. M., Haqqi, T. M. (2004) Green tea polyphenol epigallocatechin-3-gallate (EGCG) differentially inhibits interleukin-1b-induced expression of matrix metalloproteinase-1 and -13 in human chondrocytes. *J. Pharm. Exp. Therap.,* 3, 767-773.
37. Tachibana, H., Koga, K., Fujimura, Y., Yamada, K. (2004) A receptor for green tea polyphenol EGCG *Nature Struct. & Mol. Biol.,* 11, 380-381.
38. Sah, J. F., Balasubramanian, S., Eckert, R. L. and Rorke, E. A. (2004) Epigallocatechin-3-gallate inhibits epidermal growth factor receptor signaling pathway. Evidence for direct inhibition of ERK1/2 and AKT kinases. *J Biol Chem,* 279, 12755-12762.
39. Pilorget, A., Berthet, V., Luis, J., Moghrabi, A., Annabi, B. and Beliveau, R. (2003) Medulloblastoma cell invasion is inhibited by green tea (−) epigallocatechin-3-gallate. *Cell Biochem.,* 90, 745-755.
40. Leone, M., Zhai, D., Sareth, S., Kitada, S., Reed, J. C., Pellecchia, M. (2003) Cancer prevention by tea polyphenols is linked to their direct inhibition of antiapoptotic Bcl-2-family proteins. *Cancer Res.,* 63, 8118-8121.
41. Chow, H. H., Cai, Y., Hakim, L A., Crowell, J. A., Shahi, F., Brooks, C. A., Dorr, R. T., Hara, Y. and Alberts, D. S. (2003) Pharmacokinetics and safety of green tea polyphenols after multiple-dose administration of epigallocatechin gallate and polyphenol E in healthy individuals. *Clin. Cancer Res.,* 9, 3312-3319.
42. Ahn, W. S., Yoo, J., Huh, S. W., Kinm, C. K., Lee, J. M., Namkoong, S. E., Bae, S. M. and Lee, I. P. (2003) Protective effects of green tea extracts (polyphenol E and EGCG) on human cervical lesions. *Eur J Cancer Prev.,* 12, 383-390.
43. Aggarwal, B. B., Kumar, A., Bharti, A. C. Anticancer Res. 23:363-398). (2003) Anticancer potential of curcumin: preclinical and clinical studies. *Anticancer Res.,* 23, 363-398.
44. Surh, Y.-J. (2003) Cancer chemoprevention with dietary phytochemicals. *Nature Reviews,* 3, 768-780.
45. Sliva, D., Labarrere, C., Slivova, V., Sedlak, M., Lloyd, F. P., Jr., Ho, N. W. Y. (2002) *Ganoderma lucidum* suppresses motility of highly invasive breast and prostate cancer cells. *Biochem. Biophys. Res. Comm.,* 298, 603-612.
46. Keum, Y. S., Han, S. S., Chun, K. K., Park, J. H., Lee, S. K., Surh, Y. J. (2003) Inhibitory effects of the ginsenoside Rg3 on phorbal ester-induced cyclooxygenase-2 expression, NF-kappaB activation and tumor promotion. *Mutation Res.,* 523-524, 75-85.
47. Sreenivasan, Y., Sarkar, A., Manna, S. K. (2003) Oleandrin suppresses activation of nuclear transcription factor-κB and activator protein-1 and potentiates apoptosis induced by ceramide. *Biochem. Pharm.,* 66, 2223-2239.
48. Mori, N., Matsuda, T., Tadano, M., Kinjo, T., Yamada, Y., Tsukaki, K., Ikeda, S., Yamasaki, Y., Tanaka, Y., Ohta, T., Jwamasa, T., Tomonaga, M., Yamamoto, N. (2004) Apoptosis induced by the histone deacetylase inhibitor FR901228 in human T-cell leukemia virus type 1-infected T-cell lines and primary adult T-cell leukemia cells. *J. Virol.,* 78, 4582-4590.
49. Collins, T. S., Lee, L. F. and Ting, J. P. (2000) Paclitaxel up-regulates interleukin-8 synthesis in human lung carcinoma through an NF-kappaB- and AP-1-dependent mechanism *Cancer Immunol Immunother,* 49, 78-84.
50. Clemens, M. J. (2004) Targets and mechanisms for the regulation of translation in malignant transformation. *Oncogene,* 23, 3180-3188.
51. Huang, S. and Houghton, P. J. (2003) Targeting mTOR signaling for cancer therapy *Curr Opin Pharmacol.,* 3, 371-377.
52. DeFatta, R. J., Turbat-Herrera, E., Li, B. D. L., Anderson, W. and De Benedetti, A. (1999) Elevated expression of eIF4E in confined early breast cancer lesions: possible role of hypoxia *Int. J. Cancer,* 80, 516-522.

What is claimed:

1. A compound having the structure

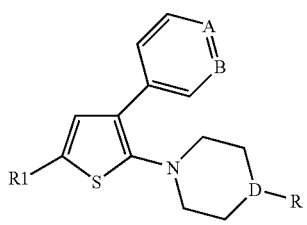

wherein:
A=C(R$_2$) or N
B=CH or N
D(R)=CH$_2$ or O or N(R)
R=H, or substituted or unsubstituted C$_{1-4}$ alkyl, aryl, aroyl, heteroaryl, or heteroaroyl
R$_1$=substituted or unsubstituted aryl, aroyl, heteroaryl, heteroaroyl, C$_{1-4}$ alkoximino, or C$_{1-8}$ esters
R$_2$=-fluoro, -bromo, —NHCOCH$_3$, SO$_2$CH$_3$, —SOCH$_3$, CF$_3$, or NH$_2$.

2. The compound of claim 1, wherein said compound has the structure

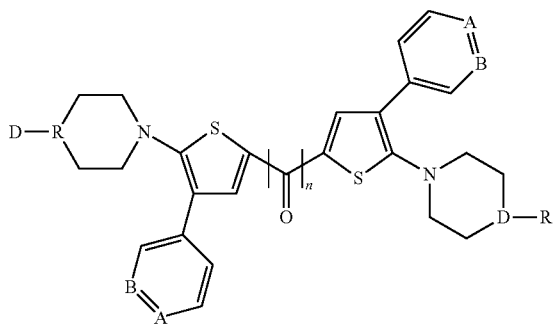

wherein n=1 or 2.

3. The compound of claim 1, wherein R$_1$ has one of the structures shown below:

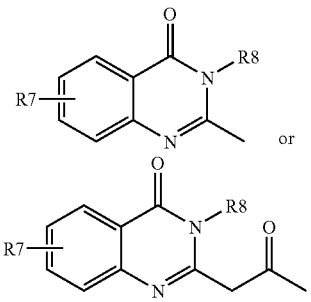

wherein:
R$_7$=—H or —Br
R$_8$=aryl or heteroaryl.

4. The compound of claim 1, wherein said compound is selected from the group consisting of:
2-[4-(4-methanesulphonyl-phenyl)-5-morpholin-4-yl-thiophen-2-yl]-3-(2-methoxy-phenyl)-3H-quinazolin-4-one;
2-[4-(4-methanesulphonyl-phenyl)-5-morpholin-4-yl-thiophen-2-yl]-3-(4-methoxy-phenyl)-3H-quinazolin-4-one;
2-[4-(4-methanesulphonyl-phenyl)-5-morpholin-4-yl-thiophen-2-yl]-3-(4-acetyl-phenyl)-3H-quinazolin-4-one; and
3-(4-acetyl-phenyl)-2-(5-morpholin-4-yl-4-pyridin-4-yl-thiophen-2-yl)-3Hquinazolin-4-one.

5. The compound of claim 4, wherein said compound is 2-[4-(4-methanesulphonyl-phenyl)-5-morpholin-4-yl-thiophen-2-yl]-3-(2-methoxy-phenyl)-3H-quinazolin-4-one.

6. The compound of claim 4, wherein said compound is 2-[4-(4-methanesulphonyl-phenyl)-5-morpholin-4-yl-thiophen-2-yl]-3-(4-methoxy-phenyl)-3H-quinazolin-4-one.

7. The compound of claim 4, wherein said compound is 2-[4-(4-methanesulphonyl-phenyl)-5-morpholin-4-yl-thiophen-2-yl]-3-(4-acetyl-phenyl)-3H-quinazolin-4-one.

8. The compound of claim 4, wherein said compound is 3-(4-acetyl-phenyl)-2-(5-morpholin-4-yl-4-pyridin-4-yl-thiophen-2-yl)-3Hquinazolin-4-one.

9. A composition comprising a compound and a pharmaceutical acceptable carrier or a pharmaceutically acceptable diluent; wherein said compound has the structure

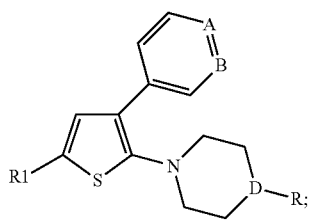

2-[4-(4-methanesulphonyl-phenyl)-5-morpholin-4-yl-thiophen-2-yl]-3-(2-methoxy-phenyl)-3H-quinazolin-4-one;

2-[4-(4-methanesulphonyl-phenyl)-5-morpholin-4-yl-thiophen-2-yl]-3-(4-methoxy-phenyl)-3H-quinazolin-4-one;

2-[4-(4-methanesulphonyl-phenyl)-5-morpholin-4-yl-thiophen-2-yl]-3-(4-acetyl-phenyl)-3H-quinazolin-4-one; or 3-(4-acetyl-phenyl)-2-(5-morpholin-4-yl-4-pyridin-4-yl-thiophen-2-yl)-3Hquinazolin-4-one;

wherein:
A=C($R_2$) or N
B=CH or N
D(R)=$CH_2$ or O or N(R)
R=H, or substituted or unsubstituted $C_{1-4}$ alkyl, aryl, aroyl, heteroaryl, or heteroaroyl
$R_1$=substituted or unsubstituted aryl, aroyl, heteroaryl, heteroaroyl, $C_{1-4}$ alkoximino, or $C_{1-8}$ esters
$R_2$=-fluoro, -bromo, —$NHCOCH_3$, $SO_2CH_3$, —$SOCH_3$, $CF_3$, or $NH_2$.

10. The compound of claim 1, wherein:
R=H, or substituted or unsubstituted $C_{1-4}$ alkyl;
$R_1$=substituted or unsubstituted aryl, aroyl, heteroaryl, heteroaroyl; and
$R_2$=—$NHCOCH_3$ or $SO_2CH_3$.

11. The compound of claim 3, wherein $R_1$ has the structure:

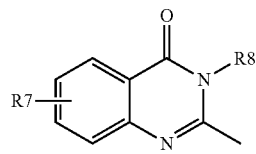

and wherein $R_7$=—H.

12. The composition of claim 9, wherein:
R=H, or substituted or unsubstituted $C_{1-4}$ alkyl;
$R_1$=substituted or unsubstituted aryl, aroyl, heteroaryl, heteroaroyl; and
$R_2$=—$NHCOCH_3$ or $SO_2CH_3$.

* * * * *